US012553059B2

(12) United States Patent
Mach et al.

(10) Patent No.: US 12,553,059 B2
(45) Date of Patent: Feb. 17, 2026

(54) PLANT SERINE PROTEASES

(71) Applicant: Universität für Bodenkultur Wien, Vienna (AT)

(72) Inventors: Lukas Mach, Langenzersdorf (AT); Alejandro Puchol Tarazona, Vienna (AT); Herta Steinkellner, Vienna (AT); Richard Strasser, Vienna (AT)

(73) Assignee: Universität für Bodenkultur Wien, Vienna (AT)

( * ) Notice: Subject to any disclaimer, the term of this patent is extended or adjusted under 35 U.S.C. 154(b) by 656 days.

(21) Appl. No.: 17/280,114

(22) PCT Filed: Oct. 2, 2019

(86) PCT No.: PCT/EP2019/076722

§ 371 (c)(1),
(2) Date: Mar. 25, 2021

(87) PCT Pub. No.: WO2020/070197

PCT Pub. Date: Apr. 9, 2020

(65) Prior Publication Data

US 2022/0228161 A1 Jul. 21, 2022

(30) Foreign Application Priority Data

Oct. 2, 2018 (EP) .................................... 18198240

(51) Int. Cl.
*C12N 15/82* (2006.01)
*C07K 16/10* (2006.01)
*C12N 9/50* (2006.01)

(52) U.S. Cl.
CPC ...... *C12N 15/8258* (2013.01); *C07K 16/1045* (2013.01); *C12N 9/63* (2013.01); *C07K 2317/14* (2013.01)

(58) Field of Classification Search
None
See application file for complete search history.

(56) References Cited

U.S. PATENT DOCUMENTS

2004/0106198 A1* 6/2004 Hanley et al. ..... C12N 15/8257 800/278

FOREIGN PATENT DOCUMENTS

WO 2013192545 A1 12/2013
WO 2016009006 A1 1/2016

OTHER PUBLICATIONS

Strasser et al. Generation of glyco-engineered Nicotiana benthamiana for the production of monoclonal antibodies with a homogeneous human-like N-glycan structure. (2008) Plant Biotechnology Journal; vol. 6; pp. 392-402 (Year: 2008).*

Niemer et al., The human anti-HIV antibodies 2F5, 2G12, and PG9 differ in their susceptibility to proteolytic degradation: Down-regulation of endogenous serine and cysteine proteinase activities could improve antibody production in plant-based expression, (2014), Biotech Journal, vol. 9, pp. 493-500 (Year: 2014).*

Fernandez-Pozo et al., The Sol Genomics Network (SGN)—from genotype to phenotype to breeding, 2015, Nucleic Acids Res., vol. 43 (Database issue): D1036-41, PubMed. https://solgenomics.net/tools/blast/?db_id=266 (Year: 2015).*

Bombarely et al., A draft genome sequence of nicotiana benthamiana to enhance molecular plant-microbe biology research, 2012, Molecular Plant-Microbe Interactions, vol. 25(12), pp. 1523-1530 (Year: 2012).*

Beritza et al., SBT5.2s are the major active extracellular subtilases processing IgG antibody 2F5 in the Nicotiana benthamiana apoplast, 2024, Plant Biotechnology Journal, vol. 22(10), pp. 2808-2010 (Year: 2024).*

International Search Report from Appl. No. PCT/EP2019/076722 mailed on Nov. 27, 2019.

Databased UniProt, SubName: Full= subtilisin-like protease SBT5.3, retrieved from EBI accession No. UniProt: A0A1U7X287, (May 10, 2017).

Databased UniProt, SubName: Full=CO (2)-response secreted protease-like; retrieved from EBI accession No. UniProt: A0A1S4C9U6, (Mar. 12, 2017).

Databases RefSeq, CO(2)-response secreted protease [Solanum lycopersicum], retrieved from NCBI accession No. XP_004238378, (Aug. 8, 2018).

Database UniProt, SubName: Full= Uncharacterized protein, retrieved from EBI accession No. M1AM09, (Apr. 3, 2013).

Database RefSeq, Predicted: subtilisin-like protease SBT1.9 [ Nicotiana attenuata], retrieved from NCBI accession No. XP_019231474, (Dec. 5, 2016).

(Continued)

*Primary Examiner* — Bratislav Stankovic
*Assistant Examiner* — Christina L Meadows
(74) *Attorney, Agent, or Firm* — Nevrivy Patent Law Group P.L.L.C.

(57) ABSTRACT

The present invention relates to a genetically modified plant or plant cell derived from a wild-type plant or plant cell, said wild-type plant or plant cell producing at least one serine protease comprising the motif SSRGPX$_1$LKPDX$_2$X$_3$APGX$_4$SGTSMSCPHX$_5$PX$_6$WSPX$_7$AX$_8$X$_9$SAX$_{10}$MTT (SEQ ID No. 1), wherein X$_1$ is a peptide consisting of 7 amino acid residues, X$_2$ is I or L, X$_3$ is T or M, X$_4$ is a peptide consisting of 27 or 28 amino acid residues, X$_5$ is a peptide consisting of 12 amino acid residues, X$_6$ is T or E, X$_7$ is S or A, X$_8$ is V or I, X$_9$ is K or R and X$_{10}$ is I or M, wherein the proteolytic activity of the at least one serine protease in the genetically modified plant or plant cell is reduced compared to its activity in the wild-type plant or plant cell, wherein the genetically modified plant or plant cell comprises at least one exogenous nucleic acid molecule encoding for at least one protein or polypeptide of interest.

7 Claims, 15 Drawing Sheets

Specification includes a Sequence Listing.

(56) References Cited

OTHER PUBLICATIONS

Database RefSeq, subtilisin-like protease SBT1.9 [Solanum lycopersicum], retrieved from NCBI accession No. XP_010320328, (Aug. 8, 2018).

Database RefSeq, Predicted: subtilisin-like protease SBT1.7, [Solanum tuberosum], etrieved from NCBI accession No. XP_015167554, (Jan. 5, 2016).

Niemer et al., The human anti-HIV antibodies 2F5, 2G12, and PG9 differ in their susceptibility to proteolytic degradation: Down-regulation of endogenous could improve antibody production in plant-based expression platforms, Biotechnology Journal, (2014), 9: 493-500.

Mandal et al., Inhibition of protease activity by antisense RNA improves recombinant portein production in Nicotiana tabacum cv. Bright Yellow 2(BY-2) suspension cells, Biotechnology Journal, (2014) 9: 1065-1073.

Navarre et al., Identification, gene cloning and expression of serine proteases in the extracellular medium of Nicotiana tabacum cells, Plant Cell Reports, (2012), 31: 1959-1968.

Mandal et al., Tackling Unwanted Proteolysis in Plant Production Hosts Used for Molecular Farming, Frontiers in Plant Science, (2016), 7: 1-4.

Puchol-Tarazona et al., Degradation of anti-HIV antibodies 2F5 and PG9 by proteases of Nicotiana benthamiana, New Biotechnology, (2018), 44:1871-6784.

Ottmann et al., Structural basis for Ca2+-independence and activation by homodimerizatin of tomato subtilase 3, PNAS, (2009), 106:17223-17228.

* cited by examiner

| | $K_i$ (nM) |
|---|---|
| At1 | 21 ± 1 |

| | $K_i$ (nM) |
|---|---|
| **At2** | 81 ± 8 |

| | $K_i$ (nM) |
|---|---|
| Sl1 | 41 ± 2 |

| | $K_i$ (nM) |
|---|---|
| **Sl2** | 51 ± 3 |

| | $K_i$ (nM) |
|---|---|
| **At1** | 8 ± 1 |

| | $K_i$ (nM) |
|---|---|
| At2 | 45 ± 3 |

| | $K_i$ (nM) |
|---|---|
| Sl1 | 27 ± 2 |

| | $K_i$ (nM) |
|---|---|
| Sl2 | 24 ± 2 |

SEQUENCE LISTING

<160> NUMBER OF SEQ ID NOS: 37

<210> SEQ ID NO 1
<211> LENGTH: 85
<212> TYPE: PRT
<213> ORGANISM: Artificial Sequence
<220> FEATURE:
<223> OTHER INFORMATION: Serine protease motif
<220> FEATURE:
<221> NAME/KEY: MISC_FEATURE
<222> LOCATION: (6)..(12)
<223> OTHER INFORMATION: X is a variable amino acid
<220> FEATURE:
<221> NAME/KEY: MISC_FEATURE
<222> LOCATION: (17)..(17)
<223> OTHER INFORMATION: X is I or L
<220> FEATURE:
<221> NAME/KEY: MISC_FEATURE
<222> LOCATION: (18)..(18)
<223> OTHER INFORMATION: X is T or M
<220> FEATURE:
<221> NAME/KEY: MISC_FEATURE
<222> LOCATION: (22)..(48)
<223> OTHER INFORMATION: X is a variable amino acid
<220> FEATURE:

```
<221> NAME/KEY: MISC_FEATURE
<222> LOCATION: (49)..(49)
<223> OTHER INFORMATION: X is either present or absent and is a variable
      amino acid
<220> FEATURE:
<221> NAME/KEY: MISC_FEATURE
<222> LOCATION: (59)..(70)
<223> OTHER INFORMATION: X is a variable amino acid
<220> FEATURE:
<221> NAME/KEY: MISC_FEATURE
<222> LOCATION: (72)..(72)
<223> OTHER INFORMATION: X is T or E
<220> FEATURE:
<221> NAME/KEY: MISC_FEATURE
<222> LOCATION: (76)..(76)
<223> OTHER INFORMATION: X is S or A
<220> FEATURE:
<221> NAME/KEY: MISC_FEATURE
<222> LOCATION: (78)..(78)
<223> OTHER INFORMATION: X is V or I
<220> FEATURE:
<221> NAME/KEY: MISC_FEATURE
<222> LOCATION: (79)..(79)
<223> OTHER INFORMATION: X is K or R
<220> FEATURE:
<221> NAME/KEY: MISC_FEATURE
<222> LOCATION: (82)..(82)
<223> OTHER INFORMATION: X is I or M

<400> SEQUENCE: 1

Ser Ser Arg Gly Pro Xaa Xaa Xaa Xaa Xaa Xaa Xaa Leu Lys Pro Asp
1               5                   10                  15

Xaa Xaa Ala Pro Gly Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Ser Gly Thr Ser Met Ser Cys Pro His Xaa Xaa Xaa Xaa Xaa Xaa
    50                  55                  60

Xaa Xaa Xaa Xaa Xaa Xaa Pro Xaa Trp Ser Pro Xaa Ala Xaa Xaa Ser
65                  70                  75                  80

Ala Xaa Met Thr Thr
                85


<210> SEQ ID NO 2
<211> LENGTH: 770
<212> TYPE: PRT
<213> ORGANISM: Nicotiana benthamiana

<400> SEQUENCE: 2

Met Lys Gly Ile Ile Ser Leu Phe Phe Cys Phe Ser Leu Phe Ile Val
1               5                   10                  15

Ser Phe Ile Leu Arg Glu Ala Asp Ser Ala Ser Gln Ala Gln Asn Asn
            20                  25                  30

Gly Ile Tyr Ile Val Tyr Met Gly Ala Ala Ala Ser Ser Asn Gly Gly
        35                  40                  45

Thr Arg His Asp Gln Ala Arg Leu Ile Ser Ser Leu Ile Arg Arg Asn
    50                  55                  60

Lys His Ala Val Val His Ser Tyr Asn Asn Gly Phe Ser Gly Phe Ala
65                  70                  75                  80

Ala Arg Leu Ser Glu Ser Glu Ala Lys Ser Met Ala Gln Arg Pro Gly
                85                  90                  95

Val Ile Ser Val Phe Pro Asp Pro Val Leu Gln Leu His Thr Thr His
            100                 105                 110

Ser Trp Asp Phe Leu Lys Tyr Gln Thr Asp Glu Lys Ile Asn Ser Ser
```

```
        115                 120                 125

Pro Ser Ser Gly Ser Asp Ser Ser Leu Ile Gly Ala Asp Thr Ile Ile
    130                 135                 140

Gly Ile Leu Asp Thr Gly Ile Trp Pro Glu Ser Glu Ser Phe Asn Asp
145                 150                 155                 160

Lys Asp Met Gly Pro Ile Pro Ser Arg Trp Asn Gly Thr Cys Met Asp
                165                 170                 175

Gly Gln Asp Phe Gly Ser Ser Lys Cys Asn Lys Lys Ile Val Gly Ala
            180                 185                 190

Arg Phe Tyr Glu Glu Ser Asp Asp Ser Gly Thr Lys Ile Ala Gly Ser
        195                 200                 205

Ala Arg Asp Glu Asn Gly His Gly Thr His Val Ala Ser Thr Ala Ala
    210                 215                 220

Gly Ser Pro Val Ala Gly Ala Ser Tyr Tyr Gly Leu Ala Ala Gly Thr
225                 230                 235                 240

Ala Thr Gly Gly Ser Pro Gly Ser Arg Ile Ser Met Tyr Arg Val Cys
                245                 250                 255

Thr Thr Phe Gly Cys Arg Gly Ser Ala Ile Met Lys Ala Phe Asp Asp
            260                 265                 270

Ala Ile Ala Asp Gly Val Asp Val Leu Ser Leu Ser Leu Gly Ser Ser
        275                 280                 285

Pro Gly Leu Glu Pro Asp Phe Pro Ser Asn Pro Ile Ala Ile Gly Ala
    290                 295                 300

Phe His Ala Val Glu Lys Gly Ile Thr Val Val Cys Ser Ala Gly Asn
305                 310                 315                 320

Ser Gly Pro Gly Pro Lys Thr Val Val Asn Thr Ala Pro Trp Ile Leu
                325                 330                 335

Thr Val Ala Ala Thr Thr Ile Asp Arg Asp Phe Glu Thr Asp Ile Val
            340                 345                 350

Leu Gly Gly Asn Lys Leu Ile Lys Gly Gly Gly Ile Asn Phe Gly Asn
        355                 360                 365

Met Thr Lys Ser Ser Val Tyr Pro Leu Ile His Gly Asn Ser Thr Lys
    370                 375                 380

Ser Asn Asp Asn Val Ser Glu Ala Asp Ala Arg Ser Cys Val Pro Gly
385                 390                 395                 400

Ser Leu Asp Glu Asn Lys Val Lys Gly Lys Ile Val Leu Cys Glu Asn
                405                 410                 415

Leu Asp Asp Gly Glu Tyr Phe Pro Ser Asp Lys Leu Asp Glu Val Lys
            420                 425                 430

Ser Arg Gly Gly Val Gly Phe Ile Leu Ile Asp Asp Asp Glu Arg Thr
        435                 440                 445

Val Ala Pro Lys Phe Asn Ser Phe Ser Ala Gly Val Val Ser Lys Lys
    450                 455                 460

Asp Gly Asn Glu Ile Leu Ala Tyr Ile Asn Ser Thr Arg Asn Pro Val
465                 470                 475                 480

Ala Ser Ile Leu Pro Thr Val Ser Ile Thr Lys Tyr Lys Pro Ala Pro
                485                 490                 495

Val Val Ala Tyr Phe Ser Ser Arg Gly Pro Ala Tyr Asn Thr Pro Asn
            500                 505                 510

Leu Leu Lys Pro Asp Ile Thr Ala Pro Gly Val Ala Ile Leu Ala Ala
        515                 520                 525

Trp Pro Gly Asn Asp Thr Ser Glu Ala Leu Pro Gly Gln Lys Pro Pro
    530                 535                 540
```

```
Ile Phe Asn Leu Leu Ser Gly Thr Ser Met Ser Cys Pro His Val Ser
545                 550                 555                 560

Gly Ile Ala Ala Thr Val Lys Ala Val Asn Pro Thr Trp Ser Pro Ser
                565                 570                 575

Ala Val Lys Ser Ala Ile Met Thr Thr Ala Ile Gln Thr Asn Asn Leu
            580                 585                 590

Lys Ala Pro Ile Thr Thr Val Ser Gly Ser Lys Ala Thr Pro Tyr Asp
        595                 600                 605

Ile Gly Ala Gly Glu Ala Ser Thr Ser Gly Pro Leu Lys Pro Gly Leu
    610                 615                 620

Val Tyr Glu Thr Asp Val Ala Asp Tyr Leu Gln Phe Leu Cys Ser Val
625                 630                 635                 640

Gly Phe Asn Ile Ser Gln Ile Lys Leu Ile Ser Ile Thr Val Pro Glu
                645                 650                 655

Asp Phe Ser Cys Pro Lys Asn Ser Thr Ser Glu Leu Val Ser Asn Met
            660                 665                 670

Asn Tyr Pro Ser Ile Ala Ile Ser Ser Leu Lys Glu Asn Glu Pro Lys
        675                 680                 685

Lys Val Thr Arg Thr Val Thr Asn Thr Gly Glu Glu Ala Ser Val Tyr
    690                 695                 700

Thr Thr Val Ile Glu Ala Pro Lys Gly Leu Glu Val Gln Val Ile Pro
705                 710                 715                 720

Thr Lys Leu Glu Phe Thr Asn Lys Ser Lys Lys Leu Ser Tyr Asp Val
                725                 730                 735

Ser Phe Lys Ala Ser Ser Thr Ser Lys Glu Asp Leu Phe Gly Ser Ile
            740                 745                 750

Thr Trp Thr Asn Gly Lys Tyr Lys Val Arg Ser Pro Phe Val Val Ser
        755                 760                 765

Ser Asn
    770


<210> SEQ ID NO 3
<211> LENGTH: 2313
<212> TYPE: DNA
<213> ORGANISM: Nicotiana benthamiana

<400> SEQUENCE: 3

atgaaaggaa ttatatcttt gtttttctgc ttttctcttt tcattgtctc tttcatatta      60

agagaagccg actcagcttc tcaagcacaa aacaatggaa tttatattgt ttatatgggt     120

gctgcagctt catctaatgg tggtaccaga catgatcaag cgcggcttat cagctccttg     180

atcagaagga acaagcatgc agtggtacac agctacaaca atggtttctc aggattcgcg     240

gcacgtttat cagaatctga agctaaatcc atggctcaaa gacctggagt tatctccgta     300

tttcctgatc cagtactgca actccacact acacattcat gggatttctt gaagtatcaa     360

actgatgaaa aaatcaattc aagtccaagc tctggttctg attcatcatt aattggagct     420

gataccataa ttggcatatt ggatacgggt atatggccag aatctgagag tttcaatgac     480

aaggatatgg gtccaattcc atcccggtgg aatggaactt gcatggatgg tcaagatttt     540

ggctcttcaa aatgcaacaa gaagatagtt ggtgcaagat tttatgagga gtctgatgac     600

agtggaacaa aaatcgctgg atcagccagg gacgagaacg gacatggtac tcatgttgcg     660

tctactgcag ctgggagtcc tgttgcaggt gcatcctact atggcctagc tgcaggaact     720

gccacgggtg gatctcctgg ttcgaggatt tccatgtatc gtgtctgtac tacttttgga     780
```

```
tgccgcggat cagctatcat gaaagcattc gatgatgcaa ttgcagatgg ggttgatgtt    840

ttatcactat cacttggttc atcacctgga cttgaacctg attttccaag caatcctatt    900

gccataggag catttcatgc tgtagaaaag ggcattactg ttgtttgctc tgctggaaat    960

agtggccctg gaccaaaaac tgttgtcaat acagctcctt ggattcttac tgttgcagcc   1020

accaccattg atcgtgactt cgagacagat attgtcttgg gtggaaacaa gcttattaag   1080

ggtggaggta taaactttgg taacatgaca aaatcgtcag tctacccttt gattcatggc   1140

aattcaacca aatcaaacga taatgtttct gaggcggatg caaggagttg tgttcctggt   1200

tcattagatg aaaacaaagt caaggggaag attgtccttt gtgaaaatct tgatgatggt   1260

gaatattttc ccagtgacaa gctagatgaa gtgaaaagcc gaggtggagt tggatttata   1320

cttatagatg atgatgaaag aactgtggca cccaaattca attccttctc agctggtgta   1380

gtctctaaaa aggatggaaa tgagatcctc gcctacatta actcgacgag gaatccagtt   1440

gcatcaattt taccaactgt atccataaca aagtacaaac cagctccagt tgtggcttac   1500

ttctcatcaa gaggccctgc gtacaacacc cctaacctcc tcaaaccgga tattacagca   1560

ccaggggttg ccattcttgc tgcttggcct ggaaatgaca cgagtgaggc tctccccggc   1620

caaaaaccac caattttcaa cctactctca ggcacttcca tgtcctgccc tcatgtatcc   1680

ggtattgctg ctactgtcaa agcagtaaac cctacctgga gtccttcagc tgtcaaatca   1740

gctattatga ccacagctat tcagacaaac aatttgaagg ctccaatcac tacagtctca   1800

ggatccaaag caacaccata tgacataggt gcaggagaag caagcacttc aggtccatta   1860

aaaccaggtc tagtctacga gacagatgtc gccgactact tgcagttcct atgttctgtt   1920

ggttttaaca tatcacagat aaagctgatc tcaattacag ttcctgaaga cttttcatgc   1980

ccaaaaaact caacctctga attggtttct aatatgaatt atccatcaat agctatttct   2040

agtctcaaag aaaacgagcc gaagaaagtt actagaactg taacaaatac tggtgaagaa   2100

gcatcagtat atactacagt tattgaggca ccaaaaggat tggaagtcca agtgatccca   2160

actaaattgg aatttacaaa taaaagcaag aaattaagct atgatgtgtc tttcaaagct   2220

tcatctacct caaaggaaga tctgtttgga tcaattactt ggactaatgg taagtacaaa   2280

gtccggagtc cattcgtcgt aagtagcaac taa                                2313
```

```
<210> SEQ ID NO 4
<211> LENGTH: 768
<212> TYPE: PRT
<213> ORGANISM: Nicotiana tabacum

<400> SEQUENCE: 4

Met Lys Gly Leu Ser Leu Phe Phe Cys Phe Ser Leu Phe Ile Val Ala
1               5                   10                  15

Phe Ile Arg Glu Ala Asp Ser Ala Ser Gln Ala Gln Asn Asn Gly Ile
            20                  25                  30

Tyr Ile Val Tyr Met Gly Ala Ala Ala Ser Ser Asn Gly Gly Thr Arg
        35                  40                  45

His Asp Gln Ala Gln Leu Ile Ser Ser Leu Ile Arg Arg Asn Lys Asn
    50                  55                  60

Ala Val Val His Ser Tyr Asn Asn Gly Phe Ser Gly Phe Ala Ala Arg
65                  70                  75                  80

Leu Ser Glu Ala Glu Ala Lys Ser Met Ala Gln Arg Pro Gly Val Ile
                85                  90                  95
```

```
Ser Val Phe Pro Asp Pro Val Leu Gln Leu His Thr Thr His Ser Trp
            100                 105                 110

Asp Phe Leu Lys Tyr Gln Thr Asp Glu Lys Ile Asn Ser Ser Pro Ser
        115                 120                 125

Ser Gly Ser Asp Ser Ser Leu Ile Gly Ala Asp Thr Ile Ile Gly Ile
    130                 135                 140

Leu Asp Thr Gly Ile Trp Pro Glu Ser Glu Ser Phe Asn Asp Lys Asp
145                 150                 155                 160

Met Gly Pro Ile Pro Ala Arg Trp Asn Gly Thr Cys Met Asp Gly Gln
                165                 170                 175

Asp Phe Gly Ser Ser Lys Cys Asn Lys Lys Ile Val Gly Ala Arg Phe
            180                 185                 190

Tyr Glu Glu Ser Asp Asp Ser Gly Ile Lys Ile Ala Gly Ser Ala Arg
        195                 200                 205

Asp Glu Asn Gly His Gly Thr His Val Ala Ser Thr Ala Ala Gly Ser
    210                 215                 220

Pro Val Ala Gly Ala Ser Tyr Tyr Gly Leu Ala Ala Gly Thr Ala Thr
225                 230                 235                 240

Gly Gly Ser Pro Gly Ser Arg Ile Ala Met Tyr Arg Val Cys Thr Thr
                245                 250                 255

Phe Gly Cys Arg Gly Ser Ala Ile Met Lys Ala Phe Asp Asp Ala Ile
            260                 265                 270

Ala Asp Gly Val Asp Val Leu Ser Leu Ser Leu Gly Ser Ser Pro Gly
        275                 280                 285

Leu Glu Pro Asp Phe Pro Ser Asn Pro Ile Ala Ile Gly Ala Phe His
    290                 295                 300

Ala Val Glu Lys Gly Ile Val Val Val Cys Ser Ala Gly Asn Ser Gly
305                 310                 315                 320

Pro Gly Pro Lys Thr Val Val Asn Thr Ala Pro Trp Ile Leu Thr Val
                325                 330                 335

Ala Ala Thr Thr Ile Asp Arg Asp Phe Glu Thr Asp Ile Val Leu Gly
            340                 345                 350

Gly Asn Lys Leu Ile Lys Gly Gly Gly Ile Asn Phe Gly Asn Met Thr
        355                 360                 365

Lys Ser Ser Val Tyr Pro Leu Ile His Gly Asn Ser Thr Lys Ser Asn
    370                 375                 380

Asn Asn Val Ser Glu Ala Asp Ala Arg Ser Cys Val Pro Gly Ser Leu
385                 390                 395                 400

Asp Glu Asn Lys Val Lys Gly Lys Ile Val Leu Cys Glu Asn Leu Asp
                405                 410                 415

Asp Gly Glu Tyr Phe Pro Ser Asp Lys Leu Asp Glu Val Lys Ser Arg
            420                 425                 430

Gly Gly Val Gly Phe Ile Leu Ile Asp Asp Asp Glu Arg Thr Val Ala
        435                 440                 445

Pro Lys Phe Asn Ser Phe Pro Ala Gly Val Val Ser Lys Lys Asp Gly
    450                 455                 460

Thr Glu Ile Leu Ala Tyr Ile Asn Ser Thr Arg Asn Pro Ile Ala Ser
465                 470                 475                 480

Ile Leu Pro Thr Val Ser Ile Thr Lys Tyr Lys Pro Ala Pro Val Val
                485                 490                 495

Ala Tyr Phe Ser Ser Arg Gly Pro Ala Tyr Asn Thr Pro Asn Leu Leu
            500                 505                 510

Lys Pro Asp Ile Thr Ala Pro Gly Val Ala Ile Leu Ala Ala Trp Pro
```

```
        515                 520                 525

Gly Asn Asp Thr Ser Glu Ala Leu Pro Gly Gln Lys Pro Pro Ile Phe
    530                 535                 540

Asn Leu Leu Ser Gly Thr Ser Met Ser Cys Pro His Val Ser Gly Ile
545                 550                 555                 560

Ala Ala Thr Val Lys Ala Val Asn Pro Ala Trp Ser Pro Ser Ala Val
                565                 570                 575

Lys Ser Ala Ile Met Thr Thr Ala Ile Gln Ile Asn Asn Leu Lys Ala
            580                 585                 590

Pro Ile Thr Thr Val Ser Gly Ser Lys Ala Thr Pro Tyr Asp Ile Gly
        595                 600                 605

Ala Gly Glu Ala Ser Thr Ser Gly Pro Leu Lys Pro Gly Leu Val Tyr
    610                 615                 620

Glu Thr Asp Val Ala Asp Tyr Leu Gln Phe Leu Cys Ser Ala Gly Phe
625                 630                 635                 640

Asn Ile Ser Gln Ile Lys Leu Ile Ser Ser Thr Val Pro Lys Asp Phe
                645                 650                 655

Ser Cys Pro Lys Asn Pro Thr Ser Glu Leu Val Ser Asn Met Asn Tyr
            660                 665                 670

Pro Ser Ile Ala Ile Ser Ser Leu Lys Glu Asn Glu Pro Lys Lys Val
        675                 680                 685

Thr Arg Thr Val Thr Asn Thr Gly Glu Glu Ala Ser Val Tyr Thr Ala
    690                 695                 700

Ile Ile Glu Ala Pro Lys Gly Leu Glu Val Gln Val Ile Pro Ser Lys
705                 710                 715                 720

Leu Glu Phe Asn Tyr Lys Ser Lys Lys Leu Ser Tyr Glu Val Ser Phe
                725                 730                 735

Lys Ala Ser Ser Pro Ser Lys Glu Asp Leu Phe Gly Ser Ile Thr Trp
            740                 745                 750

Thr Asn Gly Lys Tyr Lys Val Arg Ser Pro Phe Val Val Ser Ser Asn
        755                 760                 765


<210> SEQ ID NO 5
<211> LENGTH: 2307
<212> TYPE: DNA
<213> ORGANISM: Nicotiana tabacum

<400> SEQUENCE: 5

atgaaaggcc tttctttgtt cttctgcttt tctcttttca ttgtcgcttt cataagagaa      60

gccgactcag cttctcaagc acaaaacaat ggcatttata ttgtttatat gggtgctgcg     120

gcttcttcta acggtggtac cagacatgat caagcgcagc ttatcagctc cttgatcaga     180

aggaacaaga atgcagtggt acacagctac aacaatggtt tctcaggatt cgcggcacgt     240

ttatcagaag ctgaagctaa atccatggct caaagacctg gagttatctc tgtatttcct     300

gatccagtac tgcaactcca cactacacat tcatgggatt tcttgaagta tcaaactgat     360

gaaaaaatca attcaagtcc aagctctggt tctgattcat cattaattgg agctgatacc     420

ataattggca tattggatac gggtatatgg ccagaatctg agagtttcaa tgacaaggat     480

atgggtccaa ttccagcccg gtggaatgga acttgcatgg atggtcaaga ttttggctct     540

tcaaaatgca acaagaagat agttggtgca agattttatg aggagtctga tgacagtgga     600

ataaaaatcg ctggatcagc cagggacgag aacggacatg gtactcatgt tgcgtctact     660

gcagctggga gtcctgttgc aggtgcatcc tactatggcc tagctgcagg aactgccacg     720
```

```
ggtggatctc ctggttcaag gattgccatg tatcgtgtct gtactacttt tggatgccgt    780

ggatcagcta tcatgaaagc attcgatgac gcaattgcag atggggttga tgttttatca    840

ctatcacttg gttcatcacc cggacttgaa cctgattttc cgagcaatcc tattgccata    900

ggagcatttc atgccgtaga aaagggcatt gttgttgttt gctctgctgg aaatagtggc    960

cctggcccaa aaactgttgt caatacagct ccttggattc taacggttgc agccaccacc   1020

attgatcgtg acttcgagac agatattgtc ttgggtggaa acaagcttat taagggtgga   1080

ggtataaact ttggtaacat gacaaaatcg tcagtctacc ctttgattca tggcaattca   1140

accaaatcaa acaataatgt ttctgaggcg gatgcaagga gttgtgttcc tggttcatta   1200

gatgaaaaca aagtcaaggg gaagattgtt ctttgtgaaa atcttgatga tggcgaatat   1260

tttcccagtg acaagctaga cgaagtgaag agtcgaggtg gagttggatt tatactaata   1320

gatgatgatg aaagaactgt ggcacccaaa ttcaattcct tcccagcagg tgtagtctct   1380

aaaaaggatg gtactgagat ccttgcctac attaactcga ctaggaatcc cattgcatca   1440

attttaccaa ctgtttccat aacaaagtac aaaccagctc cagttgtcgc ttacttctca   1500

tcaagaggcc ctgcgtacaa cacccctaac ctcctcaaac cggatattac agcaccaggg   1560

gttgccattc ttgctgcttg gcctggaaat gacacgagtg aggctctccc cggccaaaaa   1620

ccaccaattt tcaacctact ctcaggcact tccatgtcct gccctcacgt atccggtatt   1680

gctgcaactg tcaaagcagt taaccctgcc tggagtcctt cagctgtcaa atcagctatt   1740

atgaccacag ctattcagat aaacaatttg aaggctccaa tcactacagt ctcaggatcc   1800

aaagcaacac catatgacat aggtgcagga gaagcaagca cttcaggtcc attaaaacca   1860

ggtctagtct acgagacaga tgtcgccgac tacttgcagt tcctatgttc tgctggcttt   1920

aacatatcac agataaagct gatctcaagt acagttccta aggacttttc atgcccaaaa   1980

aacccaacct ctgaattggt ttctaatatg aattatccat caatagctat ttctagtctc   2040

aaagaaaacg agccgaagaa agttactaga acagttacaa atactggtga agaagcatca   2100

gtatatactg caatcattga ggcaccaaaa ggattggaag tccaagtgat tccaagtaaa   2160

ttggaattta attataaaag caagaaatta agctatgaag tgtctttcaa agcttcatct   2220

ccctcaaagg aggatctgtt tggctcaatt acttggacaa atggtaagta caaagtccgg   2280

agtccatttg ttgtaagtag caactaa                                       2307
```

<210> SEQ ID NO 6
<211> LENGTH: 768
<212> TYPE: PRT
<213> ORGANISM: Nicotiana tabacum

<400> SEQUENCE: 6

```
Met Lys Gly Leu Phe Leu Phe Ile Cys Phe Ser Leu Phe Ile Val Ser
1               5                   10                  15

Phe Ile Ile Glu Ala Asp Ser Ala Ser Gln Ser Gln Asn Asn Gly Ile
            20                  25                  30

Tyr Ile Val Tyr Met Gly Ala Ala Ala Ser Ser Asn Gly Gly Thr Arg
        35                  40                  45

His Asp Gln Ala Gln Leu Ile Ser Ser Leu Ile Arg Arg Asn Lys Asn
    50                  55                  60

Ala Val Val His Ser Tyr Lys Asn Gly Phe Ser Gly Phe Ala Ala Arg
65                  70                  75                  80

Leu Ser Glu Ala Glu Ala Lys Ser Met Ala Gln Arg Pro Gly Val Val
                85                  90                  95
```

-continued

```
Ser Val Phe Pro Asp Pro Val Leu Gln Leu His Thr Thr His Ser Trp
            100                 105                 110

Asp Phe Leu Lys Tyr Gln Thr Asp Glu Lys Ile Asn Ser Ser Pro Ser
        115                 120                 125

Ser Gly Ser Asp Ser Ser Leu Ile Gly Ala Asp Thr Ile Ile Gly Ile
    130                 135                 140

Leu Asp Thr Gly Ile Trp Pro Glu Ser Glu Ser Phe Asn Asp Lys Asp
145                 150                 155                 160

Met Gly Pro Ile Pro Ala Arg Trp Asn Gly Thr Cys Met Asp Gly Gln
                165                 170                 175

Asp Phe Gly Ser Ser Asn Cys Asn Lys Lys Ile Val Gly Ala Arg Phe
            180                 185                 190

Tyr Glu Glu Ser Asp Asp Ser Gly Ile Lys Ile Thr Gly Ser Ala Arg
        195                 200                 205

Asp Glu Asn Gly His Gly Thr His Val Ala Ser Thr Ala Ala Gly Ser
    210                 215                 220

Pro Val Ala Gly Ala Ser Tyr Tyr Gly Leu Ala Ala Gly Thr Ala Thr
225                 230                 235                 240

Gly Gly Ser Pro Gly Ser Arg Ile Ala Met Tyr Arg Val Cys Thr Thr
                245                 250                 255

Phe Gly Cys Arg Gly Ser Ala Ile Met Lys Ala Phe Asp Asp Ala Ile
            260                 265                 270

Ala Asp Gly Val Asp Val Leu Ser Leu Ser Leu Gly Ser Ser Pro Gly
        275                 280                 285

Leu Glu Pro Asp Phe Pro Thr Asn Pro Ile Ala Ile Gly Ala Phe His
    290                 295                 300

Ala Val Glu Lys Gly Ile Val Val Val Cys Ser Ala Gly Asn Ser Gly
305                 310                 315                 320

Pro Gly Pro Lys Thr Val Val Asn Thr Ala Pro Trp Ile Leu Thr Val
                325                 330                 335

Ala Ala Thr Thr Ile Asp Arg Asp Phe Glu Thr Asp Val Leu Leu Gly
            340                 345                 350

Gly Asn Lys Leu Ile Lys Gly Gly Gly Ile Asn Phe Gly Asn Met Thr
        355                 360                 365

Lys Ser Thr Val Tyr Pro Leu Ile His Gly Asn Ser Thr Lys Ser Asn
    370                 375                 380

Asp Asn Val Ser Glu Ala Asp Ala Arg Ser Cys Val Pro Gly Ser Leu
385                 390                 395                 400

Asp Glu Asn Lys Val Lys Gly Lys Ile Val Leu Cys Glu Asn Leu Asp
                405                 410                 415

Asp Gly Glu Tyr Phe Pro Ser Asp Lys Leu Asp Glu Val Lys Ser Arg
            420                 425                 430

Gly Gly Val Gly Phe Ile Leu Ile Asp Asp Asp Glu Arg Thr Val Ala
        435                 440                 445

Pro Lys Phe Lys Ala Phe Pro Ala Gly Val Val Ser Lys Lys Asp Gly
    450                 455                 460

Thr Glu Ile Leu Ala Tyr Ile Asn Ser Thr Arg Asn Pro Val Ala Ser
465                 470                 475                 480

Ile Leu Pro Thr Ile Ser Ile Thr Lys Tyr Lys Pro Ala Pro Val Val
                485                 490                 495

Ala Tyr Phe Ser Ser Arg Gly Pro Ala Tyr Asn Thr Pro Asn Leu Leu
            500                 505                 510
```

```
Lys Pro Asp Ile Thr Ala Pro Gly Val Ala Ile Leu Ala Ala Trp Pro
        515                 520                 525

Gly Asn Asp Thr Ser Glu Ala Leu Pro Gly Gln Lys Pro Pro Ile Phe
    530                 535                 540

Asn Leu Leu Ser Gly Thr Ser Met Ser Cys Pro His Val Ser Gly Ile
545                 550                 555                 560

Ala Ala Thr Val Lys Ala Val Asn Pro Thr Trp Ser Pro Ser Ala Val
                565                 570                 575

Lys Ser Ala Ile Met Thr Thr Ala Ile Gln Thr Asn Asn Leu Lys Ala
            580                 585                 590

Pro Ile Thr Thr Val Ser Gly Ser Lys Ala Thr Pro Tyr Asp Ile Gly
        595                 600                 605

Ala Gly Glu Ala Ser Thr Ser Gly Pro Leu Lys Pro Gly Leu Val Tyr
    610                 615                 620

Glu Thr Asp Val Ala Asp Tyr Leu Gln Phe Leu Cys Ser Val Gly Phe
625                 630                 635                 640

Asn Ile Ser Gln Ile Lys Leu Ile Ser Ser Thr Val Pro Lys Asp Phe
                645                 650                 655

Ser Cys Pro Lys Asn Ser Ser Ser Glu Leu Val Ser Asn Met Asn Tyr
            660                 665                 670

Pro Ser Ile Ala Thr Ser Ser Leu Lys Glu Asn Glu Pro Lys Lys Val
        675                 680                 685

Thr Arg Thr Val Thr Asn Thr Gly Glu Glu Ala Ser Val Tyr Thr Ala
    690                 695                 700

Ile Ile Glu Ala Pro Lys Gly Leu Glu Val Gln Val Ile Pro Thr Lys
705                 710                 715                 720

Leu Glu Phe Thr Asn Lys Arg Lys Lys Val Ser Tyr Asp Val Ser Phe
                725                 730                 735

Lys Ala Ser Ser Thr Ser Lys Glu Asp Leu Phe Gly Ser Ile Thr Trp
            740                 745                 750

Thr Asn Gly Lys Tyr Lys Val Arg Ser Pro Phe Val Val Ser Ser Asn
        755                 760                 765


<210> SEQ ID NO 7
<211> LENGTH: 2307
<212> TYPE: DNA
<213> ORGANISM: Nicotiana tabacum

<400> SEQUENCE: 7

atgaaaggcc tttttttgtt catatgcttc tctcttttca ttgtctcttt cataatagaa      60

gccgactcag cttctcaatc acaaaacaat ggcatttata ttgtttatat gggtgctgcg     120

gcttcatcta acggtggtac cagacatgat caagcgcagc ttatcagctc cttgatcaga     180

aggaacaaga atgcagtggt acacagctac aagaatggtt tctcaggatt tgcggcacgt     240

ttatcagaag ctgaagctaa atcgatggct caaagacctg gagttgtctc tgtatttcct     300

gatccagtac tgcaactcca cactacacat tcatgggatt tcttgaagta tcaaactgat     360

gaaaaaatca attcaagtcc aagctctggt tctgattcat cattaattgg agctgatacc     420

ataattggaa tcttggatac gggtatatgg ccagaatcag agagtttcaa tgacaaggat     480

atgggtccaa ttccagcccg gtggaatgga acttgcatgg atggtcaaga ttttggctct     540

tccaattgca acaagaagat agttggtgca agattttatg aggagtctga tgacagtgga     600

ataaaaatca ctggatcagc cagggacgag aacggacatg gtactcacgt tgcatccact     660

gcagctggga gccctgttgc aggtgcatcc tactatggcc tagctgcagg gactgcaaca     720
```

```
ggtggatctc cgggttccag gatcgccatg tatcgtgtct gtactacttt tggatgccgt    780

ggatcagcta tcatgaaagc attcgatgat gcaattgcag atggggttga tgttttatct    840

ctatcactcg gttcatcacc tggacttgaa cctgattttc caaccaatcc tattgccata    900

ggagcatttc atgccgtaga aaagggcatt gttgttgttt gctctgctgg aaatagtggc    960

cctggcccaa aaactgttgt caatacagct ccttggattc ttactgttgc agccaccacc   1020

attgatcgtg acttcgagac agatgttctc ttgggtggaa acaagttgat taagggtgga   1080

ggtataaact ttggtaacat gacaaaatca acagtctacc ccttgattca tggcaattca   1140

accaaatcaa acgataatgt ttctgaggca gatgcaagga gttgtgttcc tggttcatta   1200

gatgaaaaca aagtcaaggg gaagattgtt ctttgtgaaa atcttgatga tggcgaatat   1260

tttcccagtg acaagctaga cgaagtgaag agtcgaggtg gagttggatt tatactaata   1320

gatgatgatg aaagaactgt ggcacctaaa ttcaaagcct tcccagcggg tgtagtctct   1380

aaaaaggatg gtactgagat cctcgcctac attaactcga caaggaatcc agttgcatca   1440

attttgccaa ctatttccat aacaaagtac aaaccagctc cagttgttgc ttacttctca   1500

tcaagaggtc ctgcatacaa tacacctaac ctcctcaaac cagatattac agcaccaggg   1560

gttgccattc ttgctgcttg gcctggaaat gacacgagtg aggctctccc cggccaaaaa   1620

ccaccaattt tcaacctact ctcaggcact tccatgtcct gccctcacgt ttctggcatt   1680

gctgcaacgg tcaaagcagt gaacccaacc tggagtcctt cagctgtcaa atcagctatt   1740

atgaccacag ctattcagac aaacaatttg aaggctccaa tcactacagt ctcaggatcc   1800

aaagcaacac catatgacat aggagcagga gaagcaagca cttcaggtcc attaaaacca   1860

ggtctagtct acgagacaga tgtcgccgac tacttgcagt tcctctgttc tgttggcttt   1920

aacatatcac agataaagct gatctcaagt acagttccta aggacttttc atgcccaaaa   1980

aactcaagct ctgaattggt ttctaacatg aattatcctt caatagctac ttctagtctc   2040

aaagaaaacg agcccaagaa agttactaga actgttacaa atactggtga agaagcatca   2100

gtatatactg caattattga ggcaccaaaa ggattggaag tccaagtgat tccaactaaa   2160

ttggaattta caaataaaag gaagaaagta agctatgatg tatctttcaa agcctcatct   2220

acctcaaagg aagatctgtt tggatcaatt acttggacaa atggtaagta caaagtccgg   2280

agtccatttg tcgtaagtag caactaa                                       2307
```

```
<210> SEQ ID NO 8
<211> LENGTH: 783
<212> TYPE: PRT
<213> ORGANISM: Solanum lycopersicum

<400> SEQUENCE: 8

Met Arg Asp Ile Val Leu Phe Phe Cys Phe Leu Leu Phe Leu Leu Ser
1               5                   10                  15

Leu Leu Arg Glu Thr Asn Ala Val Ser Gln Glu Lys Asn Asn Gly Val
            20                  25                  30

Tyr Ile Val Tyr Met Gly Ala Ala Asp Ser Ser Asn Asp Gly Thr Lys
        35                  40                  45

Asn Gln Gln Ala Glu Leu Met Ser Ser Leu Ile Lys Arg Lys Lys Asp
    50                  55                  60

Ala Val Val His Ser Tyr Asn Asn Gly Phe Ser Gly Phe Ala Ala Arg
65                  70                  75                  80

Leu Ser Glu Ala Glu Ala Lys Ser Ile Ala Gln Lys Pro Gly Val Ile
```

```
                85                  90                  95

Ser Val Phe Pro Asp Pro Ile Leu Gln Leu His Thr Thr Arg Ser Trp
            100                 105                 110

Asp Phe Leu Gln Tyr Gln Thr Glu Val Glu Ser Ser Ser Gly Pro Ile
        115                 120                 125

Ser Gly Ser Asp Asn Ala Ser Pro Lys Gly Val Asp Thr Ile Ile Gly
    130                 135                 140

Ile Leu Asp Thr Gly Ile Trp Pro Glu Ser Glu Ser Phe Ser Asp Asn
145                 150                 155                 160

Asp Met Ser Glu Val Pro Ser Lys Trp Lys Gly Thr Cys Met Gly Ser
                165                 170                 175

His Asp Ser Ile Ser Phe Lys Cys Asn Lys Lys Leu Val Gly Ala Arg
            180                 185                 190

Phe Tyr Asp Asp Ser Asp Glu Asp Gly Val Arg Pro Phe Gly Ser Ala
        195                 200                 205

Arg Asp Asp Asn Gly His Gly Thr His Val Ala Ser Thr Ala Ala Gly
    210                 215                 220

Ser Leu Ile Ser Gly Ala Ser Tyr Tyr Gly Leu Ala Ser Gly Thr Ala
225                 230                 235                 240

Lys Gly Gly Ser Pro Gly Ser Arg Ile Ala Met Tyr Arg Val Cys Thr
                245                 250                 255

Ala Asp Gly Cys His Gly Ser Ala Ile Met Lys Ala Phe Asp Asp Ala
            260                 265                 270

Ile Ala Asp Gly Val Asp Val Leu Ser Leu Ser Leu Gly Ser Ser Ser
        275                 280                 285

Gly Leu Glu Val Glu Phe Ser Arg Asp Pro Ile Ala Ile Gly Ala Phe
    290                 295                 300

His Ala Val Glu Lys Gly Ile Leu Val Ser Cys Ser Ala Gly Asn Asp
305                 310                 315                 320

Gly Pro Gly Pro Ala Thr Val Val Asn Val Ala Pro Trp Ile Leu Thr
                325                 330                 335

Val Ala Ala Thr Thr Ile Asp Arg Asp Phe Glu Thr Asp Ile Val Leu
            340                 345                 350

Gly Gly Asn Lys Leu Ile Lys Gly Gly Gly Ile Ser Leu Gly Asn Leu
        355                 360                 365

Thr Arg Ser Pro Val Tyr Pro Leu Ile Ser Gly Asp Leu Ala Lys Ser
    370                 375                 380

Ser Asn Asn Val Val Met Glu Lys Gly Ala Arg Tyr Cys Tyr Pro Asn
385                 390                 395                 400

Ser Leu Asp Glu Thr Lys Val Lys Gly Lys Ile Val Leu Cys Asp Asn
                405                 410                 415

Arg Asp Gly Tyr Phe Ser Leu Thr Glu Lys Leu Thr Glu Val Lys Lys
            420                 425                 430

Lys Gly Gly Ile Gly Phe Ile Leu Ile Asp Asp Asn Ala Arg Thr Val
        435                 440                 445

Ala Pro Lys Phe Asn Ser Phe Pro Ala Ala Val Val Thr Glu Lys Asp
    450                 455                 460

Ser Asn Glu Ile Leu Ser Tyr Ile Asn Ser Thr Lys Lys Pro Val Ala
465                 470                 475                 480

Ser Val Leu Pro Thr Val Thr Ile Ala Asn Tyr Lys Pro Ala Pro Leu
                485                 490                 495

Val Ala Tyr Phe Ser Ser Arg Gly Pro Thr Tyr Asn Thr His Asn Leu
            500                 505                 510
```

```
Leu Lys Pro Asp Ile Thr Ala Pro Gly Val Ala Ile Leu Ala Ala Trp
        515                 520                 525

Pro Gly Asn Asp Thr Thr Glu Ala Val Ala Gly Gln Ala Leu Pro Leu
    530                 535                 540

Tyr Asn Ile Ile Ser Gly Thr Ser Met Ser Cys Pro His Val Ser Gly
545                 550                 555                 560

Ile Ala Ala Leu Val Lys Ala Gln Asn Pro Ser Trp Ser Pro Ser Ala
                565                 570                 575

Ile Arg Ser Ala Ile Met Thr Ser Ala Leu Gln Thr Asn Asn Leu Lys
            580                 585                 590

Ala Pro Ile Thr Thr Val Ser Gly Ser Val Ala Thr Pro Tyr Asp Ile
        595                 600                 605

Gly Ala Gly Glu Ala Ser Pro Ser Leu Ala Leu Asn Pro Gly Leu Val
    610                 615                 620

Tyr Glu Thr Asn Thr Ala Asp Tyr Leu Gln Tyr Leu Cys Ser Val Gly
625                 630                 635                 640

Tyr Asp Lys Ser Lys Ile Lys Leu Ile Ser Asn Thr Val Pro Asp Asp
                645                 650                 655

Phe Ser Cys Pro Thr Asn Ser Ser Ser Glu Ser Val Ser Gln Met Asn
            660                 665                 670

Tyr Pro Ser Ile Ala Val Ser Asn Ile Lys Glu Asn Glu Ile Lys Lys
        675                 680                 685

Val Thr Arg Thr Val Thr Asn Val Gly Gln Asp Asp Ala Thr Tyr Thr
    690                 695                 700

Ala Ser Ile Lys Ala Pro Val Gly Leu Glu Val Gln Val Thr Pro Asn
705                 710                 715                 720

Lys Leu Val Phe Thr Asn Asn Ser Lys Lys Leu Ser Tyr Glu Met Ser
                725                 730                 735

Phe Lys Ala Ser Ser Lys Pro Lys Glu Asp Leu Phe Gly Ser Ile Thr
            740                 745                 750

Trp Thr Asn Gly Lys Tyr Lys Val Arg Ser Pro Phe Val Ile Ser Thr
        755                 760                 765

Asn Ser Gln Gly Glu His Ser Lys Thr Ala Asp Arg Arg Ser Asn
    770                 775                 780
```

<210> SEQ ID NO 9
<211> LENGTH: 2352
<212> TYPE: DNA
<213> ORGANISM: Solanum lycopersicum

<400> SEQUENCE: 9

```
atgagagaca ttgttctgtt tttttgcttc cttttatttt tactctcttt gcttagagaa      60

actaatgcag tttctcaaga aaaaaacaat ggtgtttata ttgtttacat gggtgctgct     120

gattcgtcga acgatggcac gaaaaatcag caagcagaac taatgagctc attgataaaa     180

aggaaaaagg atgcagttgt acacagttac aacaatggtt tctcaggatt cgcagcgcgt     240

ttatcagaag ctgaggctaa atctattgct caaaaacctg gagttatatc agtattccct     300

gatccaatat tgcaactaca cacaacgcgt tcgtgggact tttgcaata tcaaactgaa      360

gtagaaagca gttctggtcc aatatctggt tctgataacg cgtcaccaaa aggcgttgat     420

actataattg gaatcctgga tacaggaata tggcctgaat cagagagttt tagtgataat     480

gatatgagtg aagttccatc taagtggaaa ggaacttgta tgggaagtca tgattccatc     540

tctttcaaat gcaacaagaa gttagttggt gcaaggttct atgatgactc tgatgaggat     600
```

```
ggtgtaagac cttttggttc agctagggat gataatggac atggaactca tgttgcatct    660
acagcagctg ggagtttgat ttcaggagca tcttattatg gtttggcttc tgggacagca    720
aagggtggat ccccgggttc aagaatagcc atgtatcgtg tctgcacggc tgatggatgt    780
cacggatcag ctataatgaa agcatttgat gatgcaattg cagatggggt tgatgtttta    840
tcgctatcac ttggttcatc atctggtctt gaagtcgagt tttctagaga tcctatagct    900
attggagcat tccatgctgt tgaaaaggga attcttgttt cctgttctgc tggaaatgat    960
ggccctggtc cggcaactgt tgtcaatgtt gcaccttgga ttctcactgt tgcagctact   1020
acaattgacc gtgacttcga gacagatatt gtcttaggtg gaaacaagtt gataaaggga   1080
ggaggtataa gtttaggtaa cttgacaaga tctccagtat acccgttgat tagtggcgat   1140
ttagccaaat ccagcaataa tgttgttatg gagaaaggtg caaggtattg ttatccgaat   1200
tcattagatg aaaccaaagt taaggggaaa attgttctct gtgataatcg cgacggatac   1260
ttttcactta ctgagaaact aacagaagtg aagaagaaag gtggcattgg atttatacta   1320
atagatgata atgcaagaac tgtggcccca aaattcaatt cctttccagc agctgttgta   1380
actgaaaagg atagcaatga gatcctttct tacatcaact caacaaagaa accagttgca   1440
tcagttctgc caactgttac catagctaac tacaaaccag ctcctcttgt ggcttacttc   1500
tcatcaaggg gtcctacata caacacacat aatctcctca aaccagatat tacagcacca   1560
ggtgttgcaa ttctcgcggc ttggcctgga aacgacacaa cagaggctgt cgctggccag   1620
gcgttaccac tttacaacat aatatcaggg acttccatgt cctgccctca tgtttctggt   1680
attgccgcgt tagtcaaggc gcaaaatcct tcttggagtc cttcagcaat cagatcagct   1740
attatgacct cagctttaca gactaacaat ttgaaggctc caatcacaac agtctctgga   1800
tccgttgcaa caccatacga cataggagct ggagaagcaa gcccttcatt ggcacttaat   1860
ccaggattgg tctacgagac taacaccgca gactacttgc agtacctatg ctcagttggc   1920
tacgataaat caaagataaa actcatttca aatacagttc ctgatgattt ttcatgtccc   1980
accaactcaa gttctgaatc cgtctcacaa atgaactacc cttccattgc tgtttcaaat   2040
atcaaagaaa atgaaatcaa gaaagtaaca agaactgtaa ctaacgtagg acaagacgac   2100
gcaacataca cagcaagtat aaaggcacca gttggtttgg aagtccaagt gaccccgaat   2160
aaattggtat ttacaaataa tagcaagaag ttgagctatg aaatgtcttt caaagcttca   2220
tctaaaccaa aggaagactt gtttggatca attacatgga caaatggtaa atacaaagtc   2280
cgaagtccat tcgttatatc tactaattca caaggtgaac actccaaaac agcagatcgc   2340
agatcaaact ag                                                        2352
```

```
<210> SEQ ID NO 10
<211> LENGTH: 773
<212> TYPE: PRT
<213> ORGANISM: Solanum tuberosum

<400> SEQUENCE: 10

Met Lys Val Ile Val Leu Phe Phe Cys Phe Phe Leu Leu Leu Leu Ser
1               5                   10                  15

Phe Leu Arg Glu Thr Asn Ala Val Ser Gln Glu Lys Asn Asn Gly Val
            20                  25                  30

Tyr Ile Val Tyr Met Gly Ala Ala Asp Ser Ser Asn Asp Gly Thr Lys
        35                  40                  45

Asn Gln Arg Ala Glu Leu Met Ser Ser Leu Ile Arg Arg Lys Lys Asp
```

-continued

```
    50                  55                  60

Ala Val Val His Ser Tyr Ser Asn Gly Phe Ser Gly Phe Ala Ala Arg
65                  70                  75                  80

Leu Ser Glu Ala Glu Ala Lys Ser Ile Ala Gln Lys Pro Gly Val Ile
                85                  90                  95

Ser Val Phe Pro Asp Pro Ile Leu Gln Leu His Thr Thr Arg Ser Trp
            100                 105                 110

Asp Phe Leu Gln Tyr Gln Thr Glu Val Glu Ser Ser Ser Gly Pro Ile
        115                 120                 125

Ser Gly Ser Asp Asn Ala Ser Pro Lys Gly Val Asp Thr Ile Ile Gly
    130                 135                 140

Ile Leu Asp Thr Gly Ile Trp Pro Glu Ser Glu Ser Phe Ser Asp Asn
145                 150                 155                 160

Asp Met Ser Glu Val Pro Ser Lys Trp Lys Gly Thr Cys Met Ala Ser
                165                 170                 175

His Asp Ser Ile Ser Phe Lys Cys Asn Lys Lys Leu Val Gly Ala Arg
            180                 185                 190

Phe Tyr Asp Asp Ser Asp Glu Asp Gly Val Arg Pro Ser Gly Ser Ala
        195                 200                 205

Arg Asp Glu Asn Gly His Gly Thr His Val Ala Ser Thr Ala Ala Gly
    210                 215                 220

Ser Pro Ile Ser Gly Ala Ser Tyr Tyr Gly Leu Ala Ser Gly Thr Ala
225                 230                 235                 240

Lys Gly Gly Ser Pro Gly Ser Arg Ile Ala Met Tyr Arg Val Cys Met
                245                 250                 255

Thr Asp Gly Cys His Gly Ser Ala Ile Met Lys Ala Phe Asp Asp Ala
            260                 265                 270

Ile Ala Asp Gly Val Asp Val Leu Ser Leu Ser Leu Gly Ser Ser Ser
        275                 280                 285

Gly Leu Glu Val Glu Phe Ser Ser Asp Pro Ile Ala Ile Gly Ala Phe
    290                 295                 300

His Ala Val Glu Lys Gly Ile Leu Val Ser Cys Ser Ala Gly Asn Asp
305                 310                 315                 320

Gly Pro Gly Pro Ala Thr Val Val Asn Val Ala Pro Trp Ile Leu Thr
                325                 330                 335

Val Ala Ala Thr Thr Ile Asp Arg Asp Phe Glu Thr Asp Ile Val Leu
            340                 345                 350

Gly Gly Asn Lys Leu Ile Lys Gly Gly Gly Ile Ser Leu Gly Asn Leu
        355                 360                 365

Thr Arg Ser Pro Val Tyr Pro Leu Ile Ser Gly Asp Leu Ala Lys Ser
    370                 375                 380

Gly Asn Thr Val Val Ser Glu Lys Asn Ala Arg Phe Cys Asn Pro Asn
385                 390                 395                 400

Ser Leu Asp Gly Thr Lys Val Lys Gly Lys Val Val Leu Cys Asp Asn
                405                 410                 415

Arg Asp Gly Tyr Tyr Ser Leu Thr Glu Lys Leu Thr Glu Val Lys Ser
            420                 425                 430

Lys Gly Gly Ile Gly Phe Ile Val Val Asp Asp Asn Ala Arg Thr Val
        435                 440                 445

Ala Pro Lys Phe Lys Ser Phe Pro Ala Ala Val Val Thr Glu Lys Asp
    450                 455                 460

Ser Asn Glu Ile Leu Ser Tyr Ile Asn Ser Thr Lys Lys Pro Val Ala
465                 470                 475                 480
```

```
Ser Val Leu Pro Thr Val Thr Ile Ala Asn Tyr Lys Pro Ala Pro Leu
                485                 490                 495

Val Ala Tyr Phe Ser Ser Arg Gly Pro Thr Tyr Asn Thr His Asn Leu
            500                 505                 510

Leu Lys Pro Asp Ile Thr Ala Pro Gly Val Ala Ile Leu Ala Ala Trp
        515                 520                 525

Pro Gly Asn Asp Thr Asn Glu Ala Val Ala Gly Gln Ala Pro Pro Leu
    530                 535                 540

Tyr Asn Ile Ile Ser Gly Thr Ser Met Ser Cys Pro His Val Ser Gly
545                 550                 555                 560

Ile Ala Ala Leu Val Lys Ala Gln Asn Pro Ser Trp Ser Pro Ser Ala
                565                 570                 575

Ile Lys Ser Ala Ile Met Thr Ser Ala Leu Gln Thr Asn Asn Leu Lys
            580                 585                 590

Ala Pro Ile Thr Thr Val Ser Gly Ser Val Ala Thr Pro Tyr Asp Ile
        595                 600                 605

Gly Ala Gly Glu Ala Ser Pro Ser Leu Ala Leu Asn Pro Gly Leu Val
    610                 615                 620

Tyr Glu Thr Asn Thr Ala Asp Tyr Leu Gln Tyr Leu Cys Ser Val Gly
625                 630                 635                 640

Tyr Asp Lys Ser Lys Ile Lys Leu Ile Ser Asn Thr Val Pro Asn Asp
                645                 650                 655

Phe Ser Cys Pro Thr Asn Ser Ser Ser Glu Ser Val Ser Gln Met Asn
            660                 665                 670

Tyr Pro Ser Ile Ala Val Ser Asn Ile Lys Glu Asn Glu Ile Lys Lys
        675                 680                 685

Val Thr Arg Thr Val Thr Asn Val Gly Gln Glu Asp Ala Thr Tyr Thr
    690                 695                 700

Ala Ser Ile Lys Ala Pro Val Gly Leu Glu Val Gln Val Thr Pro Asn
705                 710                 715                 720

Lys Leu Val Phe Thr Asn Asn Ser Lys Lys Leu Ser Tyr Glu Val Ser
                725                 730                 735

Phe Lys Ala Ser Ser Lys Pro Lys Glu Asp Leu Phe Gly Ser Ile Thr
            740                 745                 750

Trp Thr Asn Gly Lys Tyr Lys Val Arg Ser Pro Phe Val Val Ser Thr
        755                 760                 765

Asn Ser Gln Gly Val
    770
```

<210> SEQ ID NO 11
<211> LENGTH: 2322
<212> TYPE: DNA
<213> ORGANISM: Solanum tuberosum

<400> SEQUENCE: 11

```
atgaaagtca ttgttctgtt tttttgcttc tttttattat tactctcttt tcttagagaa     60

actaatgcag tttctcaaga aaaaaacaat ggtgtataca ttgtttacat gggcgctgct    120

gattcgtcga acgatggcac gaaaaatcag cgagcagaac ttatgagctc tttgataaga    180

agaaaaaagg atgcagttgt acacagttac agcaatggtt tctcaggatt cgcagcgcgt    240

ttatcagaag ctgaggctaa atccattgct caaaaacctg gagttatatc agtattccct    300

gatccaatat tgcaactcca cacaacgcgt tcgtgggact tttgcaata tcaaactgaa    360

gtagaaagca gttctggtcc aatatcaggt tctgataacg cgtcaccaaa aggcgttgat    420
```

```
actataattg gaatcttgga tacaggaata tggcctgaat cagagagttt tagtgataat    480
gatatgagtg aagttccatc taagtggaaa ggaacttgta tggcaagtca tgattccatc    540
tctttcaaat gcaacaagaa gttagttggt gcaaggttct atgatgactc tgatgaggat    600
ggtgtaagac cttctggttc agctagggat gagaatggac atggaactca tgttgcatct    660
acagcagctg ggagtccgat ttcaggagca tcttattatg gtttggcttc tgggaccgcg    720
aagggtggat ccccgggttc aagaatagcc atgtatcgtg tctgcatgac tgatggatgt    780
cacggatcag ctataatgaa agcatttgat gatgcaattg cagatggggt tgatgtttta    840
tcgctatcac ttggttcatc atctggtctt gaagttgagt tttcgagtga tcctatagct    900
attggagcat tccatgctgt tgaaaaggga attcttgttt cctgttctgc tggaaatgat    960
ggccctggtc cggcaactgt tgtcaacgtc gcgccttgga ttctcacagt tgcagctact   1020
acaattgacc gtgacttcga gacagatatt gtcttaggtg gaaacaagtt gattaagggt   1080
ggaggtataa gtcttggtaa tttgacaaga tctccagtat acccgttgat tagtggcgat   1140
ttagccaagt ccggcaatac tgttgtttcg gagaaaaatg caaggttttg taatccgaat   1200
tcattagatg gaaccaaagt taaggggaaa gttgttcttt gtgataatcg cgacggatac   1260
tattcactta ctgagaaact aacagaagtg aagagcaaag gtggcattgg atttatagta   1320
gtagatgata atgcaagaac tgtggcacct aaattcaaat cctttccagc agctgttgta   1380
actgaaaagg atagcaatga gatcctttct tacatcaact caacaaagaa accagttgca   1440
tcagttctgc caactgttac catagctaac tacaaaccag ctcctcttgt ggcttacttc   1500
tcatcaaggg gtcctacata caacacacat aatctcctca aaccagatat tacagcacca   1560
ggtgttgcaa ttctcgcggc ttggcctgga aacgacacaa acgaggctgt cgctggccag   1620
gcgccaccac tttacaacat aatatcaggg acttccatgt cctgccctca tgtttctggt   1680
attgccgcat tagtcaaggc gcaaaatcct tcttggagtc cttcagcaat caaatcagct   1740
atcatgacct cagctttaca gactaacaat ttgaaggctc caatcacaac agtctccggc   1800
tccgttgcaa caccatacga cataggagct ggagaagcaa gcccttcatt ggcacttaat   1860
ccaggattgg tctacgagac taacactgca gactacttgc agtacctatg ctcagttggc   1920
tacgataaat caaagataaa actcatctca aatactgttc ctaatgattt ttcatgtccc   1980
accaactcaa gttctgaatc cgtctcacaa atgaactacc cttccattgc tgtttcaaat   2040
atcaaagaaa atgaaatcaa gaaagtaaca agaactgtaa ctaacgtagg acaagaagac   2100
gcaacataca cagcaagtat aaaagcacca gttggtttgg aagtccaagt gaccccgaat   2160
aaattggtat ttacaaataa tagcaagaag ttgagctatg aagtgtcttt caaagcttca   2220
tctaaaccaa aggaagactt gtttggatca attacatgga caaatggtaa atacaaagtc   2280
cgaagtccat tcgttgtatc tactaattca caaggtgtct ga                      2322

<210> SEQ ID NO 12
<211> LENGTH: 769
<212> TYPE: PRT
<213> ORGANISM: Arabidopsis thaliana

<400> SEQUENCE: 12

Met Lys Gly Ile Thr Phe Phe Thr Pro Phe Leu Ser Phe Leu Tyr Leu
1               5                   10                  15

Leu Cys Ile Leu Phe Met Thr Glu Thr Glu Ala Gly Ser Arg Asn Gly
            20                  25                  30
```

```
Asp Gly Val Tyr Ile Val Tyr Met Gly Ser Ala Ser Ser Ala Ala Asn
        35                  40                  45

Ala Asn Arg Ala Gln Ile Leu Ile Asn Thr Met Phe Lys Arg Arg Ala
    50                  55                  60

Asn Asp Leu Leu His Thr Tyr Lys His Gly Phe Ser Gly Phe Ala Ala
65                  70                  75                  80

Arg Leu Thr Ala Glu Glu Ala Lys Val Ile Ala Lys Lys Pro Gly Val
                85                  90                  95

Val Ser Val Phe Pro Asp Pro His Phe Gln Leu His Thr Thr His Ser
            100                 105                 110

Trp Asp Phe Leu Lys Tyr Gln Thr Ser Val Lys Val Asp Ser Gly Pro
        115                 120                 125

Pro Ser Ser Ala Ser Asp Gly Ser Tyr Asp Ser Ile Val Gly Ile Leu
    130                 135                 140

Asp Thr Gly Ile Trp Pro Glu Ser Glu Ser Phe Asn Asp Lys Asp Met
145                 150                 155                 160

Gly Pro Ile Pro Ser Arg Trp Lys Gly Thr Cys Met Glu Ala Lys Asp
                165                 170                 175

Phe Lys Ser Ser Asn Cys Asn Arg Lys Ile Ile Gly Ala Arg Tyr Tyr
            180                 185                 190

Lys Asn Pro Asp Asp Asp Ser Glu Tyr Tyr Thr Thr Arg Asp Val Ile
        195                 200                 205

Gly His Gly Ser His Val Ser Ser Thr Ile Ala Gly Ser Ala Val Glu
    210                 215                 220

Asn Ala Ser Tyr Tyr Gly Val Ala Ser Gly Thr Ala Lys Gly Gly Ser
225                 230                 235                 240

Gln Asn Ala Arg Ile Ala Met Tyr Lys Val Cys Asn Pro Gly Gly Cys
                245                 250                 255

Thr Gly Ser Ser Ile Leu Ala Ala Phe Asp Asp Ala Ile Ala Asp Gly
            260                 265                 270

Val Asp Val Leu Ser Leu Ser Leu Gly Ala Pro Ala Tyr Ala Arg Ile
        275                 280                 285

Asp Leu Asn Thr Asp Pro Ile Ala Ile Gly Ala Phe His Ala Val Glu
    290                 295                 300

Gln Gly Ile Leu Val Ile Cys Ser Ala Gly Asn Asp Gly Pro Asp Gly
305                 310                 315                 320

Gly Thr Val Thr Asn Thr Ala Pro Trp Ile Met Thr Val Ala Ala Asn
                325                 330                 335

Thr Ile Asp Arg Asp Phe Glu Ser Asp Val Val Leu Gly Gly Asn Lys
            340                 345                 350

Val Ile Lys Gly Glu Gly Ile His Phe Ser Asn Val Ser Lys Ser Pro
        355                 360                 365

Val Tyr Pro Leu Ile His Gly Lys Ser Ala Lys Ser Ala Asp Ala Ser
    370                 375                 380

Glu Gly Ser Ala Arg Ala Cys Asp Ser Asp Ser Leu Asp Gln Glu Lys
385                 390                 395                 400

Val Lys Gly Lys Ile Val Leu Cys Glu Asn Val Gly Gly Ser Tyr Tyr
                405                 410                 415

Ala Ser Ser Ala Arg Asp Glu Val Lys Ser Lys Gly Gly Thr Gly Cys
            420                 425                 430

Val Phe Val Asp Asp Arg Thr Arg Ala Val Ala Ser Ala Tyr Gly Ser
        435                 440                 445

Phe Pro Thr Thr Val Ile Asp Ser Lys Glu Ala Ala Glu Ile Phe Ser
```

```
    450                 455                 460

Tyr Leu Asn Ser Thr Lys Asp Pro Val Ala Thr Ile Leu Pro Thr Ala
465                 470                 475                 480

Thr Val Glu Lys Phe Thr Pro Ala Pro Ala Val Ala Tyr Phe Ser Ser
                485                 490                 495

Arg Gly Pro Ser Ser Leu Thr Arg Ser Ile Leu Lys Pro Asp Ile Thr
            500                 505                 510

Ala Pro Gly Val Ser Ile Leu Ala Ala Trp Thr Gly Asn Asp Ser Ser
        515                 520                 525

Ile Ser Leu Glu Gly Lys Pro Ala Ser Gln Tyr Asn Val Ile Ser Gly
    530                 535                 540

Thr Ser Met Ala Ala Pro His Val Ser Ala Val Ala Ser Leu Ile Lys
545                 550                 555                 560

Ser Gln His Pro Thr Trp Gly Pro Ser Ala Ile Arg Ser Ala Ile Met
                565                 570                 575

Thr Thr Ala Thr Gln Thr Asn Asn Asp Lys Gly Leu Ile Thr Thr Glu
            580                 585                 590

Thr Gly Ala Thr Ala Thr Pro Tyr Asp Ser Gly Ala Gly Glu Leu Ser
        595                 600                 605

Ser Thr Ala Ser Met Gln Pro Gly Leu Val Tyr Glu Thr Thr Glu Thr
    610                 615                 620

Asp Tyr Leu Asn Phe Leu Cys Tyr Tyr Gly Tyr Asn Val Thr Thr Ile
625                 630                 635                 640

Lys Ala Met Ser Lys Ala Phe Pro Glu Asn Phe Thr Cys Pro Ala Asp
                645                 650                 655

Ser Asn Leu Asp Leu Ile Ser Thr Ile Asn Tyr Pro Ser Ile Gly Ile
            660                 665                 670

Ser Gly Phe Lys Gly Asn Gly Ser Lys Thr Val Thr Arg Thr Val Thr
        675                 680                 685

Asn Val Gly Glu Asp Gly Glu Ala Val Tyr Thr Val Ser Val Glu Thr
    690                 695                 700

Pro Pro Gly Phe Asn Ile Gln Val Thr Pro Glu Lys Leu Gln Phe Thr
705                 710                 715                 720

Lys Asp Gly Glu Lys Leu Thr Tyr Gln Val Ile Val Ser Ala Thr Ala
                725                 730                 735

Ser Leu Lys Gln Asp Val Phe Gly Ala Leu Thr Trp Ser Asn Ala Lys
            740                 745                 750

Tyr Lys Val Arg Ser Pro Ile Val Ile Ser Ser Glu Ser Ser Arg Thr
        755                 760                 765

Asn
```

<210> SEQ ID NO 13
<211> LENGTH: 2310
<212> TYPE: DNA
<213> ORGANISM: Arabidopsis thaliana

<400> SEQUENCE: 13

```
atgaaaggca ttacattctt cacacccttt ttatcatttc tatatctctt atgcatcttg     60

tttatgacag aaactgaagc tggtcgagaa aatggtgatg gggtctacat tgtctacatg    120

ggatcagctt cctctgctgc aaacgctaat agagctcaaa tactcataaa caccatgttt    180

aaaaggagag caaacgatct tctccacaca tataagcatg gcttctcagg ttttgcagct    240

cgtttgacag cagaagaggc caaggtcata gccaagaaac cgggagtggt ttcagttttt    300
```

```
cctgacccac acttccagct tcatacaact cattcatggg actttctcaa gtaccaaaca    360
tcagtaaagg tcgattccgg tccaccttca tcagcctcag atggatcata tgatagcatt    420
gtcggaattc ttgacacagg gatatggcca gagtcagaga gtttcaatga caaagacatg    480
ggtccaattc cgtctcggtg gaaaggtaca tgcatggaag caaaggactt caagtcttcc    540
aactgtaaca gaaagatcat tggagcaaga tactacaaaa atcctgatga tgattcagaa    600
tactatacca caagggatgt catcggtcac ggttctcatg tgtcctccac catagctgga    660
tctgccgtgg agaatgcttc ctactatggt gtagcttccg ggactgcaaa gggaggttca    720
caaaacgcta gaatcgctat gtacaaagta tgcaatccag gggatgcac tggctcctct     780
atcttagctg ctttcgatga tgcaatcgca gatggagttg atgttctatc tctgtctctt    840
ggagctccag catacgctcg catcgacttg aacactgatc ctattgccat tggagcgttt    900
cacgcggtgg agcaaggaat cttggtgatc tgctctgcgg gtaatgatgg acctgatggc    960
ggtacagtta ctaatactgc accttggata atgaccgttg ctgccaacac tattgataga   1020
gactttgagt ctgatgttgt actaggcggc aataaagtca tcaagggtga aggtatacac   1080
ttttcaaacg ttagtaaatc tcctgtgtat cctctgattc atggcaagtc tgctaagagc   1140
gctgatgcat cagaaggatc agccagggcc tgtgactctg attctctaga tcaagagaag   1200
gtaaaaggga agattgtgtt atgcgagaac gttggtggat catattatgc atcatccgct   1260
agggacgagg tgaagagcaa aggaggtact ggttgcgtct ttgtagatga cagaactaga   1320
gcagttgcta gtgcttatgg tagctttcct actaccgtaa ttgactcaaa ggaagcagct   1380
gagatcttct cctacctcaa ctcaaccaaa gatcctgttg caacaattct tcccactgca   1440
acagttgaaa agttcacacc tgcccctgct gttgcatatt tttcttccag aggaccttca   1500
agcctcacaa gaagcattct caaacctgac attaccgcac caggagtctc gatactcgct   1560
gcatggactg gaaacgactc aagcatttca ctggaaggca agccggcttc tcagtataac   1620
gtcatatcag gaacttccat ggcagctcct catgtttcag ctgttgcatc tctgatcaaa   1680
tcacagcatc ccacatgggg tccatccgcg atcagatcag caattatgac aacagcgact   1740
caaacaaaca acgacaaagg tcttataaca acagaaactg gtgcaacagc cacaccttat   1800
gactctggag caggagaact aagctcaaca gcatcaatgc aaccaggact agtttacgag   1860
actactgaaa ctgactacct gaactttctc tgttactatg gatataacgt aaccacaata   1920
aaggctatgt caaaagcttt tccagagaat tttacttgcc ctgcagattc caacttagac   1980
ttgatctcca ccatcaatta cccgtcaatt ggaatctctg gattcaaagg aaatggtagc   2040
aagacagtta caagaacagt gaccaatgtt ggtgaggacg gtgaggcggt ttacacagtc   2100
agcgtggaaa caccaccagg gtttaacatt caagtgacgc cagaaaaact ccaatttaca   2160
aaagatggtg agaagttgac ataccaggtg atagtgtctg ctactgcttc acttaagcaa   2220
gatgtatttg gggctcttac ttggtctaat gccaagtaca aggtcagaag cccaattgta   2280
attagtagcg agagtagccg cacaaactga                                    2310
```

<210> SEQ ID NO 14
<211> LENGTH: 759
<212> TYPE: PRT
<213> ORGANISM: Nicotiana benthamiana

<400> SEQUENCE: 14

```
Met Ala Asn His Ile Thr Leu Cys Ile Trp Leu Leu Phe Phe Phe Ile
1               5                   10                  15
```

```
Ser Ile Phe Ser Leu Ala Lys Ser Glu Thr Tyr Ile Ile His Met Asp
            20                  25                  30

Leu Ser Ala Met Pro Lys Ala Phe Ser Ser His His Asn Trp Tyr Leu
        35                  40                  45

Thr Thr Leu Ser Ser Val Ser Asp Ser Ser Thr Asn His Lys Asp Phe
    50                  55                  60

Leu Ser Ser Lys Leu Val Tyr Ala Tyr Thr Asn Ala Ile His Gly Phe
65                  70                  75                  80

Ser Ala Ser Leu Ser Pro Ser Glu Leu Glu Ala Ile Lys Tyr Ser Pro
                85                  90                  95

Gly Tyr Val Ser Ser Ile Lys Asp Ile Ser Val Lys Ile Asp Thr Thr
            100                 105                 110

His Thr Ser Gln Phe Leu Gly Leu Asn Ser Lys Ser Gly Val Trp Pro
        115                 120                 125

Thr Ser Asp Tyr Gly Lys Asp Ile Ile Ile Gly Leu Val Asp Thr Gly
    130                 135                 140

Ile Trp Pro Glu Ser Lys Ser Tyr Ser Asp Asp Gly Ile Ser Glu Val
145                 150                 155                 160

Pro Ser Arg Trp Lys Gly Glu Cys Glu Ser Gly Thr Glu Phe Asn Ser
                165                 170                 175

Ser Leu Cys Asn Lys Lys Leu Ile Gly Ala Arg Tyr Phe Asn Lys Gly
            180                 185                 190

Leu Leu Ala Asn Asn Pro Asn Leu Asn Ile Ser Met Asn Ser Ser Arg
        195                 200                 205

Asp Thr Asp Gly His Gly Thr His Thr Ser Ser Thr Ala Ala Gly Ser
    210                 215                 220

Tyr Val Glu Gly Ala Ser Tyr Phe Gly Tyr Ala Thr Gly Thr Ala Ile
225                 230                 235                 240

Gly Ile Ala Pro Lys Ala His Val Ala Met Tyr Lys Ala Leu Trp Glu
                245                 250                 255

Glu Gly Val Tyr Leu Ser Asp Val Leu Ala Ala Ile Asp Gln Ala Ile
            260                 265                 270

Thr Asp Gly Val Asp Val Leu Ser Leu Ser Leu Gly Ile Asp Ala Ile
        275                 280                 285

Pro Leu His Glu Asp Pro Val Ala Ile Ala Ala Phe Ala Ala Leu Glu
    290                 295                 300

Lys Gly Ile Phe Val Ser Thr Ser Ala Gly Asn Glu Gly Pro Tyr Tyr
305                 310                 315                 320

Glu Thr Leu His Asn Gly Thr Pro Trp Val Leu Thr Val Ala Ala Gly
                325                 330                 335

Thr Val Asp Arg Glu Phe Ile Gly Thr Leu Thr Leu Gly Asn Gly Val
            340                 345                 350

Ser Val Pro Gly Leu Ser Leu Tyr Pro Gly Asn Ser Ser Ser Ser Glu
        355                 360                 365

Ser Ser Leu Val Tyr Val Glu Cys Gln Asp Asp Lys Glu Leu Gln Lys
    370                 375                 380

Asn Ala His Lys Phe Val Val Cys Leu Asp Lys Asn Asp Ser Val Gly
385                 390                 395                 400

Glu His Val Tyr Asn Val Arg Asn Ser Lys Val Ala Gly Ala Val Phe
                405                 410                 415

Ile Thr Asn Thr Thr Asp Leu Glu Phe Tyr Leu Gln Ser Glu Phe Pro
            420                 425                 430

Ala Val Phe Leu Asn Leu Gln Glu Gly Asp Lys Val Leu Glu Tyr Ile
```

```
        435                 440                 445

Lys Ser Asn Ser Ala Pro Lys Gly Lys Leu Glu Phe Gln Val Thr His
    450                 455                 460

Ile Gly Ala Lys Pro Ala Pro Lys Val Ala Thr Tyr Ser Ser Arg Gly
465                 470                 475                 480

Pro Ser Pro Ser Cys Pro Ser Ile Leu Lys Pro Asp Leu Met Ala Pro
                485                 490                 495

Gly Ala Leu Ile Leu Ala Ser Trp Pro Gln Gln Ser Pro Val Thr Asp
            500                 505                 510

Val Thr Ser Gly Lys Leu Phe Ser Asn Phe Asn Ile Ile Ser Gly Thr
        515                 520                 525

Ser Met Ser Cys Pro His Ala Ser Gly Val Ala Ala Leu Leu Lys Ala
    530                 535                 540

Ala His Pro Glu Trp Ser Pro Ala Ala Ile Arg Ser Ala Met Met Thr
545                 550                 555                 560

Thr Ser Thr Ala Leu Asp Asn Thr Gln Ser Pro Ile Arg Asp Ile Gly
                565                 570                 575

Asn Lys Asn Ala Ala Ala Thr Pro Leu Ala Met Gly Ala Gly His Ile
            580                 585                 590

Asp Pro Asn Lys Ala Leu Asp Pro Gly Leu Ile Tyr Asp Ala Thr Pro
        595                 600                 605

Gln Asp Tyr Val Asn Leu Leu Cys Ala Leu Asn Phe Thr Ser Lys Gln
    610                 615                 620

Ile Lys Thr Ile Thr Arg Ser Ser Ser Tyr Thr Cys Ser Asn Pro Ser
625                 630                 635                 640

Leu Asp Leu Asn Tyr Pro Ser Phe Ile Gly Phe Phe Asn Gly Asn Ser
                645                 650                 655

Ser Glu Ser Asp Pro Lys Arg Ile Gln Glu Phe Lys Arg Thr Val Thr
            660                 665                 670

Asn Leu Gln Asp Gly Thr Ser Ile Tyr Thr Ala Asn Phe Thr Pro Met
        675                 680                 685

Gly Lys Phe Lys Val Ser Val Val Pro Glu Lys Leu Val Phe Lys Glu
    690                 695                 700

Lys Tyr Glu Lys Leu Ser Tyr Lys Leu Arg Ile Glu Gly Pro Ile Val
705                 710                 715                 720

Met Asp Asp Asn Val Val Tyr Gly Ser Leu Ser Trp Val Glu Thr Gly
                725                 730                 735

Gly Asn Tyr Val Val Arg Ser Pro Ile Val Ala Thr Ser Ile Lys Val
            740                 745                 750

Asp Pro Leu Thr Gly His Asn
        755


<210> SEQ ID NO 15
<211> LENGTH: 2280
<212> TYPE: DNA
<213> ORGANISM: Nicotiana benthamiana

<400> SEQUENCE: 15

atggcaaatc atattacctt gtgtatttgg ttgcttttct tctttatttc tatattttca      60

ctagcaaagt cagaaacata tatcattcat atggatttgt cagccatgcc aaaagctttt     120

tctagccatc ataattggta cttgacaaca ctttcttctg tatcagacag cagtacaaat     180

cacaaagact tcttgtcctc aaaactagtc tatgcttata ctaatgctat acatggtttt     240

agtgcaagtc tctctccttc tgaacttgaa gccataaaat attctccagg ttatgtttct     300
```

```
tcaattaagg atatttcagt taaaattgac acaactcaca catcccagtt tcttggccta    360
aactctaagt ctggtgtatg gccaacgtcc gactatggga aagatatcat aattggctta    420
gttgatactg gaatatggcc tgagagtaaa agctatagtg atgatgggat tagtgaagta    480
ccatcaagat ggaaaggaga atgtgaaagt ggtactgagt tcaattcctc tttgtgtaac    540
aagaagctca ttggcgctcg ttacttcaat aaaggcctac ttgccaacaa tccaaatctt    600
aatatttcaa tgaattcttc tagagatacc gatggacatg gaactcacac ttcttctaca    660
gctgcgggaa gttatgttga gggtgcatct tattttggct atgccaccgg tactgctatt    720
ggcatagcgc caaaggctca tgtggctatg tacaaggctc tatgggaaga aggtgtatac    780
ttgtctgatg ttcttgctgc aattgatcaa gcaattacag atggtgtgga tgtcttatcc    840
ttgtcgttag gcatagacgc gattccacta cacgaagatc ctgtggcaat tgccgcattt    900
gctgcattgg agaaaggtat atttgtttcc acctctgcag gaaatgaagg gccttattat    960
gagactttgc acaatggaac accttgggtg ttaactgttg cagctggcac agttgaccgc   1020
gaatttattg gaacattaac tcttggaaat ggagtttcag tccctggttt atcgctatac   1080
cctgggaatt ctagttcaag cgaaagctcc cttgtctatg tcgaatgcca agatgacaag   1140
gaactgcaga aaaatgcaca caaatttgtt gtctgtctcg acaagaatga ttcggttggt   1200
gagcatgtgt acaatgtaag aaattcaaaa gttgctgggg ctgtctttat aactaataca   1260
actgacttgg aattctacct ccaaagcgaa ttcccggctg tgttcttgaa cttacaagag   1320
ggtgataaag ttctagagta cattaagagc aactctgcac ctaaaggaaa acttgaattc   1380
caagttacac atattggtgc taaaccagcg ccaaaagttg ctacctatag ctcaagagga   1440
ccgtcaccga gttgtccaag tatcctcaaa cctgatctca tggctcctgg tgccttaata   1500
cttgcttcat ggccacaaca atcaccagtt actgatgtta cctcaggaaa actttttagt   1560
aacttcaata ttatatctgg tacatcaatg tcatgtccac atgcttctgg tgtagcagca   1620
cttctaaaag ctgcacaccc tgaatggagc cctgcagcca tccgatctgc catgatgacc   1680
acttccactg cgttggacaa cacacagagc cccatccgag acataggtaa caagaatgcg   1740
gctgctactc ctctagccat gggagctggc catatcgatc caaacaaggc gttagatcct   1800
ggacttatct atgatgcaac accacaagat tatgtcaatc tcctctgtgc tctgaacttc   1860
acatccaaac aaataaaaac catcacaaga tcctcatctt atacttgctc caacccatca   1920
ttggacttaa actatccatc cttcattggc tttttcaatg gtaacagcag cgagtcggat   1980
cctaaaagga ttcaagaatt taaaagaaca gtgacaaact tacaagatgg tacatcaata   2040
tatacagcaa acttcactcc aatgggtaaa tttaaagtta gtgttgtacc tgaaaagttg   2100
gttttcaaag agaagtatga aaagctgagc tacaagctta gaatagaagg tccaatagtt   2160
atggatgata atgtggttta tggttctttg agctgggtag aaactggagg taactatgtg   2220
gttagaagtc caattgttgc cacaagcata aaagtggatc ctttgacagg acacaactga   2280
```

```
<210> SEQ ID NO 16
<211> LENGTH: 762
<212> TYPE: PRT
<213> ORGANISM: Nicotiana tabacum

<400> SEQUENCE: 16

Met Ala Asn His Ile Thr Leu Cys Ile Trp Leu Leu Phe Phe Phe Ile
1               5                   10                  15

Ser Ile Ile Ser Leu Ala Lys Ser Glu Thr Tyr Ile Ile His Met Asp
```

```
            20                  25                  30

Phe Ser Ala Met Pro Lys Ala Phe Ser Ser His His Asn Trp Tyr Leu
        35                  40                  45

Thr Thr Leu Ser Ser Val Ser Asp Ser Ser Thr Asn Tyr Lys Asp Phe
    50                  55                  60

Leu Ser Ser Lys Leu Val Tyr Ser Tyr Thr Asn Ala Ile His Gly Phe
65                  70                  75                  80

Ser Ala Ser Leu Ser Pro Ser Glu Leu Glu Ala Ile Lys Asn Ser Pro
                85                  90                  95

Gly Tyr Val Ser Ser Ile Lys Asp Ile Ser Val Lys Ile Asp Thr Thr
            100                 105                 110

His Thr Ser Gln Phe Leu Gly Leu Asn Ser Glu Ser Gly Val Trp Pro
        115                 120                 125

Thr Ser Glu Tyr Gly Lys Asp Ile Ile Ile Gly Leu Val Asp Thr Gly
    130                 135                 140

Ile Trp Ser Glu Ser Lys Ser Tyr Ser Asp Asp Gly Ile Ser Glu Val
145                 150                 155                 160

Pro Ser Arg Trp Lys Gly Glu Cys Glu Ser Gly Thr Glu Phe Asn Ser
                165                 170                 175

Ser Leu Cys Asn Lys Lys Leu Ile Gly Ala Arg Tyr Phe Asn Lys Gly
            180                 185                 190

Leu Leu Ala Asn Asn Pro Asn Leu Asn Ile Ser Met Asn Ser Ala Arg
        195                 200                 205

Asp Thr Asp Gly His Gly Thr His Thr Ser Ser Thr Ala Ala Gly Ser
    210                 215                 220

Tyr Val Glu Gly Ala Ser Tyr Phe Gly Tyr Ala Thr Gly Thr Ala Ile
225                 230                 235                 240

Gly Ile Ala Pro Lys Ala His Val Ala Met Tyr Lys Ala Leu Trp Glu
                245                 250                 255

Glu Gly Val Tyr Leu Ser Asp Val Leu Ala Ala Ile Asp Gln Ala Ile
            260                 265                 270

Thr Asp Gly Val Asp Val Leu Ser Leu Ser Leu Gly Ile Asp Ala Ile
        275                 280                 285

Pro Leu His Glu Asp Pro Val Ala Ile Ala Ala Phe Ala Ala Leu Glu
    290                 295                 300

Lys Gly Ile Phe Val Ser Thr Ser Ala Gly Asn Glu Gly Pro Tyr Tyr
305                 310                 315                 320

Glu Thr Leu His Asn Gly Thr Pro Trp Val Leu Thr Val Ala Ala Gly
                325                 330                 335

Thr Val Asp Arg Glu Phe Ile Gly Thr Leu Thr Leu Gly Asn Gly Val
            340                 345                 350

Ser Val Thr Gly Leu Ser Leu Tyr Pro Gly Asn Ser Ser Ser Ser Glu
        355                 360                 365

Ser Ser Ile Val Tyr Val Glu Cys Gln Asp Asp Lys Glu Leu Gln Lys
    370                 375                 380

Asn Ala His Lys Phe Val Val Cys Leu Asp Lys Asn Asp Ser Val Gly
385                 390                 395                 400

Glu His Val Tyr Asn Val Arg Asn Ser Lys Val Ala Gly Ala Val Phe
                405                 410                 415

Ile Thr Asn Thr Thr Asp Leu Glu Phe Tyr Leu Gln Ser Glu Phe Pro
            420                 425                 430

Ala Val Phe Leu Asn Leu Gln Glu Gly Asp Lys Val Leu Glu Tyr Ile
        435                 440                 445
```

```
Lys Ser Asn Ser Ala Pro Lys Gly Lys Leu Glu Phe Gln Val Thr His
    450                 455                 460

Ile Gly Ala Lys Arg Ala Pro Glu Val Ala Thr Tyr Ser Ser Arg Gly
465                 470                 475                 480

Pro Ser Pro Ser Cys Pro Ser Ile Leu Lys Pro Asp Leu Met Ala Pro
                485                 490                 495

Gly Ala Leu Ile Leu Ala Ser Trp Pro Gln Gln Ser Pro Val Thr Asp
            500                 505                 510

Val Thr Ser Gly Lys Leu Phe Ser Asn Phe Asn Ile Ile Ser Gly Thr
        515                 520                 525

Ser Met Ser Cys Pro His Ala Ser Gly Val Ala Ala Leu Leu Lys Gly
    530                 535                 540

Ala His Pro Glu Trp Ser Pro Ala Ala Ile Arg Ser Ala Met Met Thr
545                 550                 555                 560

Thr Ser Ser Ala Leu Asp Asn Thr Gln Ser Pro Ile Arg Asp Ile Gly
                565                 570                 575

Asn Val Glu Leu Arg Asn Ala Ala Ala Thr Pro Leu Ala Met Gly Ala
            580                 585                 590

Gly His Ile Asp Pro Asn Lys Ala Leu Asp Pro Gly Leu Ile Tyr Asp
        595                 600                 605

Ala Thr Pro Gln Asp Tyr Val Asn Leu Leu Cys Ala Leu Asn Phe Thr
    610                 615                 620

Ser Lys Gln Ile Lys Ile Ile Thr Arg Ser Ser Ser Tyr Thr Cys Ser
625                 630                 635                 640

Asn Pro Ser Leu Asp Leu Asn Tyr Pro Ser Phe Ile Gly Phe Phe Asn
                645                 650                 655

Gly Asn Ser Arg Glu Ser Asp Pro Lys Arg Ile Gln Glu Phe Lys Arg
            660                 665                 670

Thr Val Thr Asn Leu Gln Asp Gly Thr Ser Val Tyr Thr Ala Asn Leu
        675                 680                 685

Thr Pro Met Gly Lys Phe Lys Val Ser Val Val Pro Glu Lys Leu Val
    690                 695                 700

Phe Lys Glu Lys Tyr Glu Lys Leu Ser Tyr Lys Leu Arg Ile Glu Gly
705                 710                 715                 720

Pro Ile Val Met Asp Asp Asn Val Val Tyr Gly Ser Leu Ser Trp Val
                725                 730                 735

Glu Thr Gly Gly Lys Tyr Val Val Arg Ser Pro Ile Val Ala Thr Ser
            740                 745                 750

Ile Lys Val Asp Pro Leu Thr Gly His Asn
        755                 760
```

<210> SEQ ID NO 17
<211> LENGTH: 2289
<212> TYPE: DNA
<213> ORGANISM: Nicotiana tabacum

<400> SEQUENCE: 17

```
atggcaaatc atattacctt gtgtatttgg ttgcttttct tctttatttc tataatttca      60

ctagcaaagt cagaaacata tatcattcat atggattttt cagccatgcc aaaagctttt     120

tctagccatc ataattggta cttgacaaca ctttcttctg tatcagacag cagtacaaat     180

tacaaagact tcttgtcctc aaaactagtc tattcttata ctaatgccat acatggtttt     240

agtgcaagtc tttctccttc tgaacttgaa gccataaaaa attctccagg ctatgtttct     300
```

```
tcaattaagg atatttcagt taaaattgac acaactcaca catcccaatt tcttggccta    360
aactctgagt ctggtgtatg gccaacgtcc gagtatggta aagatatcat aattggctta    420
gttgatactg gaatatggtc ggagagtaaa agctatagtg atgatgggat tagtgaagta    480
ccatcaagat ggaaaggaga atgtgaaagt ggtactgagt tcaattcctc tttgtgtaac    540
aagaaactca ttggcgctcg ttacttcaat aaaggcctac ttgccaacaa tccaaatctt    600
aacatttcaa tgaattctgc tagagatacc gatggacatg gaactcacac ttcttctaca    660
gctgcgggaa gttatgtcga gggtgcatct tattttggct atgccactgg cactgctata    720
ggcatagcac caaaggctca tgtggctatg tacaaggctc tatgggaaga aggtgtatac    780
ttgtctgatg ttcttgctgc aattgatcaa gcaattacag atggtgtgga tgtcttatcc    840
ttgtctttag gcatagacgc gattccacta cacgaagatc ctgtggcaat tgccgcattt    900
gctgcattgg agaaaggtat atttgtttcc acctctgcag gaaatgaagg gccttattat    960
gagactttgc acaatggaac accttgggtg ctaactgttg cagctggcac agttgaccgc   1020
gaatttattg gaacattaac tcttggaaat ggagtttcag tcactggctt atcgctatac   1080
cctgggaatt ctagttcaag cgaaagctcc attgtctatg tcgaatgcca agatgacaag   1140
gaactacaga aaaatgcaca taaatttgtt gtctgtctcg acaagaatga ttcggtcggt   1200
gagcatgtgt acaatgtaag aaattcaaaa gttgctgggg ctgtctttat aactaataca   1260
actgacttgg aattctacct ccaaagcgaa ttcccggctg tgttcttgaa cttacaagag   1320
ggtgataaag ttctagagta cattaagagc aactctgcac ctaaaggaaa acttgaattc   1380
caagtgacac atattggtgc taaacgagca ccagaagttg ctacctatag ctcaagagga   1440
ccgtcaccga gttgtccaag tatcctcaag cctgatctca tggctcctgg tgccttaata   1500
cttgcttcat ggccacagca atcaccagtt actgatgtta cctcaggaaa gctttttagt   1560
aacttcaata ttatatctgg tacatcaatg tcatgtccac atgcttctgg tgtagcagca   1620
cttctaaaag gcgcacaccc tgaatggagc cccgcagcca tccgatctgc catgatgacc   1680
acttccagtg cgttggacaa cacacagagc cccatccgag acataggtaa tgttgaactc   1740
aggaatgctg ctgctactcc tctagccatg ggagctggcc atatcgatcc aaacaaggca   1800
ttagatcctg gacttatcta tgatgcgaca ccacaagatt atgtcaatct tctctgtgct   1860
ctgaacttca catccaaaca aataaaaatc atcacaagat cctcatctta tacttgctcc   1920
aacccatcat tggacttaaa ctatccatcc ttcattggct tttcaatgg gaacagcaga    1980
gagtcggatc ctaaaaggat tcaagaattc aaaagaacag tgacaaactt acaagatggt   2040
acatcagtat atacagcaaa tctcactcca atgggtaaat ttaaagttag tgttgtacct   2100
gaaaagttgg ttttcaaaga gaagtatgaa aagctgagct acaagcttag aatagaaggt   2160
ccaatagtta tggatgataa tgtggtttat ggttctttga gctgggtaga aactggaggt   2220
aaatatgtgg ttagaagtcc aattgttgcc acaagcataa aagtggatcc tttgacagga   2280
cacaactga                                                           2289
```

```
<210> SEQ ID NO 18
<211> LENGTH: 759
<212> TYPE: PRT
<213> ORGANISM: Nicotiana tabacum

<400> SEQUENCE: 18

Met Ala Ser His Ile Thr Leu Cys Ile Trp Leu Leu Phe Phe Phe Ile
1               5                   10                  15
```

```
Ser Ile Ile Ser Leu Ala Lys Pro Glu Thr Tyr Ile Ile His Met Asp
            20                  25                  30

Leu Ser Ala Met Pro Lys Ala Phe Ala Ser His His Asn Trp Tyr Leu
        35                  40                  45

Thr Thr Leu Ala Ser Leu Ser Asp Ser Ser Thr Asn His Lys Glu Phe
    50                  55                  60

Leu Ser Ser Lys Leu Val Tyr Ala Tyr Thr Asn Ala Ile Asn Gly Phe
65                  70                  75                  80

Ser Ala Ser Leu Ser Pro Ser Glu Phe Glu Ala Ile Lys Asn Ser Pro
                85                  90                  95

Gly Tyr Val Ser Ser Ile Lys Asp Met Ser Val Lys Ile Asp Thr Thr
            100                 105                 110

His Thr Ser Gln Phe Leu Gly Leu Asn Ser Glu Ser Gly Val Trp Pro
        115                 120                 125

Thr Ser Asp Tyr Gly Lys Asp Ile Ile Ile Gly Leu Val Asp Thr Gly
    130                 135                 140

Ile Trp Pro Glu Ser Lys Ser Tyr Ser Asp Tyr Gly Ile Ser Glu Val
145                 150                 155                 160

Pro Ser Arg Trp Lys Gly Glu Cys Glu Ser Gly Ile Glu Phe Asn Ser
                165                 170                 175

Ser Leu Cys Asn Lys Lys Ile Ile Gly Ala Arg Tyr Phe Asn Lys Gly
            180                 185                 190

Leu Leu Ala Asn Asn Pro Asn Leu Asn Ile Ser Met Asn Ser Ala Arg
        195                 200                 205

Asp Thr Asp Gly His Gly Thr His Thr Ser Ser Thr Ala Ala Gly Ser
    210                 215                 220

Tyr Val Glu Gly Ala Ser Tyr Phe Gly Tyr Ala Thr Gly Thr Ala Ile
225                 230                 235                 240

Gly Ile Ala Pro Lys Ala His Val Ala Met Tyr Lys Ala Leu Trp Glu
                245                 250                 255

Glu Gly Val Tyr Leu Ser Asp Val Leu Ala Ala Ile Asp Gln Ala Ile
            260                 265                 270

Thr Asp Gly Val Asp Val Leu Ser Leu Ser Leu Gly Ile Asp Ala Ile
        275                 280                 285

Pro Leu His Glu Asp Pro Val Ala Ile Ala Ala Phe Ala Ala Leu Glu
    290                 295                 300

Lys Gly Ile Phe Val Ser Thr Ser Ala Gly Asn Glu Gly Pro Tyr Tyr
305                 310                 315                 320

Glu Thr Leu His Asn Gly Thr Pro Trp Val Leu Thr Val Ala Ala Gly
                325                 330                 335

Thr Val Asp Arg Glu Phe Ile Gly Ala Leu Thr Leu Gly Asn Gly Val
            340                 345                 350

Ser Val Thr Gly Leu Ser Leu Tyr Pro Gly Asn Ser Ser Ser Ser Glu
        355                 360                 365

Ser Ser Ile Val Tyr Val Glu Cys Gln Asp Asp Lys Glu Leu Gln Lys
    370                 375                 380

Ser Ala His Asn Ile Val Val Cys Leu Asp Lys Asn Asp Ser Val Ser
385                 390                 395                 400

Glu His Val Tyr Asn Val Arg Asn Ser Lys Val Ala Gly Ala Val Phe
                405                 410                 415

Ile Thr Asn Ile Thr Asp Leu Glu Phe Tyr Leu Gln Ser Glu Phe Pro
            420                 425                 430

Ala Val Phe Leu Asn Leu Gln Glu Gly Asp Lys Val Leu Glu Tyr Ile
```

```
        435                 440                 445

Lys Ser Asn Ser Ala Pro Lys Gly Lys Leu Glu Phe Arg Val Thr His
    450                 455                 460

Ile Gly Ala Lys Pro Ala Pro Lys Val Ala Thr Tyr Ser Ser Arg Gly
465                 470                 475                 480

Pro Ser Pro Ser Cys Pro Ser Ile Leu Lys Pro Asp Leu Met Ala Pro
                485                 490                 495

Gly Ala Leu Ile Leu Ala Ser Trp Pro Gln Gln Ser Pro Val Thr Asp
            500                 505                 510

Val Thr Ser Gly Lys Leu Phe Ser Asn Phe Asn Ile Ile Ser Gly Thr
        515                 520                 525

Ser Met Ser Cys Pro His Ala Ser Gly Val Ala Ala Leu Leu Lys Ala
    530                 535                 540

Ala His Pro Glu Trp Ser Pro Ala Ala Ile Arg Ser Ala Met Met Thr
545                 550                 555                 560

Thr Ser Asn Ala Met Asp Asn Thr Gln Ser Pro Ile Arg Asp Ile Gly
                565                 570                 575

Ser Lys Asn Ala Ala Ala Thr Pro Leu Ala Met Gly Ala Gly His Ile
            580                 585                 590

Asp Pro Asn Lys Ala Leu Asp Pro Gly Leu Ile Tyr Asp Ala Thr Pro
        595                 600                 605

Gln Asp Tyr Val Asn Leu Leu Cys Ala Leu Asn Phe Thr Ser Lys Gln
    610                 615                 620

Ile Lys Thr Ile Thr Arg Ser Ser Ser Tyr Thr Cys Ser Asn Pro Ser
625                 630                 635                 640

Leu Asp Leu Asn Tyr Pro Ser Phe Ile Gly Phe Phe Asn Gly Asn Ser
                645                 650                 655

Ser Glu Ser Asp Pro Arg Arg Ile Gln Glu Phe Gln Arg Thr Val Thr
            660                 665                 670

Asn Ile Gly Asp Gly Met Ser Val Tyr Thr Ala Lys Leu Thr Thr Met
        675                 680                 685

Gly Lys Phe Lys Val Asn Leu Val Pro Glu Lys Leu Val Phe Lys Glu
    690                 695                 700

Lys Tyr Glu Lys Leu Ser Tyr Lys Leu Arg Ile Glu Gly Pro Leu Val
705                 710                 715                 720

Met Asp Asp Ile Val Val Tyr Gly Ser Leu Ser Trp Val Glu Thr Glu
                725                 730                 735

Gly Lys Tyr Val Val Arg Ser Pro Ile Val Ala Thr Ser Ile Lys Val
            740                 745                 750

Asp Pro Leu Thr Gly His Asn
        755
```

<210> SEQ ID NO 19
<211> LENGTH: 2280
<212> TYPE: DNA
<213> ORGANISM: Nicotiana tabacum

<400> SEQUENCE: 19

```
atggcaagtc atattacctt gtgtatttgg ttgcttttct tctttatttc tataatttca      60

ctagcaaagc cagaaacata tatcattcat atggatttgt cagccatgcc aaaagctttt     120

gctagccatc ataattggta cttgacaaca cttgcttctt tatcagacag tagtacaaat     180

cacaaagaat tcttgtcctc aaaactagtc tatgcttata ctaatgccat caatggtttt     240

agtgcaagtc tttctccttc tgaatttgaa gccataaaaa attctccagg ttatgtttct     300
```

```
tcaattaagg atatgtcagt taaaattgac acaactcaca catcccaatt ccttggccta    360
aactctgagt ctggtgtatg gccaacgtcc gactatggta aagatatcat aattggctta    420
gttgatactg gaatatggcc agagagtaaa agctatagtg attatgggat tagtgaagta    480
ccatcaagat ggaaaggaga atgtgaaagt ggcattgagt tcaattcctc tttgtgtaac    540
aagaaaatca ttggcgctcg ttacttcaat aaaggcctac ttgccaacaa tccaaatctt    600
aacatttcaa tgaattctgc tagagataca gatggacatg gaactcacac ttcttccaca    660
gctgcgggaa gttatgtcga gggtgcatct tattttggct atgccaccgg cactgctatt    720
ggcatagcac caaaggctca tgtggctatg tacaaggctc tatgggaaga aggtgtatac    780
ttgtctgatg ttcttgctgc aattgatcaa gcaattacag atggtgtaga tgttttatcc    840
ttgtcattag gcatagacgc gattccacta cacgaagatc ctgtggcaat tgccgcattt    900
gctgcattgg agaaaggtat atttgtttcc acctctgcag gaaatgaagg gccttattat    960
gagactttgc acaatggaac accttgggtg ctaactgttg cagctggcac agttgaccgc   1020
gaatttattg gcgcattaac tcttggaaat ggagtttcag tcactggctt atcgctctac   1080
cctgggaatt ctagttcaag tgaaagctcc attgtctatg ttgaatgcca agatgacaag   1140
gaactgcaaa aaagtgcaca caatattgtt gtctgccttg acaagaatga ttcggtcagt   1200
gagcatgtgt acaatgtgag aaattcaaaa gttgctgggg ctgtcttcat aactaatata   1260
actgatttgg aattctacct ccaaagcgaa ttcccggctg tgttcttgaa cttacaagag   1320
ggtgataaag ttctagagta cattaagagc aactctgcac ctaaaggaaa acttgaattc   1380
cgagtgacac atattggtgc taaaccagca ccaaaagttg ctacctatag ctcaagagga   1440
ccgtcaccga gctgtccaag tatcctcaag cctgatctca tggctcctgg tgccttaata   1500
ctagcttcat ggccacaaca atcaccagtg actgatgtta cctcaggaaa actttttagt   1560
aacttcaata ttatatctgg tacatcaatg tcatgtccac atgcttctgg tgtagcagca   1620
cttctaaaag ccgcacaccc tgaatggagc cctgcagcca tccgatctgc catgatgacc   1680
acttccaatg cgatggacaa cacacaaagt cccatccgag acataggtag taagaatgct   1740
gctgctactc ctctagccat gggagctggc catatcgatc caaacaaggc actagatcct   1800
ggacttatct atgatgcgac accacaagat tatgtcaatc ttctctgtgc tctgaacttc   1860
acatccaaac aaataaaaac catcacaaga tcctcatctt atacttgctc caacccatca   1920
ttggacttaa actatccatc tttcattgga tttttcaatg ggaacagcag cgagtcggat   1980
cctagaagga tacaagaatt ccagaggacc gtgactaata ttggagatgg tatgtcagta   2040
tacacagcaa aattgaccac aatgggtaaa tttaaagtta atcttgtacc tgaaaagttg   2100
gttttcaaag agaagtatga aaagttgagc tacaagctaa gaatagaagg tccattagtt   2160
atggatgata ttgtggttta tggttctttg agctgggtag aaactgaagg taaatatgtg   2220
gttagaagtc caattgttgc cacaagcata aaagtagatc ctttgacagg acacaactga   2280
```

<210> SEQ ID NO 20
<211> LENGTH: 751
<212> TYPE: PRT
<213> ORGANISM: Solanum lycopersicum

<400> SEQUENCE: 20

```
Met Ala Asn Tyr Ile Ala Leu Cys Ile Trp Leu Leu Ser Ile Ile Gln
1               5                   10                  15

Leu Ala Lys Ser Glu Thr Tyr Ile Ile His Met Asp Leu Ser Ala Met
```

```
            20                  25                  30

Pro Lys Ala Phe Ser Ser His Tyr Asn Trp Tyr Leu Thr Thr Leu Phe
        35                  40                  45

Ser Val Ser Asp Ser Lys Asp Leu Leu Ser Ser Lys Leu Val Tyr Thr
    50                  55                  60

Tyr Thr Asn Ala Ile Asn Gly Phe Ser Ala Ser Leu Ser Pro Ser Glu
65                  70                  75                  80

Ile Glu Ala Ile Lys Asn Ser Pro Gly Tyr Val Ser Ser Ile Lys Asp
                85                  90                  95

Met Ser Val Lys Val Asp Thr Thr His Thr Ser Gln Phe Leu Gly Leu
            100                 105                 110

Asn Ser Glu Ser Gly Val Trp Pro Lys Ser Asp Tyr Gly Lys Asp Val
        115                 120                 125

Ile Val Gly Leu Val Asp Thr Gly Ile Trp Pro Glu Ser Arg Ser Tyr
    130                 135                 140

Ser Asp Asp Gly Met Asn Glu Val Pro Ser Arg Trp Lys Gly Glu Cys
145                 150                 155                 160

Glu Ser Gly Thr Gln Phe Asn Thr Ser Leu Cys Asn Lys Lys Leu Ile
                165                 170                 175

Gly Ala Arg Tyr Phe Asn Lys Gly Leu Leu Ala Asn Asn Pro Asn Leu
            180                 185                 190

Thr Ile Ser Met Asp Ser Ala Arg Asp Thr Asp Gly His Gly Thr His
        195                 200                 205

Thr Ser Ser Thr Ala Ala Gly Ser Arg Val Glu Gly Ala Ser Phe Phe
    210                 215                 220

Gly Tyr Ala Ala Gly Thr Ala Thr Gly Val Ala Pro Lys Ala His Val
225                 230                 235                 240

Ala Met Tyr Lys Ala Leu Trp Glu Glu Gly Val Phe Leu Ser Asp Ile
                245                 250                 255

Leu Ala Ala Ile Asp Gln Ala Ile Ala Asp Gly Val Asp Val Leu Ser
            260                 265                 270

Leu Ser Leu Gly Ile Asp Ala Leu Pro Leu Tyr Glu Asp Pro Val Ala
        275                 280                 285

Ile Ala Ala Phe Ala Ala Leu Glu Lys Gly Ile Phe Val Ser Thr Ser
    290                 295                 300

Ala Gly Asn Glu Gly Pro Phe Leu Glu Thr Leu His Asn Gly Thr Pro
305                 310                 315                 320

Trp Val Leu Thr Val Ala Ala Gly Thr Val Asp Arg Glu Phe Ile Gly
                325                 330                 335

Thr Val Thr Leu Gly Asn Gly Val Ser Val Thr Gly Leu Ser Leu Tyr
            340                 345                 350

Pro Gly Asn Ser Ser Ser Ser Glu Ser Ser Ile Ser Phe Val Asp Cys
        355                 360                 365

Gln Asp Asp Lys Glu Leu Gln Lys Asn Ala His Arg Ile Val Val Cys
    370                 375                 380

Ile Asp Asn Asn Asp Ser Val Ser Glu Asp Val Tyr Asn Val Arg Asn
385                 390                 395                 400

Ser Lys Val Ser Gly Ala Val Phe Ile Thr Asn Ser Thr Asp Leu Glu
                405                 410                 415

Phe Tyr Leu Gln Ser Glu Phe Pro Ala Val Phe Leu Asn Ile Gln Glu
            420                 425                 430

Gly Asp Lys Val Leu Glu Tyr Val Arg Ser Asp Ser Ala Pro Asn Ala
        435                 440                 445
```

```
Lys Leu Glu Phe Gln Val Thr Arg Ile Gly Ala Lys Pro Ala Pro Lys
    450                 455                 460

Val Ala Ser Tyr Ser Ser Arg Gly Pro Ser Pro Ser Cys Pro Thr Ile
465                 470                 475                 480

Leu Lys Pro Asp Leu Met Gly Pro Gly Ala Leu Ile Leu Ala Ser Trp
                485                 490                 495

Pro Gln Gln Thr Pro Val Thr Glu Val Thr Ser Gly Lys Leu Tyr Ser
            500                 505                 510

Asn Phe Asn Ile Ile Ser Gly Thr Ser Met Ser Cys Pro His Ala Ser
        515                 520                 525

Gly Val Ala Ala Leu Leu Lys Ser Ala His Pro Glu Trp Ser Pro Ala
    530                 535                 540

Ala Ile Arg Ser Ala Met Met Thr Thr Ala Tyr Val Leu Asp Asn Thr
545                 550                 555                 560

Gln Ser Pro Ile Gln Asp Val Gly Leu Lys Asn Gly Val Ala Thr Pro
                565                 570                 575

Leu Ala Met Gly Ala Gly His Ile Asp Pro Asn Lys Ala Leu Asp Pro
            580                 585                 590

Gly Leu Ile Tyr Asp Ala Thr Pro Gln Asp Tyr Val Asn His Leu Cys
        595                 600                 605

Gly Leu Asn Phe Thr Ser Lys Gln Ile Gln Thr Ile Thr Arg Ser Ser
    610                 615                 620

Thr Tyr Thr Cys Ser Asn Pro Ser Leu Asp Leu Asn Tyr Pro Ser Phe
625                 630                 635                 640

Ile Gly Tyr Phe Asn Arg Asn Ser Ser Asp Ser Asp Pro Lys Arg Ile
                645                 650                 655

Gln Glu Phe Lys Arg Thr Val Thr Asn Leu Gln Asp Gly Thr Ser Val
            660                 665                 670

Tyr Thr Ala Lys Leu Thr Pro Met Gly Lys Phe Lys Val Ser Val Val
        675                 680                 685

Pro Asn Lys Leu Thr Phe Lys Glu Lys Tyr Glu Lys Gln Ser Tyr Lys
    690                 695                 700

Leu Arg Ile Glu Gly Pro Ile Ile Met Asp Asp Ile Val Val Asp Gly
705                 710                 715                 720

Ser Leu Ser Trp Met Glu Thr Arg Gly Lys Tyr Ile Val Lys Ser Pro
                725                 730                 735

Ile Val Ala Thr Ser Ile Arg Val Asp Pro Leu Arg Gly His Asn
            740                 745                 750
```

<210> SEQ ID NO 21
<211> LENGTH: 2256
<212> TYPE: DNA
<213> ORGANISM: Solanum lycopersicum

<400> SEQUENCE: 21

```
atggcaaatt atattgcctt gtgtatttgg ttgctttcta taattcaatt ggcaaagtca     60

gaaacttata tcattcatat ggatttgtca gccatgccaa aagcttttc tagccattat     120

aattggtact tgactacact tttttcggtg tcagatagca aagacttgtt gtcctctaaa    180

ctagtttata cttatactaa tgccatcaat ggtttcagtg caagtctttc tccttctgag    240

atagaagcta ttaagaattc tccgggttat gtttcttcga ttaaggatat gtcggttaaa    300

gttgacacaa cccacacatc tcaattcctt ggccttaact ctgagtctgg tgtatggcca    360

aagtcggatt atggcaaaga tgttatagtt ggattagttg acactgggat atggccagag    420
```

```
agtagaagtt atagtgatga tgggatgaat gaagtaccat caagatggaa aggagaatgt    480
gaaagtggaa ctcagttcaa tacctctttg tgcaataaga aactcattgg cgctcgttac    540
ttcaataaag gcctacttgc taacaacccg aatcttacca tttcgatgga ttctgctcgt    600
gatacggatg gacatgggac tcacacttct tccacggctg ctggaagtcg tgtagagggt    660
gcatcttttt ttggatatgc tgctggaact gctacaggtg tagcaccaaa ggctcatgtg    720
gccatgtaca aggctctatg ggaagaaggt gtattcttgt ctgatattct tgcagcaatt    780
gatcaagcaa ttgcagatgg tgtagatgta ttgtccttgt cattaggcat tgatgcgctt    840
cctttatacg aagatcctgt tgcaattgcc gcatttgctg cactggagaa aggcatattt    900
gtttctacat ctgcaggaaa tgaagggcct tttttggaaa ctttgcacaa tggaacgcct    960
tgggtgctca ctgttgctgc tggcacagtt gaccgggagt ttattggcac agtaacactt   1020
ggaaatggag tttcggtcac tggattatcg ctctaccctg ggaactctag ttcaagtgaa   1080
agctccatta gcttcgttga ttgccaagat gataaggaac tgcagaaaaa tgcacacaga   1140
atagtggtct gcattgacaa taatgattca gttagcgagg acgtctacaa tgtaagaaat   1200
tcaaaagttt ctggtgcagt cttcataact aattcaactg acttggaatt ctatctccaa   1260
agtgaatttc ccgcggtgtt tttgaacatt caagagggtg ataaagttct tgagtacgtt   1320
aggagtgact ctgcacctaa cgcaaagctt gaattccaag tgacgcgtat tggtgctaaa   1380
ccagcaccaa aagttgctag ctatagctca agaggaccat caccaagctg tcctacaatt   1440
ctaaagcctg accttatggg tcctggtgca ttaatacttg cttcatggcc acaacaaaca   1500
ccagtaactg aagttacctc gggaaaactt tatagtaact tcaacattat atcaggcaca   1560
tcaatgtctt gtccacatgc ttctggtgta gcagcacttc taaaaagtgc acaccctgaa   1620
tggagccctg ctgctatccg atccgccatg atgaccacag cctatgtatt ggacaacaca   1680
caaagcccca tccaagacgt aggtctgaag aatggtgttg ctactcctct agctatggga   1740
gctggccata tcgatccaaa caaagcgttg gatcccggac tcatctatga tgcaacacca   1800
caagattatg ttaaccacct ctgtggtttg aacttcacat ccaaacaaat acaaaccatc   1860
acaagatcct caacttacac ttgctccaac ccatcattag acttgaacta tccatcattc   1920
attggctatt tcaaccggaa tagcagcgat tcggatccta aaaggattca agaattcaaa   1980
agaacagtga ctaacttaca agatggtaca tcagtataca cagcaaagct cactccaatg   2040
ggtaaattta aagttagtgt tgtacctaat aagttgactt tcaaagaaaa gtatgaaaaa   2100
caaagctata agctaagaat agaaggtcca ataattatgg atgatattgt ggttgatggt   2160
tcattgagct ggatggaaac tagaggaaaa tacatagtta aaagtccaat tgttgcaaca   2220
agtataagag tggatccttt gagaggacat aactga                             2256
```

<210> SEQ ID NO 22
<211> LENGTH: 751
<212> TYPE: PRT
<213> ORGANISM: Solanum tuberosum

<400> SEQUENCE: 22

```
Met Ala Asn His Ile Ala Leu Cys Ile Trp Leu Leu Ser Ile Ile Gln
1               5                   10                  15

Leu Ala Lys Ser Glu Thr Tyr Ile Ile His Met Asp Leu Ser Ala Met
            20                  25                  30

Pro Lys Ala Phe Ser Ser His His Asn Trp Tyr Leu Thr Thr Leu Ser
        35                  40                  45
```

```
Ser Val Ser Asp Ser Lys Asp Leu Leu Ser Ser Lys Leu Val Tyr Thr
    50                  55                  60

Tyr Thr Asn Ala Ile Asn Gly Phe Ser Ala Ser Leu Ser Pro Ser Glu
65                  70                  75                  80

Ile Glu Ala Ile Lys Asn Ser Pro Gly Tyr Val Ser Ser Ile Lys Asp
                85                  90                  95

Met Ser Val Lys Val Asp Thr Thr His Thr Ser Gln Phe Leu Gly Leu
            100                 105                 110

Asn Ser Glu Ser Gly Val Trp Pro Lys Ser Asp Tyr Gly Lys Asp Val
        115                 120                 125

Ile Val Gly Leu Val Asp Thr Gly Ile Trp Pro Glu Ser Arg Ser Tyr
    130                 135                 140

Ser Asp Asp Gly Met Asn Glu Val Pro Ser Arg Trp Lys Gly Glu Cys
145                 150                 155                 160

Glu Ser Gly Thr Gln Phe Asn Ser Ser Leu Cys Asn Lys Lys Leu Ile
                165                 170                 175

Gly Ala Arg Tyr Phe Asn Lys Gly Leu Leu Ala Asn Asn Pro Asn Leu
            180                 185                 190

Thr Ile Ser Met Asp Ser Ser Arg Asp Thr Asp Gly His Gly Thr His
        195                 200                 205

Thr Ser Ser Thr Ala Ala Gly Ser Arg Val Glu Gly Ala Ser Phe Phe
    210                 215                 220

Gly Tyr Ala Ala Gly Thr Ala Thr Gly Val Ala Pro Lys Ala His Val
225                 230                 235                 240

Ala Met Tyr Lys Ala Leu Trp Glu Glu Gly Val Phe Leu Ser Asp Ile
                245                 250                 255

Leu Ala Ala Ile Asp Gln Ala Ile Glu Asp Gly Val Asp Val Leu Ser
            260                 265                 270

Leu Ser Leu Gly Ile Asp Ala Leu Pro Leu Tyr Glu Asp Pro Val Ala
        275                 280                 285

Ile Ala Ala Phe Ala Ala Leu Glu Lys Gly Ile Phe Val Ser Thr Ser
    290                 295                 300

Ala Gly Asn Glu Gly Pro Phe Leu Glu Thr Leu His Asn Gly Thr Pro
305                 310                 315                 320

Trp Val Leu Thr Val Ala Ala Gly Thr Val Asp Arg Glu Phe Ile Gly
                325                 330                 335

Thr Leu Thr Leu Gly Asn Gly Val Ser Val Thr Gly Leu Ser Leu Tyr
            340                 345                 350

Pro Gly Asn Ser Ser Ser Ser Glu Arg Ser Ile Ser Tyr Val Asp Cys
        355                 360                 365

Gln Asp Asp Lys Glu Leu Gln Lys Asn Ala His Lys Ile Val Val Cys
    370                 375                 380

Ile Asp Lys Ser Asp Ser Val Ser Glu Asp Val Tyr Asn Val Arg Asn
385                 390                 395                 400

Ser Lys Val Ser Gly Ala Val Phe Ile Thr Asn Ser Thr Asp Leu Glu
                405                 410                 415

Phe Tyr Leu Gln Ser Glu Phe Pro Ala Val Phe Leu Asn Ile Gln Glu
            420                 425                 430

Gly Asp Lys Val Leu Glu Tyr Val Arg Ser Glu Ala Ala Pro Asn Ala
        435                 440                 445

Lys Leu Glu Phe Gln Val Thr Arg Ile Gly Ala Lys Pro Ala Pro Lys
    450                 455                 460
```

Val Ala Ser Tyr Ser Ser Arg Gly Pro Ser Pro Ser Cys Pro Ile Ile
465 470 475 480

Leu Lys Pro Asp Leu Met Gly Pro Gly Ala Leu Ile Leu Ala Ser Trp
485 490 495

Pro Gln Gln Thr Pro Val Thr Glu Val Thr Ser Gly Lys Leu Tyr Ser
500 505 510

Asn Phe Asn Ile Ile Ser Gly Thr Ser Met Ser Cys Pro His Ala Ser
515 520 525

Gly Val Ala Ala Leu Leu Lys Ser Ala His Pro Glu Trp Ser Pro Ala
530 535 540

Ala Ile Arg Ser Ala Met Met Thr Thr Ala Tyr Val Leu Asp Asn Thr
545 550 555 560

Gln Ser Pro Ile Gln Asp Ile Gly Leu Lys Asn Gly Val Ala Thr Pro
565 570 575

Leu Ala Met Gly Ala Gly His Ile Asp Pro Asn Lys Ala Leu Asp Pro
580 585 590

Gly Leu Ile Tyr Asp Ala Thr Pro Gln Asp Tyr Val Asn Leu Leu Cys
595 600 605

Ala Leu Asn Phe Thr Ser Lys Gln Ile Gln Thr Ile Thr Arg Ser Ser
610 615 620

Thr Tyr Thr Cys Ser Asn Pro Ser Leu Asp Leu Asn Tyr Pro Ser Phe
625 630 635 640

Ile Gly Tyr Phe Asn Arg Asn Ser Ser Asp Ser Asp Pro Lys Arg Ile
645 650 655

Gln Glu Phe Ile Arg Thr Val Thr Asn Leu Gln Asp Gly Thr Ser Val
660 665 670

Tyr Thr Ala Lys Ile Thr Pro Met Gly Lys Phe Lys Val Ser Val Val
675 680 685

Pro Asn Lys Leu Ile Phe Lys Glu Lys Tyr Glu Lys Gln Ser Tyr Lys
690 695 700

Leu Arg Ile Glu Gly Pro Ile Ile Met Asp Asp Ile Val Val Asp Gly
705 710 715 720

Ser Leu Ser Trp Met Glu Thr Arg Gly Lys Tyr Ile Val Lys Ser Pro
725 730 735

Ile Val Ala Thr Ser Ile Arg Val Asp Pro Leu Arg Gly His Asn
740 745 750

<210> SEQ ID NO 23
<211> LENGTH: 2256
<212> TYPE: DNA
<213> ORGANISM: Solanum tuberosum

<400> SEQUENCE: 23
atggcaaatc atattgcctt gtgtatttgg ttgctttcta taattcaatt ggcaaagtca 60
gaaacttata tcattcatat ggatttgtca gccatgccaa aagctttttc tagccatcat 120
aattggtact tgactacact ttcttctgta tcagatagca aagacttgtt gtcctctaaa 180
ctagtttata cttatactaa tgccatcaat ggtttcagtg caagtctttc tccttctgag 240
atagaagcta ttaagaattc tcccggctat gtttcttcga ttaaggatat gtcggttaaa 300
gttgacacaa ctcacacatc tcaattcctt ggccttaact ctgagtctgg tgtatggcca 360
aagtctgatt atggcaaaga tgtcatagtt ggattagttg acactgggat atggccagag 420
agtagaagtt atagtgatga tgggatgaat gaagtaccat caagatggaa aggagaatgt 480
gaaagtggaa ctcagttcaa ttcctctttg tgcaataaga aactcattgg cgctcgttac 540

```
ttcaataaag gcctacttgc taacaacccg aatcttacca tttcgatgga ttcttctcgt    600

gatacggatg gacatgggac tcatacttct tccacggctg ctggaagtcg tgtagagggt    660

gcatcttttt ttggctatgc cgctggaaca gctacaggtg tagcaccaaa ggctcatgtg    720

gccatgtaca aggctctatg ggaagaaggt gtattcttgt ctgatattct tgcagcaatt    780

gatcaagcaa ttgaagatgg tgtagatgta ttgtcgttgt cattaggcat tgacgcgctt    840

ccattatacg aagatcctgt tgcaattgct gcatttgctg cactggagaa aggcatattt    900

gtttctacat ctgcaggaaa tgaagggcca tttttggaaa ctttgcacaa tggaacacct    960

tgggtgctca ctgttgctgc tggcacggtt gaccgtgagt ttattggcac actaacactt   1020

ggaaatggag tttcggtcac tggattatcg ctctaccctg ggaattctag ttcaagtgaa   1080

cgctccatta gctatgttga ttgccaagat gataaggaac tgcagaaaaa tgcacacaaa   1140

atagtggtct gcattgacaa gagtgattca gttagcgaag acgtctacaa tgtaagaaat   1200

tcaaaagttt ctggtgcagt cttcataact aattcaactg acttggaatt ctacctccaa   1260

agtgaatttc ctgcagtgtt tttgaacatt caagagggtg ataaagttct tgagtatgtt   1320

aggagtgagg ctgcacctaa cgcaaagctt gaattccaag tgacgcgtat tggtgctaaa   1380

ccagcaccaa aagttgctag ctatagctca agaggaccat caccaagttg tcctataatt   1440

ctcaagcctg acctcatggg tcctggtgcc ttaatacttg cttcatggcc acaacaaaca   1500

ccagtaactg aagttacctc aggaaaactt tatagtaact tcaacattat atcaggcaca   1560

tcaatgtctt gtccacatgc ttctggtgta gcagcacttc taaaaagtgc acaccctgaa   1620

tggagccctg ctgctatccg atccgccatg atgaccacag cctatgtatt ggacaacaca   1680

caaagcccca tccaagacat aggtttgaag aatggtgttg ctactcctct agctatggga   1740

gctggccata tcgatccaaa caaggcgttg gatcccggac tcatctatga tgcaacacca   1800

caagattatg ttaatctcct ttgtgctttg aacttcacat ccaaacaaat acaaaccatc   1860

acaagatcct caacttacac ttgctccaac ccatcattag acttgaacta tccatctttc   1920

attggctatt tcaaccggaa cagcagcgat tcagatccta aaaggattca agaattcata   1980

agaacagtga caaacttaca agatggtaca tcagtataca cagcaaagat cactccaatg   2040

ggtaaattta aagttagtgt tgtacctaat aagttgattt tcaaagaaaa gtatgaaaag   2100

caaagctaca agctaagaat agaaggtcca ataattatgg atgatattgt ggttgatggt   2160

tccttgagtt ggatggaaac tagaggaaaa tacatagtca aaagtccaat tgttgcaaca   2220

agtataagag tggatccttt gagaggacat aactga                              2256
```

<210> SEQ ID NO 24
<211> LENGTH: 477
<212> TYPE: PRT
<213> ORGANISM: Artificial Sequence
<220> FEATURE:
<223> OTHER INFORMATION: Antibody construct 2G12HC

<400> SEQUENCE: 24

```
Met Ala Asn Lys His Leu Ser Leu Ser Leu Phe Leu Val Leu Leu Gly
1               5                   10                  15

Leu Ser Ala Ser Leu Ala Ser Gly Glu Val Gln Leu Val Glu Ser Gly
            20                  25                  30

Gly Gly Leu Val Lys Ala Gly Gly Ser Leu Ile Leu Ser Cys Gly Val
        35                  40                  45

Ser Asn Phe Arg Ile Ser Ala His Thr Met Asn Trp Val Arg Arg Val
```

-continued

```
    50                  55                  60

Pro Gly Gly Gly Leu Glu Trp Val Ala Ser Ile Ser Thr Ser Ser Thr
65                  70                  75                  80

Tyr Arg Asp Tyr Ala Asp Ala Val Lys Gly Arg Phe Thr Val Ser Arg
                85                  90                  95

Asp Asp Leu Glu Asp Phe Val Tyr Leu Gln Met His Lys Met Arg Val
            100                 105                 110

Glu Asp Thr Ala Ile Tyr Tyr Cys Ala Arg Lys Gly Ser Asp Arg Leu
        115                 120                 125

Ser Asp Asn Asp Pro Phe Asp Ala Trp Gly Pro Gly Thr Val Val Thr
    130                 135                 140

Val Ser Pro Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Phe Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475
```

<210> SEQ ID NO 25
<211> LENGTH: 1434
<212> TYPE: DNA
<213> ORGANISM: Artificial Sequence
<220> FEATURE:
<223> OTHER INFORMATION: Antibody construct 2G12HC

<400> SEQUENCE: 25
atggcgaaca aacacttgtc cctctccctc ttcctcgtcc tccttggcct gtcggccagc 60
ttggcctcag gtgaggtgca gctggtggag tctgggggag gcctggtcaa ggcgggagga 120
tccctcatac tctcctgtgg agtctctaat tttagaatct ctgcccatac catgaattgg 180
gtccgccggg ttccaggggg ggggctggag tgggtcgctt ccattagtac gagttccact 240
tatagagact atgcagacgc tgtgaagggc cgattcaccg tttccagaga cgacctcgaa 300
gactttgtgt atttgcaaat gcacaaaatg agagtcgaag acacggctat ttattactgc 360
gccagaaagg gatctgacag actaagcgac aacgatcctt ttgatgcctg gggccagga 420 acagtggtca ccgtctctcc cgcctccacc aagggcccat cggtcttccc cctggcaccc 480
tcctccaaga gcacctctgg gggcacagcg gccctgggct gcctggtcaa ggactacttc 540
cccgaaccgg tgacggtgtc gtggaactca ggcgccctga ccagcggcgt gcacaccttc 600
ccggctgtcc tacagtcctc aggactctac tccctcagca gcgtggtgac cgtgccctcc 660
agcagcttgg gcacccagac ctacatctgc aacgtgaatc acaagcccag caacaccaag 720
gtggacaaga aagttgagcc caaatcttgt gacaaaactc acacatgccc accgtgccca 780
gcacctgaac tcctgggggg accgtcagtc ttcctcttcc ccccaaaacc caaggacacc 840
ctcatgatct cccggacccc tgaggtcaca tgcgtggtgg tggacgtgag ccacgaagac 900
cctgaggtca agttcaactg gtacgtggac ggcgtggagg tgcataatgc caagacaaag 960
ccgcgggagg agcagtacaa cagcacgtac cgtgtggtca gcgtcctcac cgtcctgcac 1020
caggactggc tgaatggcaa ggagtacaag tgcaaggtct ccaacaaagc cttcccagcc 1080
cccatcgaga aaaccatctc caaagccaaa gggcagcccc gagaaccaca ggtgtacacc 1140
ctgcccccat cccgggatga gctgaccaag aaccaggtca gcctgacctg cctggtcaaa 1200
ggcttctatc ccagcgacat cgccgtggag tgggagagca atgggcagcc ggagaacaac 1260
tacaagacca cgcctcccgt gctggactcc gacggctcct tcttcctcta cagcaagctc 1320
accgtggaca agagcaggtg gcagcagggg aacgtcttct catgctccgt gatgcatgag 1380
gctctgcaca accactacac gcagaagagc ctctccctgt ctccgggtaa atga 1434

<210> SEQ ID NO 26
<211> LENGTH: 477
<212> TYPE: PRT
<213> ORGANISM: Artificial Sequence
<220> FEATURE:
<223> OTHER INFORMATION: Antibody construct 2G12HC (comprising an I19R mutation)

<400> SEQUENCE: 26

Met Ala Asn Lys His Leu Ser Leu Ser Leu Phe Leu Val Leu Leu Gly
1               5                   10                  15

Leu Ser Ala Ser Leu Ala Ser Gly Glu Val Gln Leu Val Glu Ser Gly
            20                  25                  30

Gly Gly Leu Val Lys Ala Gly Gly Ser Leu Arg Leu Ser Cys Gly Val
        35                  40                  45

-continued

```
Ser Asn Phe Arg Ile Ser Ala His Thr Met Asn Trp Val Arg Arg Val
    50                  55                  60

Pro Gly Gly Gly Leu Glu Trp Val Ala Ser Ile Ser Thr Ser Ser Thr
65                  70                  75                  80

Tyr Arg Asp Tyr Ala Asp Ala Val Lys Gly Arg Phe Thr Val Ser Arg
                85                  90                  95

Asp Asp Leu Glu Asp Phe Val Tyr Leu Gln Met His Lys Met Arg Val
            100                 105                 110

Glu Asp Thr Ala Ile Tyr Tyr Cys Ala Arg Lys Gly Ser Asp Arg Leu
        115                 120                 125

Ser Asp Asn Asp Pro Phe Asp Ala Trp Gly Pro Gly Thr Val Val Thr
    130                 135                 140

Val Ser Pro Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Phe Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
```

465 470 475

<210> SEQ ID NO 27
<211> LENGTH: 1434
<212> TYPE: DNA
<213> ORGANISM: Artificial Sequence
<220> FEATURE:
<223> OTHER INFORMATION: Antibody construct 2G12HC (comprising an I19R mutation)

<400> SEQUENCE: 27
atggcgaaca aacacttgtc cctctccctc ttcctcgtcc tccttggcct gtcggccagc 60
ttggcctcag gtgaggtgca gctggtggag tctgggggag gcctggtcaa ggcgggagga 120
tccctcagac tctcctgtgg agtctctaat tttagaatct ctgcccatac catgaattgg 180
gtccgccggg ttccaggggg ggggctggag tgggtcgctt ccattagtac gagttccact 240
tatagagact atgcagacgc tgtgaagggc cgattcaccg tttccagaga cgacctcgaa 300
gactttgtgt atttgcaaat gcacaaaatg agagtcgaag acacggctat ttattactgc 360
gccagaaagg gatctgacag actaagcgac aacgatcctt ttgatgcctg ggggccagga 420
acagtggtca ccgtctctcc cgcctccacc aagggcccat cggtcttccc cctggcaccc 480
tcctccaaga gcacctctgg gggcacagcg gccctgggct gcctggtcaa ggactacttc 540
cccgaaccgg tgacggtgtc gtggaactca ggcgccctga ccagcggcgt gcacaccttc 600
ccggctgtcc tacagtcctc aggactctac tccctcagca gcgtggtgac cgtgccctcc 660
agcagcttgg gcacccagac ctacatctgc aacgtgaatc acaagcccag caacaccaag 720
gtggacaaga aagttgagcc caaatcttgt gacaaaactc acacatgccc accgtgccca 780
gcacctgaac tcctgggggg accgtcagtc ttcctcttcc ccccaaaacc caaggacacc 840
ctcatgatct cccggacccc tgaggtcaca tgcgtggtgg tggacgtgag ccacgaagac 900
cctgaggtca agttcaactg gtacgtggac ggcgtggagg tgcataatgc caagacaaag 960
ccgcgggagg agcagtacaa cagcacgtac cgtgtggtca gcgtcctcac cgtcctgcac 1020
caggactggc tgaatggcaa ggagtacaag tgcaaggtct ccaacaaagc cttcccagcc 1080
cccatcgaga aaaccatctc caaagccaaa gggcagcccc gagaaccaca ggtgtacacc 1140
ctgcccccat cccgggatga gctgaccaag aaccaggtca gcctgacctg cctggtcaaa 1200
ggcttctatc ccagcgacat cgccgtggag tgggagagca atgggcagcc ggagaacaac 1260
tacaagacca cgcctcccgt gctggactcc gacggctcct tcttcctcta cagcaagctc 1320
accgtggaca agagcaggtg gcagcagggg aacgtcttct catgctccgt gatgcatgag 1380
gctctgcaca accactacac gcagaagagc ctctccctgt ctccgggtaa atga 1434

<210> SEQ ID NO 28
<211> LENGTH: 238
<212> TYPE: PRT
<213> ORGANISM: Artificial Sequence
<220> FEATURE:
<223> OTHER INFORMATION: Antibody construct 2G12LC

<400> SEQUENCE: 28

Met Ala Asn Lys His Leu Ser Leu Ser Leu Phe Leu Val Leu Leu Gly
1 5 10 15

Leu Ser Ala Ser Leu Ala Ser Gly Asp Val Val Met Thr Gln Ser Pro
20 25 30

Ser Thr Leu Ser Ala Ser Val Gly Asp Thr Ile Thr Ile Thr Cys Arg
35 40 45

```
Ala Ser Gln Ser Ile Glu Thr Trp Leu Ala Trp Tyr Gln Gln Lys Pro
    50                  55                  60

Gly Lys Ala Pro Lys Leu Leu Ile Tyr Lys Ala Ser Thr Leu Lys Thr
65                  70                  75                  80

Gly Val Pro Ser Arg Phe Ser Gly Ser Gly Ser Gly Thr Glu Phe Thr
                85                  90                  95

Leu Thr Ile Ser Gly Leu Gln Phe Asp Asp Phe Ala Thr Tyr His Cys
            100                 105                 110

Gln His Tyr Ala Gly Tyr Ser Ala Thr Phe Gly Gln Gly Thr Arg Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 29
<211> LENGTH: 717
<212> TYPE: DNA
<213> ORGANISM: Artificial Sequence
<220> FEATURE:
<223> OTHER INFORMATION: Antibody construct 2g12lc

<400> SEQUENCE: 29

```
atggcgaaca aacacttgtc cctctccctc ttcctcgtcc tccttggcct gtcggccagc      60

ttggcctcag gtgatgttgt gatgactcag tctccttcca ccctgtctgc atctgtcgga     120

gacacaatca ccatcacttg ccgggccagt cagagtattg aaacctggtt ggcctggtat     180

cagcagaagc cagggaaagc ccccaaactc ctaatctaca aggcgtctac tttaaaaact     240

ggagtcccgt caagattcag cggcagtgga tctggaacag agttcactct taccatcagt     300

ggcctgcagt tcgatgactt tgcaacttat cactgtcagc actatgctgg ttattcagcg     360

acgttcggcc aggggaccag ggtggagatc aaacgaactg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgttag       717
```

<210> SEQ ID NO 30
<211> LENGTH: 462
<212> TYPE: PRT
<213> ORGANISM: Artificial Sequence
<220> FEATURE:
<223> OTHER INFORMATION: Antibody construct 2F5 (heavy chain)

<400> SEQUENCE: 30

Arg Ile Thr Leu Lys Glu Ser Gly Pro Pro Leu Val Lys Pro Thr Gln
1 5 10 15

Thr Leu Thr Leu Thr Cys Ser Phe Ser Gly Phe Ser Leu Ser Asp Phe
20 25 30

Gly Val Gly Val Gly Trp Ile Arg Gln Pro Pro Gly Lys Ala Leu Glu
35 40 45

Trp Leu Ala Ile Ile Tyr Ser Asp Asp Asp Lys Arg Tyr Ser Pro Ser
50 55 60

Leu Asn Thr Arg Leu Thr Ile Thr Lys Asp Thr Ser Lys Asn Gln Val
65 70 75 80

Val Leu Val Met Thr Arg Val Ser Pro Val Asp Thr Ala Thr Tyr Phe
85 90 95

Cys Ala His Arg Arg Gly Pro Thr Thr Leu Phe Gly Val Pro Ile Ala
100 105 110

Arg Gly Pro Val Asn Ala Met Asp Val Trp Gly Gln Gly Ile Thr Val
115 120 125

Thr Ile Ser Ser Thr Ser Thr Lys Gly Pro Ser Val Phe Pro Leu Ala
130 135 140

Pro Ser Ser Lys Ser Thr Ser Gly Gly Thr Ala Ala Leu Gly Cys Leu
145 150 155 160

Val Lys Asp Tyr Phe Pro Glu Pro Val Thr Val Ser Trp Asn Ser Gly
165 170 175

Ala Leu Thr Ser Gly Val His Thr Phe Pro Ala Val Leu Gln Ser Ser
180 185 190

Gly Leu Tyr Ser Leu Ser Ser Val Val Thr Val Pro Ser Ser Ser Leu
195 200 205

Gly Thr Gln Thr Tyr Ile Cys Asn Val Asn His Lys Pro Ser Asn Thr
210 215 220

Lys Val Asp Lys Lys Val Glu Pro Lys Ser Cys Asp Lys Thr His Thr
225 230 235 240

Cys Pro Pro Cys Pro Ala Pro Glu Leu Leu Gly Gly Pro Ser Val Phe
245 250 255

Leu Phe Pro Pro Lys Pro Lys Asp Thr Leu Met Ile Ser Arg Thr Pro
260 265 270

Glu Val Thr Cys Val Val Val Asp Val Ser His Glu Asp Pro Glu Val
275 280 285

Lys Phe Asn Trp Tyr Val Asp Gly Val Glu Val His Asn Ala Lys Thr
290 295 300

Lys Pro Arg Glu Glu Gln Tyr Asn Ser Thr Tyr Arg Val Val Ser Val
305 310 315 320

Leu Thr Val Leu His Gln Asp Trp Leu Asn Gly Lys Glu Tyr Lys Cys
325 330 335

Lys Val Ser Asn Lys Ala Phe Pro Ala Pro Ile Glu Lys Thr Ile Ser
340 345 350

Lys Ala Lys Gly Gln Pro Arg Glu Pro Gln Val Tyr Thr Leu Pro Pro
355 360 365

Ser Arg Asp Glu Leu Thr Lys Asn Gln Val Ser Leu Thr Cys Leu Val
370 375 380

Lys Gly Phe Tyr Pro Ser Asp Ile Ala Val Glu Trp Glu Ser Asn Gly
385 390 395 400

Gln Pro Glu Asn Asn Tyr Lys Thr Thr Pro Pro Val Leu Asp Ser Asp
405 410 415

```
Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460


<210> SEQ ID NO 31
<211> LENGTH: 453
<212> TYPE: PRT
<213> ORGANISM: Artificial Sequence
<220> FEATURE:
<223> OTHER INFORMATION: Antibody construct I19R 2G12 (heavy chain)

<400> SEQUENCE: 31

Glu Val Gln Leu Val Glu Ser Gly Gly Gly Leu Val Lys Ala Gly Gly
1               5                   10                  15

Ser Leu Arg Leu Ser Cys Gly Val Ser Asn Phe Arg Ile Ser Ala His
            20                  25                  30

Thr Met Asn Trp Val Arg Arg Val Pro Gly Gly Gly Leu Glu Trp Val
        35                  40                  45

Ala Ser Ile Ser Thr Ser Ser Thr Tyr Arg Asp Tyr Ala Asp Ala Val
    50                  55                  60

Lys Gly Arg Phe Thr Val Ser Arg Asp Asp Leu Glu Asp Phe Val Tyr
65                  70                  75                  80

Leu Gln Met His Lys Met Arg Val Glu Asp Thr Ala Ile Tyr Tyr Cys
                85                  90                  95

Ala Arg Lys Gly Ser Asp Arg Leu Ser Asp Asn Asp Pro Phe Asp Ala
            100                 105                 110

Trp Gly Pro Gly Thr Val Val Thr Val Ser Pro Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320
```

```
Asn Gly Lys Glu Tyr Lys Cys Lys Val Ser Asn Lys Ala Phe Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 32
<211> LENGTH: 466
<212> TYPE: PRT
<213> ORGANISM: Artificial Sequence
<220> FEATURE:
<223> OTHER INFORMATION: Antibody construct PG9 (heavy chain)

<400> SEQUENCE: 32

Gln Arg Leu Val Glu Ser Gly Gly Gly Val Val Gln Pro Gly Ser Ser
1               5                   10                  15

Leu Arg Leu Ser Cys Ala Ala Ser Gly Phe Asp Phe Ser Arg Gln Gly
            20                  25                  30

Met His Trp Val Arg Gln Ala Pro Gly Gln Gly Leu Glu Trp Val Ala
        35                  40                  45

Phe Ile Lys Tyr Asp Gly Ser Glu Lys Tyr His Ala Asp Ser Val Trp
    50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
            100                 105                 110

Phe Tyr Asp Gly Tyr Tyr Asn Tyr His Tyr Met Asp Val Trp Gly Lys
        115                 120                 125

Gly Thr Thr Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220
```

```
Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 33
<211> LENGTH: 120
<212> TYPE: PRT
<213> ORGANISM: Artificial Sequence
<220> FEATURE:
<223> OTHER INFORMATION: Protease inhibitor

<400> SEQUENCE: 33

```
Met Met Lys Lys Asp Gln Ile Leu Ser Ser Ile Leu Leu Phe Phe Phe
1               5                   10                  15

Leu Phe Thr Ala Phe Ile Thr Thr Met Ala Asp Ser Gln Ala Ser Ser
            20                  25                  30

Gln Pro Ser Asn Glu Ser Lys Val His Ile Val Tyr Thr Glu Gln Pro
        35                  40                  45

Lys Asp Gln Glu Pro Glu Glu Tyr His Ile Lys Thr Leu Thr Ser Val
    50                  55                  60

Leu Gly Ser Glu Glu Ala Ala Lys Glu Ala Leu Leu Tyr Ser Tyr Lys
65                  70                  75                  80

His Ala Ala Ser Gly Phe Ser Ala Lys Leu Thr Ala Glu Gln Val Ser
                85                  90                  95

Glu Leu Ser Lys Leu Pro Gly Val Leu Gln Val Val Pro Ser Gln Thr
            100                 105                 110
```

```
Val Gln Leu His Thr Gly Arg Val
        115                 120


<210> SEQ ID NO 34
<211> LENGTH: 102
<212> TYPE: PRT
<213> ORGANISM: Artificial Sequence
<220> FEATURE:
<223> OTHER INFORMATION: Protease inhibitor

<400> SEQUENCE: 34

Met Gln Lys Ile Gln Ile Ile Phe Leu Val Phe Leu Leu Leu Phe Val
1               5                   10                  15

Ala Asp Cys Glu Glu Ala Lys Val Tyr Ile Val Phe Thr Glu Asn Pro
            20                  25                  30

Gln Pro Lys Glu Phe His Ile Lys Thr Leu Ala Ser Val Leu Gly Ser
        35                  40                  45

Glu Asp Ala Ala Arg Glu Ala Leu Ile Tyr Ser Tyr Lys His Val Ile
    50                  55                  60

Ser Gly Phe Ala Ala Arg Leu Thr Pro Glu Gln Val Ser Glu Leu Ala
65                  70                  75                  80

Lys Lys Pro Gly Val Leu Glu Ile Val Pro Ser Arg Thr Tyr His Leu
                85                  90                  95

Asp Gly Pro Lys Leu Lys
            100


<210> SEQ ID NO 35
<211> LENGTH: 6
<212> TYPE: PRT
<213> ORGANISM: Artificial Sequence
<220> FEATURE:
<223> OTHER INFORMATION: Tag

<400> SEQUENCE: 35

His His His His His His
1               5


<210> SEQ ID NO 36
<211> LENGTH: 12
<212> TYPE: PRT
<213> ORGANISM: Artificial Sequence
<220> FEATURE:
<223> OTHER INFORMATION: gp41 peptide

<400> SEQUENCE: 36

Gly Gly Gly Leu Glu Leu Asp Lys Trp Ala Ser Leu
1               5                   10


<210> SEQ ID NO 37
<211> LENGTH: 9
<212> TYPE: PRT
<213> ORGANISM: Artificial Sequence
<220> FEATURE:
<223> OTHER INFORMATION: fluorigenic peptide substrate
<220> FEATURE:
<221> NAME/KEY: MOD_RES
<222> LOCATION: (1)..(1)
<223> OTHER INFORMATION: aminobenzoic acid (Abz) functional group
<220> FEATURE:
<221> NAME/KEY: MOD_RES
<222> LOCATION: (9)..(9)
<223> OTHER INFORMATION: Nitro (NO2) functional group
```

-continued

<400> SEQUENCE: 37

```
Val Ile Leu Asp Ala Val Arg Ala Tyr
1               5
```

PLANT SERINE PROTEASES

INCORPORATION-BY-REFERENCE OF MATERIAL SUBMITTED ELECTRONICALLY

Incorporated by reference in its entirety herein is a computer-readable sequence listing and identified as follows: One 139,104 Byte ASCII (Text) file named "Sequence_Listing_ST25.txt," created on Dec. 26, 2023.

TECHNICAL FIELD

The present invention relates to the field of the production of recombinant proteins and other polypeptides in plants.

BACKGROUND ART

Many proteins, in particular in eukaryotic systems, are susceptible to proteolytic enzymes (proteases).

Unwanted proteolysis is important because it may alter physical and chemical properties, conformation, distribution, stability, activity, folding and consequently, function of the proteins. Moreover, many proteins show significantly less or no activity when they are modified by proteases. Secreted proteins, membrane proteins and proteins targeted to vesicles or certain intracellular organelles are likely to be exposed to proteases during their biosynthesis or post harvesting. Types of human proteins which often undergo proteolysis include serum proteins, antibodies, metal carriers, enzymes, coagulation factors, protease inhibitors, extracellular matrix proteins, growth factors and hormones. The sequences targeted by the proteases sometimes contain the amino acids lysine or arginine at the two positions preceding the cleaved peptide bond. However, other sequence motifs recognized by proteases are also known. The proteases responsible for these cleavage reactions are typically derived from extracellular fluids or components of the secretory machinery of eukaryotic cells (e.g. Golgi apparatus, lysosomes or related compartments).

Proteases as well as their regulation play an important role in tobacco plants for modulating the curing of the leaves of said tobacco plants (see WO 2016/009006). Controlling the expression of subtilisin-like serine endopeptidase-like proteins in plants allows the manipulation of water and/or $CO_2$ exchange through plant stomata (see WO 2013/192545).

As mentioned above the preservation of the full-length sequence is often essential for the biological activity of polypeptides and proteins. This has to be considered when host cells are selected to be used for the recombinant production of polypeptides and proteins.

US 2004/106198 discloses a system for the expression of heterologous protease sensitive proteins in a plant cell.

Especially the recombinant expression of animal polypeptides and proteins in plants or plant cells often requires a modification of the host cell to prevent proteolysis of the polypeptides and proteins to be expressed. However, targeted strategies to protect recombinantly produced proteins of animal origin in plant cells against proteolytic degradation depend on knowledge of the responsible proteases, which have not been identified yet.

It is therefore an object of the present invention to provide methods and means enabling a host cell, preferably of non-animal origin, to prevent the unwanted proteolysis of a recombinant protein, preferably derived from an animal, based on the identity and properties of the proteases involved therein.

SUMMARY OF THE INVENTION

The present invention relates to a genetically modified plant or plant cell derived from a wild-type plant or plant cell, said wild-type plant or plant cell producing at least one serine protease comprising the motif $SSRGPX_1LKPDX_2X_3APGX_4SGTSMSCPHX_5PX_6WSPX_7AX_8X_9SAX_{10}MTT$ (SEQ ID No. 1), wherein $X_1$ is a peptide consisting of 7 amino acid residues, Xe is I or L, $X_3$ is T or M, $X_4$ is a peptide consisting of 27 or 28 amino acid residues, $X_5$ is a peptide consisting of 12 amino acid residues, $X_6$ is T or E, $X_7$ is S or A, $X_8$ is V or I, $X_9$ is K or R and $X_{10}$ is I or M, wherein the proteolytic activity of the at least one serine protease in the genetically modified plant or plant cell is reduced compared to its activity in the wild-type plant or plant cell, wherein the genetically modified plant or plant cell comprises at least one exogenous nucleic acid molecule encoding for at least one protein or polypeptide of interest. It turned surprisingly out that proteolysis of proteins and polypeptides recombinantly produced in plant cells could be significantly reduced or even completely prevented when the activity of at least one serine protease as mentioned above is significantly reduced or prevented.

Another aspect of the present invention relates to a serine protease consisting of an amino acid sequence selected from the group consisting of SEQ ID No. 2, SEQ ID No. 4, SEQ ID No. 6, SEQ ID No. 8, SEQ ID No. 10, SEQ ID No. 14, SEQ ID No. 16, SEQ ID No. 20 and SEQ ID No. 22, preferably SEQ ID No. 2 or SEQ ID No. 14.

A further aspect of the present invention relates to a nucleic acid molecule encoding a serine protease according to the present invention.

Another aspect of the present invention relates to a method for producing at least one protein or polypeptide of interest by cultivating a genetically modified plant or plant cell according to the present invention.

DESCRIPTION OF EMBODIMENTS

Figure 1:
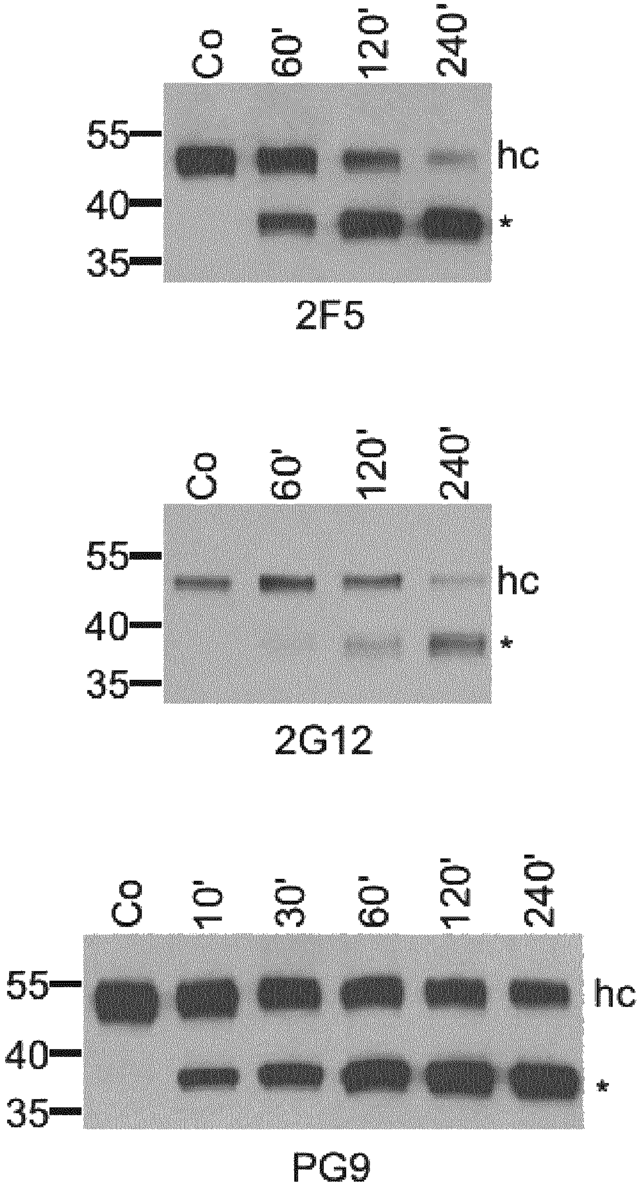
FIG. 1 shows the time-dependent degradation of 2F5, 2G12 and PG9 by proteases present in apoplastic fluid obtained from *Nicotiana benthamiana* C105 leaves. A characteristic heavy-chain (hc) degradation product (*) is produced due to cleavage within or close to the complementarity-determining region (CDR) H3 loop. The identified cleavage sites are shown in Table 1.

The reduction of the proteolytic activity of the at least one serine protease of the present invention comprising the motif consisting of SEQ ID No. 1 in plants and plant cells resulted surprisingly in a reduction of the proteolysis of exogenous polypeptides and proteins synthesised in said plants and plant cells.

Serine proteases are able to cleave peptide bonds in proteins and polypeptides, in which serine serves as the nucleophilic amino acid at the enzyme's active site. Serine proteases are characterised by a distinctive structure, consisting of two domains that converge at the catalytic active site. Furthermore, these proteases are usually categorised based on their substrate specificity as either trypsin-like, chymotrypsin-like, thrombin-like, subtilisin-like or elastase-like. The serine proteases of the present invention whose proteolytic activity shall be reduced are preferably subtilisin-like serine proteases.

According to a preferred embodiment of the present invention the protease is a plant protease, preferably a serine protease, more preferably a subtilisin-like serine protease, preferably from *Nicotiana* spp., more preferably from *Nicotiana benthamiana*, in particular from the *Nicotiana benthamiana* line C105 (Strasser R et al. Plant Biotechnol J 6(2008):392-402).

The term "plant cell", as used herein, refers to protoplasts, gamete producing cells and cells which regenerate into whole plants. Plant cells, as used herein, further include cells obtained from or found in seeds, suspension cultures, embryos, meristematic regions, callus tissue, leaves, roots, shoots, gametophytes, sporophytes, pollen and microspores.

"Proteolytic activity" of enzymes refers to their ability to cleave peptide bonds present in polypeptides and proteins. Proteolytic activity can be measured by using methods known in the art (e.g. Twining, 1984, Anal. Biochem. 143, 30-34).

The serine protease motif of the present invention having SEQ ID No. 1 comprises at positions $X_1$, $X_4$ and $X_5$ peptides consisting of a defined length. However, the composition of these peptides in relation to amino acid residues is variable.

The motif of the serine protease of the present invention is $SSRGPX_1LKPDX_2X_3APGX_4SGTSMSCPHX_5PX_6$ $WSPX_7AX_8X_9SAX_{10}MTT$ (SEQ ID No. 1), wherein $X_1$ is a peptide consisting of 7 amino acid residues, $X_2$ is I or L, $X_3$ is T or M, $X_4$ is a peptide consisting of 27 or 28 amino acid residues, $X_5$ is a peptide consisting of 12 amino acid residues, $X_6$ is T or E, $X_7$ is S or A, Xe is V or I, $X_9$ is K or R and $X_{10}$ is I or M.

According to another preferred embodiment of the present invention the at least one serine protease has at least 80%, preferably at least 85%, more preferably at least 90%, more preferably at least 95%, more preferably at least 96%, more preferably at least 98%, more preferably at least 99%, in particular 100%, sequence identity to a serine protease consisting of an amino acid sequence selected from the group consisting of SEQ ID No. 2, SEQ ID No. 4, SEQ ID No. 6, SEQ ID No. 8, SEQ ID No. 10, SEQ ID No. 14, SEQ ID No. 16, SEQ ID No. 18, SEQ ID No. 20 and SEQ ID No. 22, most preferably SEQ ID No. 2 or SEQ ID No. 14.

"% sequence identity", as used herein, is obtained by aligning two sequences to be compared to give a maximum correlation between the sequences. This may include inserting "gaps" in either one or both sequences, to enhance the degree of alignment. A % identity may then be determined over the whole length of each of the sequences being compared. In the above context, an amino acid sequence having a "sequence identity" of at least, for example, 80% to a query amino acid sequence, is intended to mean that the sequence of the subject amino acid sequence is identical to the query sequence except that the subject amino acid sequence may include up to twenty amino acid alterations per each 100 amino acids of the query amino acid sequence. In other words, to obtain an amino acid sequence having a sequence of at least 80% identity to a query amino acid sequence, up to 20% (20 of 100) of the amino acid residues in the subject sequence may be inserted or substituted with another amino acid or deleted.

Methods for comparing the identity of two or even more sequences are well known in the art. The percentage to which two sequences are identical can for example be determined by using a mathematical algorithm. Such algorithms are integrated in the BLAST family of programs, e.g. BLAST or NBLAST program (see also Altschul et al., 1990, J. Mol. Biol. 215, 403-410 or Altschul et al., 1997, Nucleic Acids Res., 25, 3389-3402), accessible through the home page of the NCBI (ncbi.nlm.nih.gov). According to the present invention sequence identity is preferably determined using the following parameters: Matrix BLOSUM62; Open gap 11 and extension gap 1 penalties; gap x_dropoff50; expect 10.0 word size 3; Filter: none.

According to a further preferred embodiment of the present invention the protease is encoded by a nucleic acid sequence selected from the group consisting of SEQ ID No. 3, SEQ ID No. 5, SEQ ID No. 7, SEQ ID No. 9, SEQ ID No. 11, SEQ ID No. 15, SEQ ID No. 17, SEQ ID No. 19, SEQ ID No. 21 and SEQ ID No. 23, preferably SEQ ID No. 3 or SEQ ID No. 15.

Particularly preferred is a *Nicotiana benthamiana* subtilisin-like serine protease (SBT1) comprising amino acid sequence SEQ ID No. 2, whereby amino acid residues 1 to 150, preferably 1 to 140, more preferably 1 to 130, more preferably 1 to 120, more preferably 1 to 110, in particular 1 to 109, of SEQ ID No. 2 represent the signal peptide and propeptide region. The amino acids of the catalytic triad (Asp148, His215, Ser553) are underlined:

(SEQ ID No. 2)

MKGIISLFFCFSLFIVSFILREADSASQAQNNGIYIVYMGAAASSNGGTR

HDQARLISSLIRRNKHAVVHSYNNGFSGFAARLSESEAKSMAQRPGVISV

FPDPVLQLHTTHSWDFLKYQTDEKINSSPSSGSDSSLIGADTIIGILDTG

IWPESESFNDKDMGPIPSRWNGTCMDGQDFGSSKCNKKIVGARFYEESDD

SGTKIAGSARDENGHGTHVASTAAGSPVAGASYYGLAAGTATGGSPGSRI

SMYRVCTTFGCRGSAIMKAFDDAIADGVDVLSLSLGSSPGLEPDFPSNPI

AIGAFHAVEKGITVVCSAGNSGPGPKTVVNTAPWILTVAATTIDRDFETD

IVLGGNKLIKGGGINFGNMTKSSVYPLIHGNSTKSNDNVSEADARSCVPG

SLDENKVKGKIVLCENLDDGEYFPSDKLDEVKSRGGVGFILIDDDERTVA

PKFNSFSAGVVSKKDGNEILAYINSTRNPVASILPTVSITKYKPAPVVAY

FSSRGPAYNTPNLLKPDITAPGVAILAAWPGNDTSEALPGQKPPIFNLLS

GTSMSCPHVSGIAATVKAVNPTWSPSAVKSAIMTTAIQTNNLKAPITTVS

GSKATPYDIGAGEASTSGPLKPGLVYETDVADYLQFLCSVGFNISQIKLI

-continued

```
SITVPEDFSCPKNSTSELVSNMNYPSIAISSLKENEPKKVTRTVTNTGEE

ASVYTTVIEAPKGLEVQVIPTKLEFTNKSKKLSYDVSFKASSTSKEDLFG

SITWTNGKYKVRSPFVVSSN
```

A nucleic acid sequence encoding the *Nicotiana benthamiana* subtilisin-like serine protease may comprise SEQ ID No. 3, whereby nucleotide residues 1 to 450, preferably 1 to 420, more preferably 1 to 390, more preferably 1 to 360, more preferably 1 to 330, in particular 1 to 327, of SEQ ID No. 3 encode the signal peptide and the propeptide region:

```
                                         (SEQ ID No. 3)
atgaaaggaattatatctttgtttttctgcttttctcttttcattgtctc

tttcatattaagagaagccgactcagcttctcaagcacaaaacaatggaa

tttatattgtttatatgggtgctgcagcttcatctaatggtggtaccaga

catgatcaagcgcggcttatcagctccttgatcagaaggaacaagcatgc

agtggtacacagctacaacaatggtttctcaggattcgcggcacgtttat

cagaatctgaagctaaatccatggctcaaagacctggagttatctccgta

tttcctgatccagtactgcaactccacactacacattcatgggatttctt

gaagtatcaaactgatgaaaaaatcaattcaagtccaagctctggttctg

attcatcattaattggagctgataccataattggcatattggatacgggt

atatggccagaatctgagagtttcaatgacaaggatatgggtccaattcc

atcccggtggaatggaacttgcatggatggtcaagattttggctcttcaa

aatgcaacaagaagatagttggtgcaagattttatgaggagtctgatgac

agtggaacaaaaatcgctggatcagccagggacgagaacggacatggtac

tcatgttgcgtctactgcagctgggagtcctgttgcaggtgcatcctact

atggcctagctgcaggaactgccacgggtggatctcctggttcgaggatt

tccatgtatcgtgtctgtactacttttggatgccgcggatcagctatcat

gaaagcattcgatgatgcaattgcagatggggttgatgttttatcactat

cacttggttcatcacctggacttgaacctgattttccaagcaatcctatt

gccataggagcatttcatgctgtagaaaagggcattactgttgtttgctc

tgctggaaatagtggccctggaccaaaaactgttgtcaatacagctcctt

ggattcttactgttgcagccaccaccattgatcgtgacttcgagacagat

attgtcttgggtggaaacaagcttattaagggtggaggtataaactttgg

taacatgacaaaatcgtcagtctaccctttgattcatggcaattcaacca

aatcaaacgataatgtttctgaggcggatgcaaggagttgtgttcctggt

tcattagatgaaaacaaagtcaaggggaagattgtcctttgtgaaaatct

tgatgatggtgaatattttcccagtgacaagctagatgaagtgaaaagcc

gaggtggagttggatttatacttatagatgatgatgaaagaactgtggca

cccaaattcaattccttctcagctggtgtagtctctaaaaaggatggaaa

tgagatcctcgcctacattaactcgacgaggaatccagttgcatcaattt

taccaactgtatccataacaaagtacaaaccagctccagttgtggcttac

ttctcatcaagaggccctgcgtacaacacccctaacctcctcaaaccgga

tattacagcaccaggggttgccattcttgctgcttggcctggaaatgaca
```

-continued

```
cgagtgaggctctccccggccaaaaaccaccaattttcaacctactctca

ggcacttccatgtcctgccctcatgtatccggtattgctgctactgtcaa

agcagtaaaccctacctggagtccttcagctgtcaaatcagctattatga

ccacagctattcagacaaacaatttgaaggctccaatcactacagtctca

ggatccaaagcaacaccatatgacataggtgcaggagaagcaagcacttc

aggtccattaaaaccaggtctagtctacgagacagatgtcgccgactact

tgcagttcctatgttctgttggttttaacatatcacagataaagctgatc

tcaattacagttcctgaagacttttcatgcccaaaaaactcaacctctga

attggtttctaatatgaattatccatcaatagctatttctagtctcaaag

aaaacgagccgaagaaagttactagaactgtaacaaatactggtgaagaa

gcatcagtatatactacagttattgaggcaccaaaaggattggaagtcca

agtgatcccaactaaattggaatttacaaataaaagcaagaaattaagct

atgatgtgtctttcaaagcttcatctacctcaaaggaagatctgtttgga

tcaattacttggactaatggtaagtacaaagtccggagtccattcgtcgt

aagtagcaactaa
```

Particularly preferred is a *Nicotiana tabacum* sequence SEQ ID No. 4, whereby amino acid residues 1 to 150, preferably 1 to 140, more preferably 1 to 130, more preferably 1 to 120, more preferably 1 to 110, in particular 1 to 107, of SEQ ID No. 4 represent the signal peptide and propeptide region:

```
                                         (SEQ ID No. 4)
MKGLSLFFCFSLFIVAFIREADSASQAQNNGIYIVYMGAAASSNGGTRHD

QAQLISSLIRRNKNAVVHSYNNGFSGFAARLSEAEAKSMAQRPGVISVFP

DPVLQLHTTHSWDFLKYQTDEKINSSPSSGSDSSLIGADTIIGILDTGIW

PESESFNDKDMGPIPARWNGTCMDGQDFGSSKCNKKIVGARFYEESDDSG

IKIAGSARDENGHGTHVASTAAGSPVAGASYYGLAAGTATGGSPGSRIAM

YRVCTTFGCRGSAIMKAFDDAIADGVDVLSLSLGSSPGLEPDFPSNPIAI

GAFHAVEKGIVVVCSAGNSGPGPKTVVNTAPWILTVAATTIDRDFETDIV

LGGNKLIKGGGINFGNMTKSSVYPLIHGNSTKSNNNVSEADARSCVPGSL

DENKVKGKIVLCENLDDGEYFPSDKLDEVKSRGGVGFILIDDDERTVAPK

FNSFPAGVVSKKDGTEILAYINSTRNPIASILPTVSITKYKPAPVVAYFS

SRGPAYNTPNLLKPDITAPGVAILAAWPGNDTSEALPGQKPPIFNLLSGT

SMSCPHVSGIAATVKAVNPAWSPSAVKSAIMTTAIQINNLKAPITTVSGS

KATPYDIGAGEASTSGPLKPGLVYETDVADYLQFLCSAGFNISQIKLISS

TVPKDFSCPKNPTSELVSNMNYPSIAISSLKENEPKKVTRTVTNTGEEAS

VYTAIIEAPKGLEVQVIPSKLEFNYKSKKLSYEVSFKASSPSKEDLFGSI

TWTNGKYKVRSPFVVSSN
```

A nucleic acid sequence encoding the *Nicotiana tabacum* subtilisin-like serine protease may comprise SEQ ID No. 5, whereby nucleotide residues 1 to 450, preferably 1 to 420, more preferably 1 to 390, more preferably 1 to 360, more preferably 1 to 330, in particular 1 to 321, of SEQ ID No. 5 encode the signal peptide and the propeptide region:

(SEQ ID No. 5)
atgaaaggcctttctttgttcttctgcttttctcttttcattgtcgcttt cataagagaagccgactcagcttctcaagcacaaaacaatggcatttata ttgtttatatgggtgctgcggcttcttctaacggtggtaccagacatgat caagcgcagcttatcagctccttgatcagaaggaacaagaatgcagtggt acacagctacaacaatggtttctcaggattcgcggcacgtttatcagaag ctgaagctaaatccatggctcaaagacctggagttatctctgtatttcct gatccagtactgcaactccacactacacattcatgggatttcttgaagta tcaaactgatgaaaaaatcaattcaagtccaagctctggttctgattcat cattaattggagctgataccataattggcatattggatacgggtatatgg ccagaatctgagagtttcaatgacaaggatatgggtccaattccagcccg gtggaatggaacttgcatggatggtcaagattttggctcttcaaaatgca acaagaagatagttggtgcaagattttatgaggagtctgatgacagtgga ataaaaatcgctggatcagccagggacgagaacggacatggtactcatgt tgcgtctactgcagctgggagtcctgttgcaggtgcatcctactatggcc tagctgcaggaactgccacgggtggatctcctggttcaaggattgccatg tatcgtgtctgtactacttttggatgccgtggatcagctatcatgaaagc attcgatgacgcaattgcagatggggttgatgttttatcactatcacttg gttcatcacccggacttgaacctgattttccgagcaatcctattgccata ggagcatttcatgccgtagaaaagggcattgttgttgtttgctctgctgg aaatagtggccctggcccaaaaactgttgtcaatacagctccttggattc taacggttgcagccaccaccattgatcgtgacttcgagacagatattgtc ttgggtggaaacaagcttattaagggtggaggtataaactttggtaacat gacaaaatcgtcagtctaccctttgattcatggcaattcaaccaaatcaa acaataatgtttctgaggcggatgcaaggagttgtgttcctggttcatta gatgaaaacaaagtcaaggggaagattgttctttgtgaaaatcttgatga tggcgaatattttcccagtgacaagctagacgaagtgaagagtcgaggtg gagttggatttatactaatagatgatgatgaaagaactgtggcacccaaa ttcaattccttcccagcaggtgtagtctctaaaaaggatggtactgagat ccttgcctacattaactcgactaggaatcccattgcatcaattttaccaa ctgtttccataacaaagtacaaaccagctccagttgtcgcttacttctca tcaagaggccctgcgtacaacacccctaacctcctcaaaccggatattac agcaccaggggttgccattcttgctgcttggcctggaaatgacacgagtg aggctctccccggccaaaaaccaccaattttcaacctactctcaggcact tccatgtcctgccctcacgtatccggtattgctgcaactgtcaaagcagt taaccctgcctggagtccttcagctgtcaaatcagctattatgaccacag ctattcagataaacaatttgaaggctccaatcactacagtctcaggatcc aaagcaacaccatatgacataggtgcaggagaagcaagcacttcaggtcc attaaaaccaggtctagtctacgagacagatgtcgccgactacttgcagt tcctatgttctgctggctttaacatatcacagataaagctgatctcaagt acagttcctaaggacttttcatgcccaaaaaacccaacctctgaattggt -continued ttctaatatgaattatccatcaatagctatttctagtctcaaagaaaacg agccgaagaaagttactagaacagttacaaatactggtgaagaagcatca gtatatactgcaatcattgaggcaccaaaaggattggaagtccaagtgat tccaagtaaattggaatttaattataaaagcaagaaattaagctatgaag tgtctttcaaagcttcatctccctcaaaggaggatctgtttggctcaatt acttggacaaatggtaagtacaaagtccggagtccatttgttgtaagtag caactaa Particularly preferred is a *Nicotiana tabacum* sequence SEQ ID No. 6, whereby amino acid residues 1 to 150, preferably 1 to 140, more preferably 1 to 130, more preferably 1 to 120, more preferably 1 to 110, in particular 1 to 107, of SEQ ID No. 6 represent the signal peptide and propeptide region:

(SEQ ID No. 6)
MKGLFLFICFSLFIVSFIIEADSASQSQNNGIYIVYMGAAASSNGGTRHD

QAQLISSLIRRNKNAVVHSYKNGFSGFAARLSEAEAKSMAQRPGVVSVFP

DPVLQLHTTHSWDFLKYQTDEKINSSPSSGSDSSLIGADTIIGILDTGIW

PESESFNDKDMGPIPARWNGTCMDGQDFGSSNCNKKIVGARFYEESDDSG

IKITGSARDENGHGTHVASTAAGSPVAGASYYGLAAGTATGGSPGSRIAM

YRVCTTFGCRGSAIMKAFDDAIADGVDVLSLSLGSSPGLEPDFPTNPIAI

GAFHAVEKGIVVVCSAGNSGPGPKTVVNTAPWILTVAATTIDRDFETDVL

LGGNKLIKGGGINFGNMTKSTVYPLIHGNSTKSNDNVSEADARSCVPGSL

DENKVKGKIVLCENLDDGEYFPSDKLDEVKSRGGVGFILIDDDERTVAPK

FKAFPAGVVSKKDGTEILAYINSTRNPVASILPTISITKYKPAPVVAYFS

SRGPAYNTPNLLKPDITAPGVAILAAWPGNDTSEALPGQKPPIFNLLSGT

SMSCPHVSGIAATVKAVNPTWSPSAVKSAIMTTAIQTNNLKAPITTVSGS

KATPYDIGAGEASTSGPLKPGLVYETDVADYLQFLCSVGFNISQIKLISS

TVPKDFSCPKNSSSELVSNMNYPSIATSSLKENEPKKVTRTVTNTGEEAS

VYTAIIEAPKGLEVQVIPTKLEFTNKRKKVSYDVSFKASSTSKEDLFGSI

TWTNGKYKVRSPFVVSSN

A nucleic acid sequence encoding the *Nicotiana tabacum* subtilisin-like serine protease may comprise SEQ ID No. 7, whereby nucleotide residues 1 to 450, preferably 1 to 420, more preferably 1 to 390, more preferably 1 to 360, more preferably 1 to 330, in particular 1 to 321, of SEQ ID No. 7 encode the signal peptide and the propeptide region:

(SEQ ID No. 7)
atgaaaggcctttttttgttcatatgcttctctcttttcattgtctcttt cataatagaagccgactcagcttctcaatcacaaaacaatggcatttata ttgtttatatgggtgctgcggcttcatctaacggtggtaccagacatgat caagcgcagcttatcagctccttgatcagaaggaacaagaatgcagtggt acacagctacaagaatggtttctcaggatttgcggcacgtttatcagaag ctgaagctaaatcgatggctcaaagacctggagttgtctctgtatttcct gatccagtactgcaactccacactacacattcatgggatttcttgaagta -continued

```
tcaaactgatgaaaaaatcaattcaagtccaagctctggttctgattcat
cattaattggagctgataccataattggaatcttggatacgggtatatgg
ccagaatcagagagtttcaatgacaaggatatgggtccaattccagcccg
gtggaatggaacttgcatggatggtcaagattttggctcttccaattgca
acaagaagatagttggtgcaagattttatgaggagtctgatgacagtgga
ataaaaatcactggatcagccagggacgagaacggacatggtactcacgt
tgcatccactgcagctgggagccctgttgcaggtgcatcctactatggcc
tagctgcagggactgcaacaggtggatctccgggttccaggatcgccatg
tatcgtgtctgtactacttttggatgccgtggatcagctatcatgaaagc
attcgatgatgcaattgcagatggggttgatgttttatctctatcactcg
gttcatcacctggacttgaacctgattttccaaccaatcctattgccata
ggagcatttcatgccgtagaaaagggcattgttgttgtttgctctgctgg
aaatagtggccctggcccaaaaaactgttgtcaatacagctccttggattc
ttactgttgcagccaccaccattgatcgtgacttcgagacagatgttctc
ttgggtggaaacaagttgattaagggtggaggtataaactttggtaacat
gacaaaatcaacagtctaccccttgattcatggcaattcaaccaaatcaa
acgataatgtttctgaggcagatgcaaggagttgtgttcctggttcatta
gatgaaaacaaagtcaaggggaagattgttctttgtgaaaatcttgatga
tggcgaatattttcccagtgacaagctagacgaagtgaagagtcgaggtg
gagttggatttatactaatagatgatgatgaaagaactgtggcacctaaa
ttcaaagccttcccagcgggtgtagtctctaaaaaggatggtactgagat
cctcgcctacattaactcgacaaggaatccagttgcatcaattttgccaa
ctatttccataacaaagtacaaaccagctccagttgttgcttacttctca
tcaagaggtcctgcatacaatacacctaacctcctcaaaccagatattac
agcaccaggggttgccattcttgctgcttggcctggaaatgacacgagtg
aggctctccccggccaaaaaccaccaattttcaacctactctcaggcact
tccatgtcctgccctcacgtttctggcattgctgcaacggtcaaagcagt
gaacccaacctggagtccttcagctgtcaaatcagctattatgaccacag
ctattcagacaaacaatttgaaggctccaatcactacagtctcaggatcc
aaagcaacaccatatgacataggagcaggagaagcaagcacttcaggtcc
attaaaaccaggtctagtctacgagacagatgtcgccgactacttgcagt
tcctctgttctgttggctttaacatatcacagataaagctgatctcaagt
acagttcctaaggacttttcatgcccaaaaaactcaagctctgaattggt
ttctaacatgaattatccttcaatagctacttctagtctcaaagaaaacg
agcccaagaaagttactagaactgttacaaatactggtgaagaagcatca
gtatatactgcaattattgaggcaccaaaaggattggaagtccaagtgat
tccaactaaattggaatttacaaataaaaggaagaaagtaagctatgatg
tatctttcaaagcctcatctacctcaaaggaagatctgtttggatcaatt
acttggacaaatggtaagtacaaagtccggagtccatttgtcgtaagtag
caactaa
```

Particularly preferred is a *Solanum lycopersicum* sequence SEQ ID No. 8, whereby amino acid residues 1 to 150, preferably 1 to 140, more preferably 1 to 130, more preferably 1 to 120, more preferably 1 to 110, in particular 1 to 107, of SEQ ID No. 8 represent the signal peptide and propeptide region:

```
                                             (SEQ ID No. 8)
MRDIVLFFCFLLFLLSLLRETNAVSQEKNNGVYIVYMGAADSSNDGTKNQ
QAELMSSLIKRKKDAVVHSYNNGFSGFAARLSEAEAKSIAQKPGVISVFP
DPILQLHTTRSWDFLQYQTEVESSSGPISGSDNASPKGVDTIIGILDTGI
WPESESFSDNDMSEVPSKWKGTCMGSHDSISFKCNKKLVGARFYDDSDED
GVRPFGSARDDNGHGTHVASTAAGSLISGASYYGLASGTAKGGSPGSRIA
MYRVCTADGCHGSAIMKAFDDAIADGVDVLSLSLGSSSGLEVEFSRDPIA
IGAFHAVEKGILVSCSAGNDGPGPATVVNVAPWILTVAATTIDRDFETDI
VLGGNKLIKGGGISLGNLTRSPVYPLISGDLAKSSNNVVMEKGARYCYPN
SLDETKVKGKIVLCDNRDGYFSLTEKLTEVKKKGGIGFILIDDNARTVAP
KFNSFPAAVVTEKDSNEILSYINSTKKPVASVLPTVTIANYKPAPLVAYF
SSRGPTYNTHNLLKPDITAPGVAILAAWPGNDTTEAVAGQALPLYNIISG
TSMSCPHVSGIAALVKAQNPSWSPSAIRSAIMTSALQTNNLKAPITTVSG
SVATPYDIGAGEASPSLALNPGLVYETNTADYLQYLCSVGYDKSKIKLIS
NTVPDDFSCPTNSSSESVSQMNYPSIAVSNIKENEIKKVTRTVTNVGQDD
ATYTASIKAPVGLEVQVTPNKLVFTNNSKKLSYEMSFKASSKPKEDLFGS
ITWTNGKYKVRSPFVISTNSQGEHSKTADRRSN
```

A nucleic acid sequence encoding the *Solanum lycopersicum* subtilisin-like serine protease may comprise SEQ ID No. 9, whereby nucleotide residues 1 to 450, preferably 1 to 420, more preferably 1 to 390, more preferably 1 to 360, more preferably 1 to 330, in particular 1 to 321, of SEQ ID No. 9 encode the signal peptide and the propeptide region:

```
                                             (SEQ ID No. 9)
atgagagacattgttctgtttttttgcttccttttatttttactctcttt
gcttagagaaactaatgcagtttctcaagaaaaaaacaatggtgtttata
ttgtttacatgggtgctgctgattcgtcgaacgatggcacgaaaaatcag
caagcagaactaatgagctcattgataaaaaggaaaaaggatgcagttgt
acacagttacaacaatggtttctcaggattcgcagcgcgtttatcagaag
ctgaggctaaatctattgctcaaaaacctggagttatatcagtattccct
gatccaatattgcaactacacacaacgcgttcgtgggactttttgcaata
tcaaactgaagtagaaagcagttctggtccaatatctggttctgataacg
cgtcaccaaaaggcgttgatactataattggaatcctggatacaggaata
tggcctgaatcagagagttttagtgataatgatatgagtgaagttccatc
taagtggaaaggaacttgtatgggaagtcatgattccatctctttcaaat
gcaacaagaagttagttggtgcaaggttctatgatgactctgatgaggat
ggtgtaagaccttttggttcagctagggatgataatggacatggaactca
tgttgcatctacagcagctgggagtttgatttcaggagcatcttattatg
gtttggcttctgggacagcaaagggtggatccccgggttcaagaatagcc
```

-continued atgtatcgtgtctgcacggctgatggatgtcacggatcagctataatgaa
agcatttgatgatgcaattgcagatggggttgatgttttatcgctatcac
ttggttcatcatctggtcttgaagtcgagttttctagagatcctatagct
attggagcattccatgctgttgaaaagggaattcttgtttcctgttctgc
tggaaatgatggccctggtccggcaactgttgtcaatgttgcaccttgga
ttctcactgttgcagctactacaattgaccgtgacttcgagacagatatt
gtcttaggtggaaacaagttgataaagggaggaggtataagtttaggtaa
cttgacaagatctccagtatacccgttgattagtggcgatttagccaaat
ccagcaataatgttgttatggagaaaggtgcaaggtattgttatccgaat
tcattagatgaaaccaaagttaaggggaaaattgttctctgtgataatcg
cgacggatacttttcacttactgagaaactaacagaagtgaagaagaaag
gtggcattggatttatactaatagatgataatgcaagaactgtggcccca
aaattcaattcctttccagcagctgttgtaactgaaaaggatagcaatga
gatcctttcttacatcaactcaacaaagaaaccagttgcatcagttctgc
caactgttaccatagctaactacaaaccagctcctcttgtggcttacttc
tcatcaaggggtcctacatacaacacacataatctcctcaaaccagatat
tacagcaccaggtgttgcaattctcgcggcttggcctggaaacgacacaa
cagaggctgtcgctggccaggcgttaccactttacaacataatatcaggg
acttccatgtcctgccctcatgtttctggtattgccgcgttagtcaaggc
gcaaaatccttcttggagtccttcagcaatcagatcagctattatgacct
cagctttacagactaacaatttgaaggctccaatcacaacagtctctgga
tccgttgcaacaccatacgacataggagctggagaagcaagcccttcatt
ggcacttaatccaggattggtctacgagactaacaccgcagactacttgc
agtacctatgctcagttggctacgataaatcaaagataaaactcatttca
aatacagttcctgatgatttttcatgtcccaccaactcaagttctgaatc
cgtctcacaaatgaactacccttccattgctgtttcaaatatcaaagaaa
atgaaatcaagaaagtaacaagaactgtaactaacgtaggacaagacgac
gcaacatacacagcaagtataaaggcaccagttggtttggaagtccaagt
gaccccgaataaattggtatttacaaataatagcaagaagttgagctatg
aaatgtctttcaaagcttcatctaaaccaaaggaagacttgtttggatca
attacatggacaaatggtaaatacaaagtccgaagtccattcgttatatc
tactaattcacaaggtgaacactccaaaacagcagatcgcagatcaaact
ag Particularly preferred is a *Solanum tuberosum* sequence SEQ ID No. 10, whereby amino acid residues 1 to 150, preferably 1 to 140, more preferably 1 to 130, more preferably 1 to 120, more preferably 1 to 110, in particular 1 to 107, of SEQ ID No. 10 represent the signal peptide and propeptide region:

(SEQ ID No. 10)

MKVIVLFFCFFLLLLSFLRETNAVSQEKNNGVYIVYMGAADSSNDGTKNQ
RAELMSSLIRRKKDAVVHSYSNGFSGFAARLSEAEAKSIAQKPGVISVFP
DPILQLHTTRSWDFLQYQTEVESSSGPISGSDNASPKGVDTIIGILDTGI
WPESESFSDNDMSEVPSKWKGTCMASHDSISFKCNKKLVGARFYDDSDED
GVRPSGSARDENGHGTHVASTAAGSPISGASYYGLASGTAKGGSPGSRIA
MYRVCMTDGCHGSAIMKAFDDAIADGVDVLSLSLGSSSGLEVEFSSDPIA
IGAFHAVEKGILVSCSAGNDGPGPATVVNVAPWILTVAATTIDRDFETDI
VLGGNKLIKGGGISLGNLTRSPVYPLISGDLAKSGNTVVSEKNARFCNPN
SLDGTKVKGKVVLCDNRDGYYSLTEKLTEVKSKGGIGFIVVDDNARTVAP
KFKSFPAAVVTEKDSNEILSYINSTKKPVASVLPTVTIANYKPAPLVAYF
SSRGPTYNTHNLLKPDITAPGVAILAAWPGNDTNEAVAGQAPPLYNIISG
TSMSCPHVSGIAALVKAQNPSWSPSAIKSAIMTSALQTNNLKAPITTVSG
SVATPYDIGAGEASPSLALNPGLVYETNTADYLQYLCSVGYDKSKIKLIS
NTVPNDFSCPTNSSSESVSQMNYPSIAVSNIKENEIKKVTRTVTNVGQED
ATYTASIKAPVGLEVQVTPNKLVFTNNSKKLSYEVSFKASSKPKEDLFGS
ITWINGKYKVRSPFVVSTNSQGV

A nucleic acid sequence encoding the *Solanum tuberosum* subtilisin-like serine protease may comprise SEQ ID No. 11, whereby nucleotide residues 1 to 450, preferably 1 to 420, more preferably 1 to 390, more preferably 1 to 360, more preferably 1 to 330, in particular 1 to 321, of SEQ ID No. 11 encode the signal peptide and the propeptide region:

(SEQ ID No. 11)

atgaaagtcattgttctgtttttttgcttctttttattattactctcttt
tcttagagaaactaatgcagtttctcaagaaaaaaacaatggtgtataca
ttgtttacatgggcgctgctgattcgtcgaacgatggcacgaaaaatcag
cgagcagaacttatgagctctttgataagaagaaaaaaggatgcagttgt
acacagttacagcaatggtttctcaggattcgcagcgcgtttatcagaag
ctgaggctaaatccattgctcaaaaacctggagttatatcagtattccct
gatccaatattgcaactccacacaacgcgttcgtgggacttttttgcaata
tcaaactgaagtagaaagcagttctggtccaatatcaggttctgataacg
cgtcaccaaaaggcgttgatactataattggaatcttggatacaggaata
tggcctgaatcagagagttttagtgataatgatatgagtgaagttccatc
taagtggaaaggaacttgtatggcaagtcatgattccatctctttcaaat
gcaacaagaagttagttggtgcaaggttctatgatgactctgatgaggat
ggtgtaagaccttctggttcagctagggatgagaatggacatggaactca
tgttgcatctacagcagctgggagtccgatttcaggagcatcttattatg
gtttggcttctgggaccgcgaagggtggatccccgggttcaagaatagcc
atgtatcgtgtctgcatgactgatggatgtcacggatcagctataatgaa
agcatttgatgatgcaattgcagatggggttgatgttttatcgctatcac
ttggttcatcatctggtcttgaagttgagttttcgagtgatcctatagct
attggagcattccatgctgttgaaaagggaattcttgtttcctgttctgc
tggaaatgatggccctggtccggcaactgttgtcaacgtcgcgccttgga
ttctcacagttgcagctactacaattgaccgtgacttcgagacagatatt -continued gtcttaggtggaaacaagttgattaagggtggaggtataagtcttggtaa tttgacaagatctccagtatacccgttgattagtggcgatttagccaagt ccggcaatactgttgtttcggagaaaaatgcaaggttttgtaatccgaat tcattagatggaaccaaagttaaggggaaagttgttctttgtgataatcg cgacggatactattcacttactgagaaactaacagaagtgaagagcaaag gtggcattggatttatagtagtagatgataatgcaagaactgtggcacct aaattcaaatcctttccagcagctgttgtaactgaaaaggatagcaatga gatcctttcttacatcaactcaacaaagaaaccagttgcatcagttctgc caactgttaccatagctaactacaaaccagctcctcttgtggcttacttc tcatcaaggggtcctacatacaacacacataatctcctcaaaccagatat tacagcaccaggtgttgcaattctcgcggcttggcctggaaacgacacaa acgaggctgtcgctggccaggcgccaccactttacaacataatatcaggg acttccatgtcctgccctcatgtttctggtattgccgcattagtcaaggc gcaaaatccttcttggagtccttcagcaatcaaatcagctatcatgacct cagctttacagactaacaatttgaaggctccaatcacaacagtctccggc tccgttgcaacaccatacgacataggagctggagaagcaagcccttcatt ggcacttaatccaggattggtctacgagactaacactgcagactacttgc agtacctatgctcagttggctacgataaatcaaagataaaactcatctca aatactgttcctaatgatttttcatgtcccaccaactcaagttctgaatc cgtctcacaaatgaactacccttccattgctgtttcaaatatcaaagaaa atgaaatcaagaaagtaacaagaactgtaactaacgtaggacaagaagac gcaacatacacagcaagtataaaagcaccagttggtttggaagtccaagt gaccccgaataaattggtatttacaaataatagcaagaagttgagctatg aagtgtctttcaaagcttcatctaaaccaaaggaagacttgtttggatca attacatggacaaatggtaaatacaaagtccgaagtccattcgttgtatc tactaattcacaaggtgtctga Another plant subtilisin-like serine protease of *Arabidopsis thaliana* may comprise amino acid sequence SEQ ID No. 12, whereby amino acid residues 1 to 150, preferably 1 to 140, more preferably 1 to 130, more preferably 1 to 120, more preferably 1 to 110, in particular 1 to 108, of SEQ ID No. 12 represent the signal peptide and propeptide region:

(SEQ ID No. 12)

MKGITFFTPFLSFLYLLCILFMTETEAGSRNGDGVYIVYMGSASSAANAN

RAQILINTMFKRRANDLLHTYKHGFSGFAARLTAEEAKVIAKKPGVVSVF

PDPHFQLHTTHSWDFLKYQTSVKVDSGPPSSASDGSYDSIVGILDTGIWP

ESESFNDKDMGPIPSRWKGTCMEAKDFKSSNCNRKIIGARYYKNPDDDSE

YYTTRDVIGHGSHVSSTIAGSAVENASYYGVASGTAKGGSQNARIAMYKV

CNPGGCTGSSILAAFDDAIADGVDVLSLSLGAPAYARIDLNTDPIAIGAF

HAVEQGILVICSAGNDGPDGGTVTNTAPWIMTVAANTIDRDFESDVVLGG

NKVIKGEGIHFSNVSKSPVYPLIHGKSAKSADASEGSARACDSDSLDQEK

VKGKIVLCENVGGSYYASSARDEVKSKGGTGCVFVDDRTRAVASAYGSFP

-continued

TTVIDSKEAAEIFSYLNSTKDPVATILPTATVEKFTPAPAVAYFSSRGPS

SLTRSILKPDITAPGVSILAAWTGNDSSISLEGKPASQYNVISGTSMAAP

HVSAVASLIKSQHPTWGPSAIRSAIMTTATQTNNDKGLITTETGATATPY

DSGAGELSSTASMQPGLVYETTETDYLNFLCYYGYNVTTIKAMSKAFPEN

FTCPADSNLDLISTINYPSIGISGFKGNGSKTVTRTVTNVGEDGEAVYTV

SVETPPGFNIQVTPEKLQFTKDGEKLTYQVIVSATASLKQDVFGALTWSN

AKYKVRSPIVISSESSRTN

A nucleic acid sequence encoding the *Arabidopsis thaliana* subtilisin-like serine protease may comprise SEQ ID No. 13, whereby nucleotide residues 1 to 450, preferably 1 to 420, more preferably 1 to 390, more preferably 1 to 360, more preferably 1 to 330, in particular 1 to 324, of SEQ ID No. 13 encode the signal peptide and the propeptide region:

(SEQ ID No. 13)

atgaaaggcattacattcttcacaccctttttatcatttctatatctctt atgcatcttgtttatgacagaaactgaagctgggtcgagaaatggtgatg gggtctacattgtctacatgggatcagcttcctctgctgcaaacgctaat agagctcaaatactcataaacaccatgtttaaaaggagagcaaacgatct tctccacacatataagcatggcttctcaggttttgcagctcgtttgacag cagaagaggccaaggtcatagccaagaaaccgggagtggtttcagttttt cctgacccacacttccagcttcatacaactcattcatgggactttctcaa gtaccaaacatcagtaaaggtcgattccggtccaccttcatcagcctcag atggatcatatgatagcattgtcggaattcttgacacagggatatggcca gagtcagagagtttcaatgacaaagacatgggtccaattccgtctcggtg gaaaggtacatgcatggaagcaaaggacttcaagtcttccaactgtaaca gaaagatcattggagcaagatactacaaaaatcctgatgatgattcagaa tactataccacaagggatgtcatcggtcacggttctcatgtgtcctccac catagctggatctgccgtggagaatgcttcctactatggtgtagcttccg ggactgcaaagggaggttcacaaaacgctagaatcgctatgtacaaagta tgcaatccaggggggatgcactggctcctctatcttagctgctttcgatga tgcaatcgcagatggagttgatgttctatctctgtctcttggagctccag catacgctcgcatcgacttgaacactgatcctattgccattggagcgttt cacgcggtggagcaaggaatcttggtgatctgctctgcgggtaatgatgg acctgatggcggtacagttactaatactgcaccttggataatgaccgttg ctgccaacactattgatagagactttgagtctgatgttgtactaggcggc aataaagtcatcaagggtgaaggtatacacttttcaaacgttagtaaatc tcctgtgtatcctctgattcatggcaagtctgctaagagcgctgatgcat cagaaggatcagccagggcctgtgactctgattctctagatcaagagaag gtaaaagggaagattgtgttatgcgagaacgttggtggatcatattatgc atcatccgctagggacgaggtgaagagcaaaggaggtactggttgcgtct ttgtagatgacagaactagagcagttgctagtgcttatggtagctttcct actaccgtaattgactcaaaggaagcagctgagatcttctcctacctcaa -continued ctcaaccaaagatcctgttgcaacaattcttcccactgcaacagttgaaa agttcacacctgcccctgctgttgcatatttttcttccagaggaccttca agcctcacaagaagcattctcaaacctgacattaccgcaccaggagtctc gatactcgctgcatggactggaaacgactcaagcatttcactggaaggca agccggcttctcagtataacgtcatatcaggaacttccatggcagctcct catgtttcagctgttgcatctctgatcaaatcacagcatcccacatgggg tccatccgcgatcagatcagcaattatgacaacagcgactcaaacaaaca acgacaaaggtcttataacaacagaaactggtgcaacagccacaccttat gactctggagcaggagaactaagctcaacagcatcaatgcaaccaggact agtttacgagactactgaaactgactacctgaactttctctgttactatg gatataacgtaaccacaataaaggctatgtcaaaagcttttccagagaat tttacttgccctgcagattccaacttagacttgatctccaccatcaatta cccgtcaattggaatctctggattcaaaggaaatggtagcaagacagtta caagaacagtgaccaatgttggtgaggacggtgaggcggtttacacagtc agcgtggaaacaccaccagggtttaacattcaagtgacgccagaaaaact ccaatttacaaaagatggtgagaagttgacataccaggtgatagtgtctg ctactgcttcacttaagcaagatgtatttggggctcttacttggtctaat gccaagtacaaggtcagaagcccaattgtaattagtagcgagagtagccg cacaaactga Particularly preferred is a *Nicotiana benthamiana* subtilisin-like serine protease (SBT2) comprising amino acid sequence SEQ ID No. 14, whereby amino acid residues 1 to 150, preferably 1 to 140, more preferably 1 to 130, more preferably 1 to 120, more preferably 1 to 115, in particular 1 to 110, of SEQ ID No. 14 represent the signal peptide and propeptide region. The amino acids of the catalytic triad (Asp142, His213, Ser529) are underlined:

(SEQ ID No. 14)

MANHITLCIWLLFFFISIFSLAKSETYIIHMDLSAMPKAFSSHHNWYLTT

LSSVSDSSTNHKDFLSSKLVYAYTNAIHGFSASLSPSELEAIKYSPGYVS

SIKDISVKIDTTHTSQFLGLNSKSGVWPTSDYGKDIIIGLVDTGIWPESK

SYSDDGISEVPSRWKGECESGTEFNSSLCNKKLIGARYFNKGLLANNPNL

NISMNSSRDTDGHGTHTSSTAAGSYVEGASYFGYATGTAIGIAPKAHVAM

YKALWEEGVYLSDVLAAIDQATTDGVDVLSLSLGIDAIPLHEDPVAIAAF

AALEKGIFVSTSAGNEGPYYETLHNGTPWVLTVAAGTVDREFIGTLTLGN

GVSVPGLSLYPGNSSSSESSLVYVECQDDKELQKNAHKFVVCLDKNDSVG

EHVYNVRNSKVAGAVFITNTTDLEFYLQSEFPAVFLNLQEGDKVLEYIKS

NSAPKGKLEFQVTHIGAKPAPKVATYSSRGPSPSCPSILKPDLMAPGALI

LASWPQQSPVTDVTSGKLFSNFNIISGTSMSCPHASGVAALLKAAHPEWS

PAAIRSAMMTTSTALDNTQSPIRDIGNKNAAATPLAMGAGHIDPNKALDP

GLIYDATPQDYVNLLCALNFTSKQIKTITRSSSYTCSNPSLDLNYPSFIG

FFNGNSSESDPKRIQEFKRTVTNLQDGTSIYTANFTPMGKFKVSVVPEKL

-continued

VFKEKYEKLSYKLRIEGPIVMDDNVVYGSLSWVETGGNYVVRSPIVATSI

KVDPLTGHN

A nucleic acid sequence encoding the *Nicotiana benthamiana* subtilisin-like serine protease may comprise SEQ ID No. 15, whereby nucleotide residues 1 to 450, preferably 1 to 420, more preferably 1 to 390, more preferably 1 to 360, more preferably 1 to 345, in particular 1 to 330, of SEQ ID No. 15 encode the signal peptide and the propeptide region:

(SEQ ID No. 15)

atggcaaatcatattaccttgtgtatttggttgcttttcttctttatttc tatattttcactagcaaagtcagaaacatatatcattcatatggatttgt cagccatgccaaaagctttttctagccatcataattggtacttgacaaca ctttcttctgtatcagacagcagtacaaatcacaaagacttcttgtcctc aaaactagtctatgcttatactaatgctatacatggttttagtgcaagtc tctctccttctgaacttgaagccataaaatattctccaggttatgtttct tcaattaaggatatttcagttaaaattgacacaactcacacatcccagtt tcttggcctaaactctaagtctggtgtatggccaacgtccgactatggga aagatatcataattggcttagttgatactggaatatggcctgagagtaaa agctatagtgatgatgggattagtgaagtaccatcaagatggaaaggaga atgtgaaagtggtactgagttcaattcctctttgtgtaacaagaagctca ttggcgctcgttacttcaataaaggcctacttgccaacaatccaaatctt aatatttcaatgaattcttctagagataccgatggacatggaactcacac ttcttctacagctgcgggaagttatgttgagggtgcatcttatttggct atgccaccggtactgctattggcatagcgccaaaggctcatgtggctatg tacaaggctctatgggaagaaggtgtatacttgtctgatgttcttgctgc aattgatcaagcaattacagatggtgtggatgtcttatccttgtcgttag gcatagacgcgattccactacacgaagatcctgtggcaattgccgcattt gctgcattggagaaaggtatatttgtttccacctctgcaggaaatgaagg gccttattatgagactttgcacaatggaacacccttgggtgttaactgttg cagctggcacagttgaccgcgaatttattggaacattaactcttggaaat ggagtttcagtccctggtttatcgctataccctgggaattctagttcaag cgaaagctcccttgtctatgtcgaatgccaagatgacaaggaactgcaga aaaatgcacacaaatttgttgtctgtctcgacaagaatgattcggttggt gagcatgtgtacaatgtaagaaattcaaaagttgctggggctgtctttat aactaatacaactgacttggaattctacctccaaagcgaattcccggctg tgttcttgaacttacaagagggtgataaagttctagagtacattaagagc aactctgcacctaaaggaaaacttgaattccaagttacacatattggtgc taaaccagcgccaaaagttgctacctatagctcaagaggaccgtcaccga gttgtccaagtatcctcaaacctgatctcatggctcctggtgccttaata cttgcttcatggccacaacaatcaccagttactgatgttacctcaggaaa actttttagtaacttcaatattatatctggtacatcaatgtcatgtccac atgcttctggtgtagcagcacttctaaaagctgcacaccctgaatggagc -continued cctgcagccatccgatctgccatgatgaccacttccactgcgttggacaa cacacagagccccatccgagacataggtaacaagaatgcggctgctactc ctctagccatgggagctggccatatcgatccaaacaaggcgttagatcct ggacttatctatgatgcaacaccacaagattatgtcaatctcctctgtgc tctgaacttcacatccaaacaaataaaaaccatcacaagatcctcatctt atacttgctccaacccatcattggacttaaactatccatccttcattggc tttttcaatggtaacagcagcgagtcggatcctaaaaggattcaagaatt taaaagaacagtgacaaacttacaagatggtacatcaatatatacagcaa acttcactccaatgggtaaatttaaagttagtgttgtacctgaaaagttg gttttcaaagagaagtatgaaaagctgagctacaagcttagaatagaagg tccaatagttatggatgataatgtggtttatggttctttgagctgggtag aaactggaggtaactatgtggttagaagtccaattgttgccacaagcata aaagtggatcctttgacaggacacaactga Particularly preferred is a *Nicotiana tabacum* sequence SEQ ID No. 16, whereby amino acid residues 1 to 150, preferably 1 to 140, more preferably 1 to 130, more preferably 1 to 120, more preferably 1 to 115, in particular 1 to 110, of SEQ ID No. 16 represent the signal peptide and propeptide region:

(SEQ ID No. 16)

MANHITLCIWLLFFFISIISLAKSETYIIHMDFSAMPKAFSSHHNWYLTT

LSSVSDSSTNYKDFLSSKLVYSYTNAIHGFSASLSPSELEAIKNSPGYVS

SIKDISVKIDTTHTSQFLGLNSESGVWPTSEYGKDIIIGLVDTGIWSESK

SYSDDGISEVPSRWKGECESGTEFNSSLCNKKLIGARYFNKGLLANNPNL

NISMNSARDTDGHGTHTSSTAAGSYVEGASYFGYATGTAIGIAPKAHVAM

YKALWEEGVYLSDVLAAIDQAITDGVDVLSLSLGIDAIPLHEDPVAIAAF

AALEKGIFVSTSAGNEGPYYETLHNGTPWVLTVAAGTVDREFIGTLTLGN

GVSVTGLSLYPGNSSSSESSIVYVECQDDKELQKNAHKFVVCLDKNDSVG

EHVYNVRNSKVAGAVFITNTTDLEFYLQSEFPAVFLNLQEGDKVLEYIKS

NSAPKGKLEFQVTHIGAKRAPEVATYSSRGPSPSCPSILKPDLMAPGALI

LASWPQQSPVTDVTSGKLFSNFNIISGTSMSCPHASGVAALLKGAHPEWS

PAAIRSAMMTTSSALDNTQSPIRDIGNVELRNAAATPLAMGAGHIDPNKA

LDPGLIYDATPQDYVNLLCALNFTSKQIKIITRSSSYTCSNPSLDLNYPS

FIGFFNGNSRESDPKRIQEFKRTVTNLQDGTSVYTANLIPMGKFKVSVVP

EKLVFKEKYEKLSYKLRIEGPIVMDDNVVYGSLSWVETGGKYVVRSPIVA

TSIKVDPLTGHN

A nucleic acid sequence encoding the *Nicotiana tabacum* subtilisin-like serine protease may comprise SEQ ID No. 17, whereby nucleotide residues 1 to 450, preferably 1 to 420, more preferably 1 to 390, more preferably 1 to 360, more preferably 1 to 345, in particular 1 to 330, of SEQ ID No. 17 encode the signal peptide and the propeptide region:

(SEQ ID No. 17)

atggcaaatcatattaccttgtgtatttggttgcttttcttctttatttc tataatttcactagcaaagtcagaaacatatatcattcatatggattttt cagccatgccaaaagctttttctagccatcataattggtacttgacaaca ctttcttctgtatcagacagcagtacaaattacaaagacttcttgtcctc aaaactagtctattcttatactaatgccatacatggttttagtgcaagtc tttctccttctgaacttgaagccataaaaaattctccaggctatgtttct tcaattaaggatatttcagttaaaattgacacaactcacacatcccaatt tcttggcctaaactctgagtctggtgtatggccaacgtccgagtatggta aagatatcataattggcttagttgatactggaatatggtcggagagtaaa agctatagtgatgatgggattagtgaagtaccatcaagatggaaaggaga atgtgaaagtggtactgagttcaattcctctttgtgtaacaagaaactca ttggcgctcgttacttcaataaaggcctacttgccaacaatccaaatctt aacatttcaatgaattctgctagagataccgatggacatggaactcacac ttcttctacagctgcgggaagttatgtcgagggtgcatcttattttggct atgccactggcactgctataggcatagcaccaaaggctcatgtggctatg tacaaggctctatgggaagaaggtgtatacttgtctgatgttcttgctgc aattgatcaagcaattacagatggtgtggatgtcttatccttgtctttag gcatagacgcgattccactacacgaagatcctgtggcaattgccgcattt gctgcattggagaaaggtatatttgtttccacctctgcaggaaatgaagg gccttattatgagactttgcacaatggaacaccttgggtgctaactgttg cagctggcacagttgaccgcgaatttattggaacattaactcttggaaat ggagtttcagtcactggcttatcgctataccctgggaattctagttcaag cgaaagctccattgtctatgtcgaatgccaagatgacaaggaactacaga aaaatgcacataaatttgttgtctgtctcgacaagaatgattcggtcggt gagcatgtgtacaatgtaagaaattcaaaagttgctggggctgtctttat aactaatacaactgacttggaattctacctccaaagcgaattcccggctg tgttcttgaacttacaagagggtgataaagttctagagtacattaagagc aactctgcacctaaaggaaaacttgaattccaagtgacacatattggtgc taaacgagcaccagaagttgctacctatagctcaagaggaccgtcaccga gttgtccaagtatcctcaagcctgatctcatggctcctggtgccttaata cttgcttcatggccacagcaatcaccagttactgatgttacctcaggaaa gctttttagtaacttcaatattatatctggtacatcaatgtcatgtccac atgcttctggtgtagcagcacttctaaaaggcgcacaccctgaatggagc cccgcagccatccgatctgccatgatgaccacttccagtgcgttggacaa cacacagagccccatccgagacataggtaatgttgaactcaggaatgctg ctgctactcctctagccatgggagctggccatatcgatccaaacaaggca ttagatcctggacttatctatgatgcgacaccacaagattatgtcaatct tctctgtgctctgaacttcacatccaaacaaataaaaatcatcacaagat cctcatcttatacttgctccaacccatcattggacttaaactatccatcc ttcattggctttttcaatgggaacagcagagagtcggatcctaaaaggat -continued

```
tcaagaattcaaaagaacagtgacaaacttacaagatggtacatcagtat

atacagcaaatctcactccaatgggtaaatttaaagttagtgttgtacct

gaaaagttggttttcaaagagaagtatgaaaagctgagctacaagcttag

aatagaaggtccaatagttatggatgataatgtggtttatggttctttga

gctgggtagaaactggaggtaaatatgtggttagaagtccaattgttgcc

acaagcataaaagtggatcctttgacaggacacaactga
```

Particularly preferred is a *Nicotiana tabacum* sequence SEQ ID No. 18, whereby amino acid residues 1 to 150, preferably 1 to 140, more preferably 1 to 130, more preferably 1 to 120, more preferably 1 to 115, in particular 1 to 110, of SEQ ID No. 18 represent the signal peptide and propeptide region:

```
                                         (SEQ ID No. 18)
MASHITLCIWLLFFFISIISLAKPETYIIHMDLSAMPKAFASHHNWYLTT

LASLSDSSTNHKEFLSSKLVYAYTNAINGFSASLSPSEFEAIKNSPGYVS

SIKDMSVKIDTTHTSQFLGLNSESGVWPTSDYGKDIIIGLVDTGIWPESK

SYSDYGISEVPSRWKGECESGIEFNSSLCNKKIIGARYFNKGLLANNPNL

NISMNSARDTDGHGTHTSSTAAGSYVEGASYFGYATGTAIGIAPKAHVAM

YKALWEEGVYLSDVLAAIDQAITDGVDVLSLSLGIDAIPLHEDPVAIAAF

AALEKGIFVSTSAGNEGPYYETLHNGTPWVLTVAAGTVDREFIGALTLGN

GVSVTGLSLYPGNSSSSESSIVYVECQDDKELQKSAHNIVVCLDKNDSVS

EHVYNVRNSKVAGAVFITNITDLEFYLQSEFPAVFLNLQEGDKVLEYIKS

NSAPKGKLEFRVTHIGAKPAPKVATYSSRGPSPSCPSILKPDLMAPGALI

LASWPQQSPVTDVTSGKLFSNFNIISGTSMSCPHASGVAALLKAAHPEWS

PAAIRSAMMTTSNAMDNTQSPIRDIGSKNAAATPLAMGAGHIDPNKALDP

GLIYDATPQDYVNLLCALNFTSKQIKTITRSSSYTCSNPSLDLNYPSFIG

FFNGNSSESDPRRIQEFQRTVTNIGDGMSVYTAKLTTMGKFKVNLVPEKL

VFKEKYEKLSYKLRIEGPLVMDDIVVYGSLSWVETEGKYVVRSPIVATSI

KVDPLTGHN
```

A nucleic acid sequence encoding the *Nicotiana tabacum* subtilisin-like serine protease may comprise SEQ ID No. 19, whereby nucleotide residues 1 to 450, preferably 1 to 420, more preferably 1 to 390, more preferably 1 to 360, more preferably 1 to 345, in particular 1 to 330, of SEQ ID No. 19 encode the signal peptide and the propeptide region:

```
                                         (SEQ ID No. 19)
atggcaagtcatattaccttgtgtatttggttgcttttcttctttatttc

tataatttcactagcaaagccagaaacatatatcattcatatggatttgt

cagccatgccaaaagcttttgctagccatcataattggtacttgacaaca

cttgcttctttatcagacagtagtacaaatcacaaagaattcttgtcctc

aaaactagtctatgcttatactaatgccatcaatggttttagtgcaagtc

tttctccttctgaatttgaagccataaaaaattctccaggttatgtttct

tcaattaaggatatgtcagttaaaattgacacaactcacacatcccaatt

ccttggcctaaactctgagtctggtgtatggccaacgtccgactatggta
```

-continued

```
aagatatcataattggcttagttgatactggaatatggccagagagtaaa

agctatagtgattatgggattagtgaagtaccatcaagatggaaaggaga

atgtgaaagtggcattgagttcaattcctctttgtgtaacaagaaaatca

ttggcgctcgttacttcaataaaggcctacttgccaacaatccaaatctt

aacatttcaatgaattctgctagagatacagatggacatggaactcacac

ttcttccacagctgcgggaagttatgtcgagggtgcatcttattttggct

atgccaccggcactgctattggcatagcaccaaaggctcatgtggctatg

tacaaggctctatgggaagaaggtgtatacttgtctgatgttcttgctgc

aattgatcaagcaattacagatggtgtagatgttttatccttgtcattag

gcatagacgcgattccactacacgaagatcctgtggcaattgccgcattt

gctgcattggagaaaggtatatttgtttccacctctgcaggaaatgaagg

gccttattatgagactttgcacaatggaacaccttgggtgctaactgttg

cagctggcacagttgaccgcgaatttattggcgcattaactcttggaaat

ggagtttcagtcactggcttatcgctctaccctgggaattctagttcaag

tgaaagctccattgtctatgttgaatgccaagatgacaaggaactgcaaa

aaagtgcacacaatattgttgtctgccttgacaagaatgattcggtcagt

gagcatgtgtacaatgtgagaaattcaaaagttgctggggctgtcttcat

aactaatataactgatttggaattctacctccaaagcgaattcccggctg

tgttcttgaacttacaagagggtgataaagttctagagtacattaagagc

aactctgcacctaaaggaaaacttgaattccgagtgacacatattggtgc

taaaccagcaccaaaagttgctacctatagctcaagaggaccgtcaccga

gctgtccaagtatcctcaagcctgatctcatggctcctggtgccttaata

ctagcttcatggccacaacaatcaccagtgactgatgttacctcaggaaa

actttttagtaacttcaatattatatctggtacatcaatgtcatgtccac

atgcttctggtgtagcagcacttctaaaagccgcacaccctgaatggagc

cctgcagccatccgatctgccatgatgaccacttccaatgcgatggacaa

cacacaaagtcccatccgagacataggtagtaagaatgctgctgctactc

ctctagccatgggagctggccatatcgatccaaacaaggcactagatcct

ggacttatctatgatgcgacaccacaagattatgtcaatcttctctgtgc

tctgaacttcacatccaaacaaataaaaaccatcacaagatcctcatctt

atacttgctccaacccatcattggacttaaactatccatctttcattgga

tttttcaatgggaacagcagcgagtcggatcctagaaggatacaagaatt

ccagaggaccgtgactaatattggagatggtatgtcagtatacacagcaa

aattgaccacaatgggtaaatttaaagttaatcttgtacctgaaaagttg

gttttcaaagagaagtatgaaaagttgagctacaagctaagaatagaagg

tccattagttatggatgatattgtggtttatggttctttgagctgggtag

aaactgaaggtaaatatgtggttagaagtccaattgttgccacaagcata

aaagtagatcctttgacaggacacaactga
```

Particularly preferred is a *Solanum lycopersicum* sequence SEQ ID No. 20, whereby amino acid residues 1 to 150, preferably 1 to 140, more preferably 1 to 130, more preferably 1 to 120, more preferably 1 to 110, in particular 1 to 102, of SEQ ID No. 20 represent the signal peptide and propeptide region:

```
                                          (SEQ ID No. 20)
MANYIALCIWLLSIIQLAKSETYIIHMDLSAMPKAFSSHYNWYLTTLFSV

SDSKDLLSSKLVYTYTNAINGFSASLSPSEIEAIKNSPGYVSSIKDMSVK

VDTTHTSQFLGLNSESGVWPKSDYGKDVIVGLVDTGIWPESRSYSDDGMN

EVPSRWKGECESGTQFNTSLCNKKLIGARYFNKGLLANNPNLTISMDSAR

DTDGHGTHISSTAAGSRVEGASFFGYAAGTATGVAPKAHVAMYKALWEEG

VFLSDILAAIDQAIADGVDVLSLSLGIDALPLYEDPVAIAAFAALEKGIF

VSTSAGNEGPFLETLHNGTPWVLTVAAGTVDREFIGTVTLGNGVSVTGLS

LYPGNSSSSESSISFVDCQDDKELQKNAHRIVVCIDNNDSVSEDVYNVRN

SKVSGAVFITNSTDLEFYLQSEFPAVELNIQEGDKVLEYVRSDSAPNAKL

EFQVTRIGAKPAPKVASYSSRGPSPSCPTILKPDLMGPGALILASWPQQT

PVTEVTSGKLYSNFNIISGTSMSCPHASGVAALLKSAHPEWSPAAIRSAM

MTTAYVLDNTQSPIQDVGLKNGVATPLAMGAGHIDPNKALDPGLIYDATP

QDYVNHLCGLNFTSKQIQTITRSSTYTCSNPSLDLNYPSFIGYFNRNSSD

SDPKRIQEFKRTVTNLQDGTSVYTAKLTPMGKFKVSVVPNKLTFKEKYEK

QSYKLRIEGPIIMDDIVVDGSLSWMETRGKYIVKSPIVATSIRVDPLRGH

N
```

A nucleic acid sequence encoding the *Solanum lycopersicum* subtilisin-like serine protease may comprise SEQ ID No. 21, whereby nucleotide residues 1 to 450, preferably 1 to 420, more preferably 1 to 390, more preferably 1 to 360, more preferably 1 to 330, in particular 1 to 306, of SEQ ID No. 21 encode the signal peptide and the propeptide region:

```
                                          (SEQ ID No. 21)
atggcaaattatattgccttgtgtatttggttgctttctataattcaatt

ggcaaagtcagaaacttatatcattcatatggatttgtcagccatgccaa

aagctttttctagccattataattggtacttgactacactttttttcggtg

tcagatagcaaagacttgttgtcctctaaactagtttatacttatactaa

tgccatcaatggtttcagtgcaagtctttctccttctgagatagaagcta

ttaagaattctccgggttatgtttcttcgattaaggatatgtcggttaaa

gttgacacaacccacacatctcaattccttggccttaactctgagtctgg

tgtatggccaaagtcggattatggcaaagatgttatagttggattagttg

acactgggatatggccagagagtagaagttatagtgatgatgggatgaat

gaagtaccatcaagatggaaaggagaatgtgaaagtggaactcagttcaa

tacctctttgtgcaataagaaactcattggcgctcgttacttcaataaag

gcctacttgctaacaacccgaatcttaccatttcgatggattctgctcgt

gatacggatggacatgggactcacacttcttccacggctgctggaagtcg

tgtagagggtgcatctttttttggatatgctgctggaactgctacaggtg

tagcaccaaaggctcatgtggccatgtacaaggctctatgggaagaaggt

gtattcttgtctgatattcttgcagcaattgatcaagcaattgcagatgg
```

-continued

```
tgtagatgtattgtccttgtcattaggcattgatgcgcttcctttatacg

aagatcctgttgcaattgccgcatttgctgcactggagaaaggcatattt

gtttctacatctgcaggaaatgaagggcctttttttggaaactttgcacaa

tggaacgccttgggtgctcactgttgctgctggcacagttgaccgggagt

ttattggcacagtaacacttggaaatggagtttcggtcactggattatcg

ctctaccctgggaactctagttcaagtgaaagctccattagcttcgttga

ttgccaagatgataaggaactgcagaaaaatgcacacagaatagtggtct

gcattgacaataatgattcagttagcgaggacgtctacaatgtaagaaat

tcaaaagtttctggtgcagtcttcataactaattcaactgacttggaatt

ctatctccaaagtgaatttcccgcggtgtttttgaacattcaagagggtg

ataaagttcttgagtacgttaggagtgactctgcacctaacgcaaagctt

gaattccaagtgacgcgtattggtgctaaaccagcaccaaaagttgctag

ctatagctcaagaggaccatcaccaagctgtcctacaattctaaagcctg

accttatgggtcctggtgcattaatacttgcttcatggccacaacaaaca

ccagtaactgaagttacctcgggaaaactttatagtaacttcaacattat

atcaggcacatcaatgtcttgtccacatgcttctggtgtagcagcacttc

taaaaagtgcacaccctgaatggagccctgctgctatccgatccgccatg

atgaccacagcctatgtattggacaacacacaaagccccatccaagacgt

aggtctgaagaatggtgttgctactcctctagctatgggagctggccata

tcgatccaaacaaagcgttggatcccggactcatctatgatgcaacacca

caagattatgttaaccacctctgtggtttgaacttcacatccaaacaaat

acaaaccatcacaagatcctcaacttacacttgctccaacccatcattag

acttgaactatccatcattcattggctatttcaaccggaatagcagcgat

tcggatcctaaaaggattcaagaattcaaaagaacagtgactaacttaca

agatggtacatcagtatacacagcaaagctcactccaatgggtaaattta

aagttagtgttgtacctaataagttgactttcaaagaaaagtatgaaaaa

caaagctataagctaagaatagaaggtccaataattatggatgatattgt

ggttgatggttcattgagctggatggaaactagaggaaaatacatagtta

aaagtccaattgttgcaacaagtataagagtggatcctttgagaggacat

aactga
```

Particularly preferred is a *Solanum tuberosum* sequence SEQ ID No. 22, whereby amino acid residues 1 to 150, preferably 1 to 140, more preferably 1 to 130, more preferably 1 to 120, more preferably 1 to 110, in particular 1 to 102, of SEQ ID No. 22 represent the signal peptide and propeptide region:

```
                                          (SEQ ID No. 22)
MANHIALCIWLLSIIQLAKSETYIIHMDLSAMPKAFSSHHNWYLTTLSSV

SDSKDLLSSKLVYTYTNAINGFSASLSPSEIEAIKNSPGYVSSIKDMSVK

VDTTHISQFLGLNSESGVWPKSDYGKDVIVGLVDTGIWPESRSYSDDGMN

EVPSRWKGECESGTQFNSSLCNKKLIGARYFNKGLLANNPNLTISMDSSR

DTDGHGTHTSSTAAGSRVEGASFFGYAAGTATGVAPKAHVAMYKALWEEG
```

-continued

```
VELSDILAAIDQAIEDGVDVLSLSLGIDALPLYEDPVAIAAFAALEKGIF

VSTSAGNEGPFLETLHNGTPWVLIVAAGTVDREFIGTLTLGNGVSVTGLS

LYPGNSSSSERSISYVDCQDDKELQKNAHKIVVCIDKSDSVSEDVYNVRN

SKVSGAVFITNSTDLEFYLQSEFPAVFLNIQEGDKVLEYVRSEAAPNAKL

EFQVTRIGAKPAPKVASYSSRGPSPSCPIILKPDLMGPGALILASWPQQT

PVTEVTSGKLYSNFNIISGTSMSCPHASGVAALLKSAHPEWSPAAIRSAM

MTTAYVLDNTQSPIQDIGLKNGVATPLAMGAGHIDPNKALDPGLIYDATP

QDYVNLLCALNFTSKQIQTITRSSTYTCSNPSLDLNYPSFIGYFNRNSSD

SDPKRIQEFIRTVTNLQDGTSVYTAKITPMGKFKVSVVPNKLIFKEKYEK

QSYKLRIEGPIIMDDIVVDGSLSWMETRGKYIVKSPIVATSIRVDPLRGH

N
```

A nucleic acid sequence encoding the *Solanum tuberosum* subtilisin-like serine protease may comprise SEQ ID No. 23, whereby nucleotide residues 1 to 450, preferably 1 to 420, more preferably 1 to 390, more preferably 1 to 360, more preferably 1 to 330, in particular 1 to 306, of SEQ ID No. 23 encode the signal peptide and the propeptide region:

```
                                          (SEQ ID No. 23)
atggcaaatcatattgccttgtgtatttggttgctttctataattcaatt

ggcaaagtcagaaacttatatcattcatatggatttgtcagccatgccaa

aagctttttctagccatcataattggtacttgactacactttcttctgta

tcagatagcaaagacttgttgtcctctaaactagtttatacttatactaa

tgccatcaatggtttcagtgcaagtctttctccttctgagatagaagcta

ttaagaattctcccggctatgtttcttcgattaaggatatgtcggttaaa

gttgacacaactcacacatctcaattccttggccttaactctgagtctgg

tgtatggccaaagtctgattatggcaaagatgtcatagttggattagttg

acactgggatatggccagagagtagaagttatagtgatgatgggatgaat

gaagtaccatcaagatggaaaggagaatgtgaaagtggaactcagttcaa

ttcctctttgtgcaataagaaactcattggcgctcgttacttcaataaag

gcctacttgctaacaacccgaatcttaccatttcgatggattcttctcgt

gatacggatggacatgggactcatacttcttccacggctgctggaagtcg

tgtagagggtgcatctttttttggctatgccgctggaacagctacaggtg

tagcaccaaaggctcatgtggccatgtacaaggctctatgggaagaaggt

gtattcttgtctgatattcttgcagcaattgatcaagcaattgaagatgg

tgtagatgtattgtcgttgtcattaggcattgacgcgcttccattatacg

aagatcctgttgcaattgctgcatttgctgcactggagaaaggcatattt

gtttctacatctgcaggaaatgaagggccatttttggaaactttgcacaa

tggaacaccttgggtgctcactgttgctgctggcacggttgaccgtgagt

ttattggcacactaacacttggaaatggagtttcggtcactggattatcg

ctctaccctgggaattctagttcaagtgaacgctccattagctatgttga

ttgccaagatgataaggaactgcagaaaaatgcacacaaaatagtggtct

gcattgacaagagtgattcagttagcgaagacgtctacaatgtaagaaat
```

-continued

```
tcaaaagtttctggtgcagtcttcataactaattcaactgacttggaatt

ctacctccaaagtgaatttcctgcagtgtttttgaacattcaagagggtg

ataaagttcttgagtatgttaggagtgaggctgcacctaacgcaaagctt

gaattccaagtgacgcgtattggtgctaaaccagcaccaaaagttgctag

ctatagctcaagaggaccatcaccaagttgtcctataattctcaagcctg

acctcatgggtcctggtgccttaatacttgcttcatggccacaacaaaca

ccagtaactgaagttacctcaggaaaactttatagtaacttcaacattat

atcaggcacatcaatgtcttgtccacatgcttctggtgtagcagcacttc

taaaaagtgcacaccctgaatggagccctgctgctatccgatccgccatg

atgaccacagcctatgtattggacaacacacaaagccccatccaagacat

aggtttgaagaatggtgttgctactcctctagctatgggagctggccata

tcgatccaaacaaggcgttggatcccggactcatctatgatgcaacacca

caagattatgttaatctcctttgtgctttgaacttcacatccaaacaaat

acaaaccatcacaagatcctcaacttacacttgctccaacccatcattag

acttgaactatccatctttcattggctatttcaaccggaacagcagcgat

tcagatcctaaaaggattcaagaattcataagaacagtgacaaacttaca

agatggtacatcagtatacacagcaaagatcactccaatgggtaaattta

aagttagtgttgtacctaataagttgattttcaaagaaaagtatgaaaag

caaagctacaagctaagaatagaaggtccaataattatggatgatattgt

ggttgatggttccttgagttggatggaaactagaggaaaatacatagtca

aaagtccaattgttgcaacaagtataagagtggatcctttgagaggacat

aactga
```

According to a preferred embodiment of the present invention the proteolytic activity of the at least one serine protease in the genetically modified plant or plant cell is at least 10%, preferably at least 25%, more preferably at least 50%, more preferably at least 70%, more preferably at least 80%, more preferably at least 90%, more preferably at least 95%, in particular 100%, reduced compared to its activity in the wild-type plant or plant cell. A preferred method for determining the proteolytic activity is for example the method described by Twining, 1984, Anal. Biochem. 143, 30-34.

According to a particularly preferred embodiment of the present invention said at least one serine protease of the wild-type plant or plant cell is mutated in the genetically modified plant or plant cell at at least one position of its amino acid sequence to reduce its proteolytic activity.

The proteolytic activity of a protease can be influenced by introducing one or more mutations within the amino acid sequence of said protease. The mutations may involve substitution, deletion or introduction of at least one amino acid residue within the amino sequence of the protease. The effect of the introduction of the at least one mutation can be determined by using an assay for determining the proteolytic activity in the mutated variant and comparing these results with the results of a proteolytic activity assay with a non-mutated version of the same protease.

Serine proteases require for their enzymatic activity a catalytic triad. In order to reduce the proteolytic activity of such proteases one or more amino acid residues of this catalytic triad may be substituted or deleted. Hence, the serine protease activity is preferably reduced by at least one amino acid substitution in the catalytic triad of a serine protease motif.

The proteolytic activity of the serine proteases of the present invention can be preferably reduced by mutating at least one amino acid residue (substitution or deletion) within the catalytically active fragment of said serine proteases.

"Catalytically active fragment" or "enzymatically active fragment", as used herein, refers to a polypeptide fragment that contains the catalytically active domain of a protease sufficient to exhibit activity. A catalytically active fragment is the portion of a protease that, under appropriate conditions, can exhibit catalytic activity and is able to cleave a bond in a peptide, polypeptide or protein. Typically, a catalytically active fragment is a contiguous sequence of amino acid residues of a protease that contains the catalytic domain and required portions for recognizing the substrate to be cleaved. A preferred enzymatically/catalytically active fragment of a protease lacks amino acid residues 1 to 200, preferably 5 to 190, more preferably 10 to 180, more preferably 15 to 170, more preferably 15 to 160, more preferably 20 to 150, more preferably 25 to 125, more preferably 1 to 115, even more preferably 1 to 102-110 of a wild-type serine protease according to the present invention (e.g. SEQ ID No. 2, 4, 6, 8, 10, 14, 16, 18, 20 or 22).

According to a preferred embodiment of the present invention the catalytically active fragment of a subtilisin-like serine protease comprises or consists of an amino acid sequence selected from the group consisting of amino acid residues 101 to 770, preferably 106 to 770, more preferably 108 to 770, more preferably 109 to 770, more preferably 111 to 770, more preferably 112 to 770, more preferably 113 to 770, more preferably 116 to 770, more preferably 121 to 770, in particular 110 to 770, of SEQ ID No. 2; amino acid residues 101 to 768, preferably 106 to 768, more preferably 107 to 768, more preferably 109 to 768, more preferably 111 to 768, more preferably 112 to 768, more preferably 113 to 768, more preferably 116 to 768, more preferably 121 to 768, in particular 108 to 768, of SEQ ID No. 4; amino acid residues 101 to 768, preferably 106 to 768, more preferably 107 to 768, more preferably 109 to 768, more preferably 111 to 768, more preferably 112 to 768, more preferably 113 to 768, more preferably 116 to 768, more preferably 121 to 768, in particular 108 to 768, of SEQ ID No. 6; amino acid residues 101 to 783, preferably 106 to 783, more preferably 107 to 783, more preferably 109 to 783, more preferably 111 to 783, more preferably 112 to 783, more preferably 113 to 783, more preferably 116 to 783, more preferably 121 to 783, in particular 108 to 783, of SEQ ID No. 8; amino acid residues 101 to 773, preferably 106 to 773, more preferably 107 to 773, more preferably 109 to 773, more preferably 111 to 773, more preferably 112 to 773, more preferably 113 to 773, more preferably 116 to 773, more preferably 121 to 773, in particular 108 to 773, of SEQ ID No. 10; amino acid residues 102 to 759, preferably 107 to 759, more preferably 109 to 759, more preferably 110 to 759, more preferably 112 to 759, more preferably 113 to 759, more preferably 114 to 759, more preferably 117 to 759, more preferably 122 to 759, in particular 111 to 759, of SEQ ID No. 14; amino acid residues 102 to 762, preferably 107 to 762, more preferably 109 to 762, more preferably 110 to 762, more preferably 112 to 762, more preferably 113 to 762, more preferably 114 to 762, more preferably 117 to 762, more preferably 122 to 762, in particular 111 to 762, of SEQ ID No. 16; amino acid residues 102 to 759, preferably 107 to 759, more preferably 109 to 759, more preferably 110 to 759, more preferably 112 to 759, more preferably 113 to 759, more preferably 114 to 759, more preferably 117 to 759, more preferably 122 to 759, in particular 111 to 759, of SEQ ID No. 18; amino acid residues 94 to 751, preferably 99 to 751, more preferably 101 to 751, more preferably 102 to 751, more preferably 104 to 751, more preferably 105 to 751, more preferably 106 to 751, more preferably 109 to 751, more preferably 114 to 751, in particular 103 to 751, of SEQ ID No. 20; amino acid residues 94 to 751, preferably 99 to 751, more preferably 101 to 751, more preferably 102 to 751, more preferably 104 to 751, more preferably 105 to 751, more preferably 106 to 751, more preferably 109 to 751, more preferably 114 to 751, in particular 103 to 751, of SEQ ID No. 22.

The proteolytic activity of the serine proteases of the present invention can also be reduced by influencing the promoter region of their respective genes naturally occurring within the plant or plant cell. The promoter region is located at the 5' end of the nucleic acid region coding for the respective serine proteases and comprises typically 500 to 2000 nucleotides. Deletion, substitution or insertion of nucleotides within this region influences the transcription rate and consequently the proteolytic activity of the serine proteases within the plant and plant cell.

According to a preferred embodiment of the present invention a promoter of a gene encoding said at least one serine protease of the wild-type plant or plant cell is mutated in the genetically modified plant or plant cell at at least one position of its nucleic acid sequence to reduce its expression rate.

A mutation within said promoter may be a deletion or substitution within 100, preferably within 200, more preferably within 300, more preferably within 500, more preferably within 700, more preferably within 1000, nucleotides located adjacent and upstream to the 5' end of the coding region encoding said at least one serine protease of a plant or plant cell. Whether a mutation within said region results in a reduction or prevention of the expression rate of said at least one serine protease can be determined by methods known in the art and by comparing the expression rate of said at least one serine protease in a plant or plant cell modified within the aforementioned region with the expression rate of the same enzyme(s) in a wild-type plant or plant cell. In a preferred embodiment of the present invention up to 100, preferably up to 200, more preferably up to 300, more preferably up to 500, more preferably up to 700, more preferably up to 1000, nucleotides located adjacent and upstream to the 5' end of the coding region encoding said at least one serine protease of the wild-type plant or plant cell are deleted. In another preferred embodiment of the present invention 10 to 100, preferably 10 to 200, more preferably 50 to 300, more preferably 50 to 500, more preferably 100 to 700, more preferably 200 to 1000, nucleotides located adjacent and upstream to the 5' end of the coding region encoding said at least one serine protease of the wild-type plant or plant cell are deleted.

In a particularly preferred embodiment of the present invention at least 30%, preferably at least 40%, more preferably at least 50%, more preferably at least 60%, more preferably at least 70%, more preferably at least 80%, more preferably at least 90%, more preferably at least 95%, in particular 100%, of the coding region of the serine proteases of the present invention having at least 80%, preferably at least 85%, more preferably at least 90%, more preferably at least 95%, more preferably at least 96%, more preferably at least 98%, more preferably at least 99%, in particular 100%, sequence identity to a serine protease consisting of an amino acid sequence selected from the group consisting of SEQ ID No. 2, SEQ ID No. 4, SEQ ID No. 6, SEQ ID No. 8, SEQ ID No. 10, SEQ ID No. 14, SEQ ID No. 16, SEQ ID No. 18, SEQ ID No. 20 and SEQ ID No. 22, preferably SEQ ID No. 2 or SEQ ID No. 14, i.e. a nucleic acid sequence selected from the group consisting of SEQ ID No. 3, SEQ ID No. 5, SEQ ID No. 7, SEQ ID No. 9, SEQ ID No. 11, SEQ ID No. 15, SEQ ID No. 17, SEQ ID No. 19, SEQ ID No. 21 and SEQ ID No. 23, preferably SEQ ID No. 3 or SEQ ID No. 15, are deleted in the plant or plant cell of the present invention by methods known in the art.

According to a preferred embodiment of the present invention an inhibitor (e.g. *Arabidopsis thaliana* subtilisin propeptide-like inhibitor 1, At1g71950; *A. thaliana* subtilisin propeptide-like inhibitor 2, At2g39851; S106g065370; S111g018590; Hohl M et al., 2017, J. Biol. Chem. 292, 6389-6401) of said at least one serine protease is overexpressed in the genetically modified plant or plant cell to reduce the expression rate of the at least one serine protease or to inhibit the proteolytic activity of the at least one serine protease.

In a particularly preferred embodiment of the present invention the serine protease inhibitor is *Arabidopsis thaliana* subtilisin propeptide-like inhibitor 1 (GenBank: AEE35257.1), *A. thaliana* subtilisin propeptide-like inhibitor 2 (GenBank: AEC09739.1), S106g065370 (SEQ ID No. 33) or Sl11g018590 (SEQ ID No. 34).

(SEQ ID No. 33)
MMKKDQILSSILLFFFLFTAFITTMADSQASSQPSNESKVHIVYTEQPKD

QEPEEYHIKTLTSVLGSEEAAKEALLYSYKHAASGFSAKLTAEQVSELSK

LPGVLQVVPSQTVQLHTGRV (SEQ ID No. 34)
MQKIQIIFLVFLLLFVADCEEAKVYIVFTENPQPKEFHIKTLASVLGSED

AAREALIYSYKHVISGFAARLTPEQVSELAKKPGVLEIVPSRTYHLDGPK

LK

According to a preferred embodiment of the present invention the genetically modified plant or plant cell comprises at least one exogenous nucleic acid molecule encoding for at least one protein or polypeptide of interest.

The genetically modified plant or plant cell can be used to produce/express at least one protein or polypeptide of interest which is not naturally occurring in said plant or plant cell. In order to allow the recombinant expression of heterologous polypeptides and proteins the respective nucleic acid molecule encoding said polypeptides and proteins are introduced into the plant or plant cell of the present invention.

The terms "exogenous protein", "exogenous polypeptide", "heterologous protein" or "heterologous polypeptide", as defined herein, all refer to a protein or polypeptide that is not expressed by the plant or plant cell in nature, i.e. is not naturally occurring in plants and plant cells. This is in contrast with a homologous protein which is a protein naturally expressed by a plant or plant cell. The heterologous expression of polypeptides and proteins within a host cell can be achieved by means and methods known in the art and described below for the polypeptide of the present invention.

The exogenous nucleic acid molecule of the present invention can be a vector, preferably a plant vector, or a nucleic acid molecule carrying elements allowing cloning and/or the recombinant expression of heterologous proteins or polypeptides within a plant or plant cell.

The vector of the present invention can be used to clone the nucleic acid molecule of the present invention, as a shuttle or as an expression vector in host cells. Expression vectors may include an expression cassette which comprises various specified nucleic acid elements which permit transcription of a particular nucleic acid in a host cell. Typically, expression cassettes comprise, among other sequences, a nucleic acid to be transcribed, a promoter and a terminator.

The vector of the present invention can be designed to be integrated into the genome of the host cell. Alternatively the vector is designed to not integrate into the genome of a host cell allowing transient expression of the nucleic acid molecule of the present invention. In the latter case the vector remains in a non-integrated state free within the cell.

A "vector" according to the present invention refers to a nucleic acid used to introduce the nucleic acid molecule of the present invention into a host cell. Expression vectors permit transcription of a nucleic acid inserted therein.

In order to enable a host cell to express a polypeptide of the present invention encoded by the nucleic acid molecule as defined above the vector of the present invention comprises a promoter operably linked to the nucleic acid molecule.

As used herein, "operably linked" refers to a functional linkage between a promoter and the nucleic acid molecule encoding the polypeptide of the present invention, wherein the promoter sequence initiates and mediates transcription of the DNA sequence corresponding to said nucleic acid molecule.

The term "promoter", as used herein, refers to a region of a nucleic acid molecule upstream from the start of transcription and involved in recognition and binding of RNA polymerase and other proteins to initiate transcription. Promoters are able to control (initiate) transcription in a cell. Plant promoters are able of initiating transcription in plant cells whether or not its origin is a plant cell. Such promoters include promoters obtained from plants, plant viruses and bacteria which comprise genes expressed in plant cells such as *Agrobacterium* or *Rhizobium*. The promoter used in the vector of the present invention can be "inducible" or "repressible", i.e. under environmental control. Such promoters can be controlled by changing the cultivation conditions (e.g. temperature) or by adding specific substances. Of course, the promoter used in the vectors of the present invention may be a "constitutive" promoter. Constitutive promoters are active under most environmental conditions and express continuously a protein or polypeptide of interest.

According to a preferred embodiment of the present invention the promoter is selected from the group consisting of promoters active in plants and plant cells, like the cauliflower mosaic virus 35S promoter, opine (octopine, nopaline, etc.) synthase promoters, actin promoter, ubiquitin promoter, etc.

In order to prevent transcriptional activation of downstream nucleic acid sequences by upstream promoters the vector of the present invention may comprise a "terminator" or "terminator sequence". According to a preferred embodiment of the present invention the vector comprises a terminator which is preferably a g7T terminator.

According to a preferred embodiment of the present invention the exogenous/heterologous polypeptide or protein is of animal origin, preferably a mammalian, more preferably a human, polypeptide.

Polypeptides and proteins "of animal origin", as used herein, refers to polypeptides which are not naturally occurring in plants and plant cells or any other non-animal organism. Polypeptides of animal origin can be derived from the genome of animals, preferably mammals, and are usually expressed in animals.

According to a further embodiment of the present invention the heterologous animal polypeptide is an antibody or a variant thereof.

Examples of heterologous polypeptides and proteins that can be advantageously produced by the plants or plant cells of the present invention include antibodies or variants thereof which are selected from the group consisting of monoclonal antibodies, chimeric antibodies, humanized antibodies, human antibodies, multispecific antibodies, Fab, Fab', $F(ab')_2$, antigen-binding Fc fragments (Fcab) and derivatives thereof, Fv, domain antibodies (dAb), complementarity determining region (CDR) fragments, CDR-grafted antibodies, single-chain antibodies (ScFv), single chain antibody fragments, diabodies, triabodies, tetrabodies, minibodies, linear antibodies, chelating recombinant antibodies, tribodies, bibodies, intrabodies, nanobodies, small modular immunopharmaceuticals (SMIP), camelized antibodies, VHH containing antibodies and polypeptides that comprise at least a portion of an immunoglobulin that is sufficient to confer specific antigen binding to the polypeptide, such as one, two, three, four, five or six CDR sequences.

According to a particularly preferred embodiment of the present invention the antibody is an antibody binding to a human immunodeficiency virus (HIV) surface protein.

As used herein, the term "specific for" can be used interchangeably with "binding to" or "binding specifically to". These terms characterize molecules that bind to an antigen or a group of antigens with greater affinity (as determined by, e.g., ELISA or surface plasmon resonance spectroscopy assays) than other antigens or groups of antigens. According to the present invention molecules "specific for" an antigen may also be able to bind to more than one, preferably more than two, more preferably more than three, even more preferably more than five, antigens. Such molecules are defined to be "cross-reactive" (e.g. cross-reactive immunoglobulins, cross-reactive antigen binding sites).

The antibody expressed by the plant cell and plant of the present invention is preferably an antibody selected from the group consisting of 2F5 (Zwick et al., 2004, J. Virol. 78, 3155-3161), 2G12 (Doores et al., 2010, J. Virol. 84, 10690-10699), PG9 (Loos et al., 2015, Proc. Natl. Acad. Sci. USA 112, 12675-12680), PG16 (Pancera et al., 2013, Nat. Struct. Mol. Biol. 20, 804-813) and variants thereof.

It is known that non-cleaved antibodies may have a greater binding affinity to an antigen compared to their cleaved versions. This in effect is particularly significant for antibodies like 2F5, 2G12, PG9, PG16 and variants thereof. Therefore, it is particularly advantageous to provide efficient tools for producing non-cleaved 2F5, 2G12, PG9, PG16 and variants thereof.

According to a preferred embodiment of the present invention the antibody variant is selected from the group consisting of 2G12 comprising modifications at $I^{H19}$ (Doores et al., 2010, J. Virol. 84, 10690-10699).

According to a preferred embodiment of the present invention the antibody variant is selected from the group consisting of PG9 comprising modifications at $N^{L23}$ (Loos et al., 2015, Proc. Natl. Acad. Sci. USA 112, 12675-12680).

According to a preferred embodiment of the present invention the antibody variant is selected from the group consisting of PG9 comprising modifications at $T^{L94}$, $R^{L95}$ and $R^{L95A}$ (Pancera et al., 2013, Nat. Struct. Mol. Biol. 20, 804-813).

According to a preferred embodiment of the present invention the plant or plant cell is of the genus *Nicotiana* and preferably a species selected from the group consisting of *Nicotiana benthamiana* and *Nicotiana tabacum.*

Further preferred plants to be used according to the present invention include *Nicotiana benthamiana*, tobacco (*Nicotiana tabacum*), *Nicotiana* spp, *Arabidopsis thaliana*, tomato (*Solanum lycopersicum*), potato (*Solanum tuberosum*), duckweed (*Lemna minor*), mosses (e.g. *Physcomitrella*), corn (*Zea mays*), rice (*Oryza sativa*), wheat (*Triticum aestivum*), peas (*Pisum sativum*), flaxseed (*Linum usitatissimum*) and rapeseed (*Brassica napus*), in particular the *Nicotiana benthamiana* line C105 (Strasser R et al. Plant Biotechnol J 6(2008):392-402).

A further aspect of the present invention relates to a serine protease consisting of an amino acid sequence selected from the group consisting of SEQ ID No. 2, SEQ ID No. 4, SEQ ID No. 6, SEQ ID No. 8, SEQ ID No. 10, SEQ ID No. 14, SEQ ID No. 16, SEQ ID No. 20 and SEQ ID No. 22, preferably SEQ ID No. 2 or SEQ ID No. 14.

Another aspect of the present invention relates to a nucleic acid molecule encoding a serine protease according to the present invention.

The nucleic acid molecule of the present invention encoding a serine protease as defined herein can be used to recombinantly express said serine protease. The specificity of the serine proteases of the present invention can be used in methods or organisms where such a cleavage specificity is desired. These methods may involve the use of non-plant organisms like animals or microorganisms.

The nucleic acid molecule of the present invention can be part of a vector which can be used for cloning or expression purposes. Respective vectors are well-known in the art.

The nucleic acid according to the present invention may encode a subtilisin-like serine protease and may comprise or consist of a nucleic acid sequence selected from the group consisting of SEQ ID No. 3, SEQ ID No. 5, SEQ ID No. 7, SEQ ID No. 9, SEQ ID No. 11, SEQ ID No. 15, SEQ ID No. 17, SEQ ID No. 21 and SEQ ID No. 23, preferably SEQ ID No. 3 or SEQ ID No. 15.

The nucleic acid molecule encoding a subtilisin-like serine protease comprising or consisting of a nucleic acid sequence selected from the group consisting of SEQ ID No. 3, SEQ ID No. 5, SEQ ID No. 7, SEQ ID No. 9, SEQ ID No. 11, SEQ ID No. 15, SEQ ID No. 17, SEQ ID No. 21 and SEQ ID No. 23, preferably SEQ ID No. 3 or SEQ ID No. 15, may comprise a nucleotide stretch encoding a tag sequence for detection and affinity purification, preferably at the N- or C-terminus, more preferably at the C-terminus of the polypeptide. This tag may consist of 3 to 60, preferably 3 to 45, more preferably 6 to 30, more preferably 3 to 18, in particular 18, nucleotides (n). In a particularly preferred embodiment of the present invention the tag consists of or comprises the nucleic acid stretch encoding the amino acid sequence HHHHHH (SEQ ID NO: 35).

Another aspect of the present invention relates to a polypeptide encoded by a nucleic acid molecule according to the present invention, preferably a polypeptide comprising or consisting of an amino acid sequence selected from the group consisting of SEQ ID No. 2, SEQ ID No. 4, SEQ ID No. 6, SEQ ID No. 8, SEQ ID No. 10, SEQ ID No. 14, SEQ ID No. 16, SEQ ID No. 20 and SEQ ID No. 22, most preferably SEQ ID No. 2 or SEQ ID No. 14.

The serine proteases of the present invention may comprise a tag sequence for detection and/or affinity purification, preferably at the N- or C-terminus, more preferably at the C-terminus. This tag may consist of 1 to 20, preferably 1 to 15, more preferably 2 to 10, more preferably 2 to 6, in particular 6 amino acid residues. In a particularly preferred embodiment of the present invention the tag consists of or comprises the amino acid sequence HHHHHH (SEQ ID NO: 35).

The terms "polypeptide" and "protein" refer to a polymer of amino acid residues, wherein a "polypeptide" polymer may comprise more than 5 amino acid residues and a "protein" polymer may comprise more than 100 amino acid residues. The term "polypeptide" may, thus, include also "proteins".

Yet, another aspect of the present invention relates to a plant or plant cell capable of cleaving a polypeptide preferably of animal origin heterologously produced in said plant or plant cell comprising a nucleic acid molecule or a vector according to the present invention.

In order to support the correct folding of heterologous, preferably mammalian, more preferably human, proteins or polypeptides expressed in plants and plant cells said proteins or polypeptides may be fused to another polypeptide or peptide, i.e. a fusion partner (see e.g. Sainsbury et al., 2016, Front. Plant Sci. 7, 141). Said fusion partner is linked via a peptide to the protein or polypeptide to be heterologously expressed whereby said peptide comprises cleavage sites which are recognized and cut by the serine proteases of the present invention. The removal of the aforementioned fusion partner can be done directly in the plant and plant cell of the present invention which expresses said serine protease.

The proteins and polypeptides heterologously produced in said plant or plant cell may be fused to peptidic tags which can be used to facilitate the purification of the proteins. Said peptidic tags may have, for instance, a binding affinity to other chemical moieties which may be immobilized on a solid support. The peptidic tags are linked via a peptide comprising a cleavage site which is recognized and cut by the serine proteases of the present invention to the heterologously produced proteins and polypeptides.

The plant and plant cell of the present invention may carry the nucleic acid molecule of the present invention in a non-integrated form (e.g. as a vector) or may be a "transgenic plant" or "transgenic plant cell". Such a plant or plant cell comprises within its genome a heterologous nucleic acid molecule. This heterologous nucleic acid molecule is usually stably integrated within the genome such that the polynucleotide is passed on to successive generations. In order to allow the plant and plant cell to express the polypeptide of the present invention, its encoding nucleic acid molecule is operably linked to a promoter.

The nucleic acid molecule and the vector according to the present invention enable a plant or plant cell to cleave polypeptides and proteins expressed in said plant or plant cell. Therefore, the transgenic plant or plant cell of the present invention comprise preferably a nucleic acid molecule encoding a heterologous polypeptide operably linked to a promoter region.

Another aspect of the present invention relates to a method for producing at least one protein or polypeptide of interest by cultivating a genetically modified plant or plant cell according to the present invention.

Yet, another aspect of the present invention relates to a method of recombinantly producing a non-cleaved polypeptide of animal origin comprising the step of cultivating a plant or plant cell according to the present invention.

Methods and means to cultivate recombinant plants and plant cells are known in the art (e.g. Plant Biotechnology and Genetics: Principles, Techniques, and Applications, edited by C. N. Stewart, 2008, Wiley, ISBN 978-0-470-04381-3).

EXAMPLES

Materials and Methods

1. Cloning of Neutralizing Anti-HIV Antibody 2G12 and Variant Thereof

The signal peptide of barley α-amylase (amino acid residues 1 to 24 of the amino acid sequence of acc. no. CAX51374.1) was cloned into MagnIcon vectors pICH26033 and pICH31160 (Niemer M et al. Biotechnol J 9 (2014):493-500) to give rise to pICHα26033 and pICHα31160. The sequences encoding the 2G12 heavy and light chains (omitting their authentic signal peptides) were amplified from the corresponding pDONR221 constructs (Loos A et al. Plant Biotechnol J 9 (2011):179-192) by PCR. The fragments thus generated were then inserted into the BsaI sites of pICHα31160 (heavy chain) and pICHα26033 (light chain). The domain-swapping point mutation I19R (Doores K J et al. J Virol 84 (2010):10690-10699) was introduced into the 2G12 heavy-chain sequence by site-directed mutagenesis. The mutated product was then cloned into pICHα31160 as outlined above.

2G12HC (SEQ ID No. 24; PDB-database: 1ZLS, 1ZLU, 1ZLV, 1ZLW, 2OQJ, 30AY, 30AZ, 3OB0) CDNA was PCR-amplified from pDONR221/2G12HC (Loos A et al. Plant Biotechnol J 9 (2011):179-192), without signal peptide but with 5'- and 3' BsaI restriction sites.

2G12HC consists of amino acid sequence SEQ ID No. 24, whereby the signal peptide of barley α-amylase is marked in bold and italic:

*MANKHLSLSLFLVLLGLSASLASG*EVQLVESGGGLVKAGGSLILSCGVSN
FRISAHTMNWVRRVPGGGLEWVASISTSSTYRDYADAVKGRFTVSRDDLE
DFVYLQMHKMRVEDTAIYYCARKGSDRLSDNDPFDAWGPGTVVTVSPAST
KGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHED
PEVKFNWYVDGVEVHNAKTKPREEQYNSTYRVVSVLIVLHQDWLNGKEYK
CKVSNKAFPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK

2G12HC is encoded by nucleotide sequence SEQ ID No. 25 (including a stop codon), whereby the nucleic acid stretch encoding the signal peptide of barley α-amylase is marked in bold and italic:

*atggcgaacaaacacttgtccctctccctcttcctcgtcctccttggcct*
*gtcggccagcttggcctcaggt*gaggtgcagctggtggagtctgggggag
gcctggtcaaggcgggaggatccctcatactctcctgtggagtctctaat
tttagaatctctgcccataccatgaattgggtccgccgggttccaggggg
ggggctggagtgggtcgcttccattagtacgagttccacttatagagact
atgcagacgctgtgaagggccgattcaccgtttccagagacgacctcgaa
gactttgtgtatttgcaaatgcacaaaatgagagtcgaagacacggctat
ttattactgcgccagaaagggatctgacagactaagcgacaacgatcctt -continued

```
ttgatgcctgggggccaggaacagtggtcaccgtctctcccgcctccacc
aagggcccatcggtcttcccctggcaccctcctccaagagcacctctgg
gggcacagcggccctgggctgcctggtcaaggactacttccccgaaccgg
tgacggtgtcgtggaactcaggcgccctgaccagcggcgtgcacaccttc
ccggctgtcctacagtcctcaggactctactccctcagcagcgtggtgac
cgtgccctccagcagcttgggcacccagacctacatctgcaacgtgaatc
acaagcccagcaacaccaaggtggacaagaaagttgagcccaaatcttgt
gacaaaactcacacatgcccaccgtgcccagcacctgaactcctgggggg
accgtcagtcttcctcttccccccaaaacccaaggacaccctcatgatct
cccggacccctgaggtcacatgcgtggtggtggacgtgagccacgaagac
cctgaggtcaagttcaactggtacgtggacggcgtggaggtgcataatgc
caagacaaagccgcgggaggagcagtacaacagcacgtaccgtgtggtca
gcgtcctcaccgtcctgcaccaggactggctgaatggcaaggagtacaag
tgcaaggtctccaacaaagccttcccagcccccatcgagaaaaccatctc
caaagccaaagggcagccccgagaaccacaggtgtacaccctgcccccat
cccgggatgagctgaccaagaaccaggtcagcctgacctgcctggtcaaa
ggcttctatcccagcgacatcgccgtggagtgggagagcaatgggcagcc
ggagaacaactacaagaccacgcctcccgtgctggactccgacggctcct
tcttcctctacagcaagctcaccgtggacaagagcaggtggcagcagggg
aacgtcttctcatgctccgtgatgcatgaggctctgcacaaccactacac
gcagaagagcctctccctgtctccgggtaaatga
```

2G12HC cDNA encoding an I19R mutation (SEQ ID No. 26; PDB-database: 30AU) was generated by site-directed mutagenesis, without signal peptide but with 5'- and 3' BsaI restriction sites.

2G12HC (encoding an I19R mutation) consists of amino acid sequence SEQ ID No. 26, whereby the signal peptide of barley α-amylase is marked in bold and italic:

*MANKHLSLSLFLVLLGLSASLASG*EVQLVESGGGLVKAGGSLRLSCGVSN
FRISAHTMNWVRRVPGGGLEWVASISTSSTYRDYADAVKGRFTVSRDDLE
DFVYLQMHKMRVEDTAIYYCARKGSDRLSDNDPFDAWGPGTVVTVSPAST
KGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHED
PEVKFNWYVDGVEVHNAKTKPREEQYNSTYRVVSVLIVLHQDWLNGKEYK
CKVSNKAFPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK

2G12HC (encoding an I19R mutation) is encoded by nucleotide sequence SEQ ID No. 27 (including a stop codon), whereby the nucleic acid stretch encoding the signal peptide of barley α-amylase is marked in bold and italic:

*atggcgaacaaacacttgtccctctccctcttcctcgtcctccttggcct*
*gtcggccagcttggcctcaggt*gaggtgcagctggtggagtctgggggag
gcctggtcaaggcgggaggatccctcagactctcctgtggagtctctaat
tttagaatctctgcccataccatgaattgggtccgccgggttccaggggg
ggggctggagtgggtcgcttccattagtacgagttccacttatagagact
atgcagacgctgtgaagggccgattcaccgtttccagagacgacctcgaa
gactttgtgtatttgcaaatgcacaaaatgagagtcgaagacacggctat
ttattactgcgccagaaagggatctgacagactaagcgacaacgatcctt
ttgatgcctgggggccaggaacagtggtcaccgtctctcccgcctccacc
aagggcccatcggtcttcccctggcaccctcctccaagagcacctctgg
gggcacagcggccctgggctgcctggtcaaggactacttccccgaaccgg
tgacggtgtcgtggaactcaggcgccctgaccagcggcgtgcacaccttc
ccggctgtcctacagtcctcaggactctactccctcagcagcgtggtgac
cgtgccctccagcagcttgggcacccagacctacatctgcaacgtgaatc
acaagcccagcaacaccaaggtggacaagaaagttgagcccaaatcttgt
gacaaaactcacacatgcccaccgtgcccagcacctgaactcctgggggg
accgtcagtcttcctcttccccccaaaacccaaggacaccctcatgatct
cccggacccctgaggtcacatgcgtggtggtggacgtgagccacgaagac
cctgaggtcaagttcaactggtacgtggacggcgtggaggtgcataatgc
caagacaaagccgcgggaggagcagtacaacagcacgtaccgtgtggtca
gcgtcctcaccgtcctgcaccaggactggctgaatggcaaggagtacaag
tgcaaggtctccaacaaagccttcccagcccccatcgagaaaaccatctc
caaagccaaagggcagccccgagaaccacaggtgtacaccctgcccccat
cccgggatgagctgaccaagaaccaggtcagcctgacctgcctggtcaaa
ggcttctatcccagcgacatcgccgtggagtgggagagcaatgggcagcc
ggagaacaactacaagaccacgcctcccgtgctggactccgacggctcct
tcttcctctacagcaagctcaccgtggacaagagcaggtggcagcagggg
aacgtcttctcatgctccgtgatgcatgaggctctgcacaaccactacac
gcagaagagcctctccctgtctccgggtaaatga 2G12LC (SEQ ID No. 28; PDB-database: 1ZLS, 1ZLU, 1ZLV, 1ZLW, 2OQJ, 3OAU, 3OAY, 3OAZ, 3OB0) CDNA was PCR-amplified from pDONR221/2G12LC (Loos A et al. Plant Biotechnol J 9 (2011):179-192), without signal peptide but with 5'- and 3' BsaI restriction sites.

2G12LC consists of amino acid sequence SEQ ID No. 28, whereby the signal peptide of barley α-amylase is marked in bold and italic:

*MANKHLSLSLFLVLLGLSASLASG*DVVMTQSPSTLSASVGDTITITCRAS
QSIETWLAWYQQKPGKAPKLLIYKASTLKTGVPSRFSGSGSGTEFTLTIS
GLQFDDFATYHCQHYAGYSATFGQGTRVEIKRTVAAPSVFIFPPSDEQLK
SGTASVVCLLNNFYPREAKVQWKVDNALQSGNSQESVTEQDSKDSTYSLS
STLTLSKADYEKHKVYACEVTHQGLSSPVTKSFNRGEC

2G12LC is encoded by nucleotide sequence SEQ ID No. 29 (including a stop codon), whereby the nucleic acid stretch encoding the signal peptide of barley α-amylase is marked in bold and italic:

*atggcgaacaaacacttgtccctctccctcttcctcgtcctccttggcct*

*gtcggccagcttggcctcaggt*gatgttgtgatgactcagtctccttcca ccctgtctgcatctgtcggagacacaatcaccatcacttgccgggccagt cagagtattgaaacctggttggcctggtatcagcagaagccagggaaagc cccaaaactcctaatctacaaggcgtctactttaaaaactggagtcccgt caagattcagcggcagtggatctggaacagagttcactcttaccatcagt ggcctgcagttcgatgactttgcaacttatcactgtcagcactatgctgg ttattcagcgacgttcggccaggggaccagggtggagatcaaacgaactg tggctgcaccatctgtcttcatcttcccgccatctgatgagcagttgaaa tctggaactgcctctgttgtgtgcctgctgaataacttctatcccagaga ggccaaagtacagtggaaggtggataacgccctccaatcgggtaactccc aggagagtgtcacagagcaggacagcaaggacagcacctacagcctcagc agcaccctgacgctgagcaaagcagactacgagaaacacaaagtctacgc ctgcgaagtcacccatcagggcctgagctcgcccgtcacaaagagcttca acaggggagagtgttag 2G12HC and 2G12HC (encoding an I19R mutation) were inserted into pICHα31160 in frame after the barley x-amylase signal peptide. 2G12LC was inserted into pICHα26033 in frame after the barley x-amylase signal peptide.

The vectors used for the expression of antibodies 2F5 and PG9 have been described (Niemer M et al. Biotechnol J 9 (2014):493-500).

All vectors were transformed into *Escherichia coli* by electroporation and upon sequence confirmation into the *Agrobacterium tumefaciens* strains GV3101pMP90RK or UIA143.

2. Cloning of Subtilisin-Like Serine Protease Constructs

RNA was extracted from 35-mg samples of leaves from 4-week-old *Nicotiana benthamiana* C105 μlants lacking plant-specific α1,3-fucosylation and β1,2-xylosylation (Strasser R et al. Plant Biotechnol J 6 (2008):392-402) using the SV Total RNA Isolation Kit (PROMEGA). First-strand cDNA was synthesized from 1 μg RNA using the RevertAid H Minus First Strand cDNA Synthesis Kit (THERMO SCIENTIFIC) and oligo $(dT)_{18}$ as primer. For expression in *Nicotiana benthamiana* C105 μlants, the coding sequences of the subtilisin-like serine proteases SBT1 and SBT2 (SEQ ID No. 3 and SEQ ID No. 15) were PCR-amplified using Q5 High-Fidelity DNA polymerase (NEW ENGLAND BIOLABS) and then inserted into a suitable expression vector, e.g. pPT2 (Strasser R et al. Biochem J 387 (2005):385-391) or PART27 (Schardor K et al. Science 354 (2016):1594-1597). After transformation into *E. coli* and sequence confirmation, all constructs were transformed into *Agrobacterium tumefaciens*, e.g. strain UIA143pMP90.

3. In Planta Expression of Monoclonal Antibodies

*Nicotiana benthamiana* C105 μlants were grown for 4-5 weeks at 24° C. with a 16-h light: 8-h dark photoperiod. Infiltration with agrobacteria carrying the respective expression vectors was then performed as reported previously (Strasser R et al. Plant Biotechnol J 6 (2008):392-402). Briefly, overnight cultures were pelleted and then resuspended in infiltration buffer (25 mM Mes buffer (pH 5.5), 25 mM $MgSO_4$, 0.1 mM acetosyringone) at an $OD_{600}$ of 0.2 (1.0 $OD_{600}$ corresponds to $5\times10^8$ cells/mL). In the case of 2G12 and PG9 expression, equal amounts of the strains carrying the respective heavy and light chain constructs were used. Infiltrated *N. benthamiana* leaves were harvested after 4-5 days.

4. Monoclonal Antibody (mAb) Purification

Leaf material (see item 3) infiltrated with the transformed *Agrobacterium tumefaciens* strains described under item 1 was crushed under liquid nitrogen, extracted twice for 20 min on ice with 0.1 M Tris/HCl (pH 7.0) containing 0.5 M NaCl, 40 mM ascorbic acid and 1 mM EDTA (2 mL per gram leaf wet weight). After a centrifugation step (4° C., 30 min, 27500 g), the extract was clarified by a series of filtration steps with pore sizes ranging from 10 μm to 0.2 μm (Roth, AP27.1, Roth, AP51.1, Roth, CT92.1, Roth, KH54.1). Antibodies were then purified by affinity chromatography on a column packed with 1 mL rProtein A Sepharose 4 Fast Flow (GE HEALTHCARE, 17-1279-01), using 0.1 M glycine/HCl (pH 3.0) for elution. Protein-containing eluate fractions were immediately neutralized by addition of 0.1 M Tris/HCl (pH 8.0), dialyzed against phosphate-buffered saline (PBS) containing 0.02% (v/v) $NaN_3$ and then concentrated by ultrafiltration using AMICON YM30 centrifugal filter units.

In the case of PG9, an additional size exclusion chromatography step was included to remove antibody aggregates. After dialysis against SEC buffer (10 mM Tris/HCl, 50 mM NaCl, pH 7.5), the affinity-purified sample (1 mL) was loaded onto a Superdex 200 16/600 column (GE HEALTHCARE) operated at a flow rate of 1 mL min-1. Fractions corresponding to the elution position of monomeric PG9 were combined, dialyzed against PBS containing 0.02% (v/v) $NaN_3$ and then concentrated by ultrafiltration as above.

5. Preparation of Apoplastic Fluid

For the recovery of apoplastic fluid, fully expanded leaves of *Nicotiana benthamiana* C105 μlants (Strasser R et al. Plant Biotechnol J 6 (2008):392-402) were submerged in 100 mM sodium acetate/40 mM ascorbic acid (pH 5.5) prior to vacuum exposure in a desiccator. Exogenous buffer was removed prior to centrifugation of the leaves for 15 min at 2000 g and 4° C. The recovered solution was then concentrated 10-20 fold using Microsep Advance centrifugal devices (10K MWCO; PALL CORPORATION). The total protein content of the concentrate was determined with the (BIO-RAD) Protein Assay kit (BIO-RAD), using bovine serum albumin (BSA) as a standard.

6. Identification of Subtilisin-Like Serine Proteases Present in Apoplastic Fluid Concentrated apoplastic fluid prepared from *Nicotiana benthamiana* C105 μlants (see item 5) was incubated for 1 h at 37° C. with 10 μM FP-biotin (SANTA CRUZ BIOTECHNOLOGY). The sample (2.5 mL) was then chromatographed on a PD-10 column (GE HEALTHCARE) equilibrated in 100 mM sodium acetate (pH 5.5). The recovered eluate (3.5 ml) was incubated with 40 μL avidin-agarose beads (SIGMA-ALDRICH) for 16 h at 4° C. under constant agitation. The beads were washed four times with 4 mL 100 mM sodium acetate (pH 5.5) and once with 4 mL 10 mM Tris/HCl (pH 6.8) prior to elution of the bound proteins with 80 μL SDS-PAGE sample buffer (5 min, 95° C.). The samples were then subjected to 12.5% SDS-PAGE under reducing conditions prior to staining of the gel with Coomassie Brilliant Blue R-250. The 60-80 kDa bands were excised, S-carboxamidomethylated and then digested with trypsin (PROMEGA). The peptides thus generated were fractionated on a THERMO BIOBASIC C18 separation column (5 μm particle size, 150×0.36 mm) operated using a Dionex Ultimate 3000 system (WATERS). A gradient from 95% solvent A and 5% solvent B (solvent A: 65 mM ammonium formate buffer at pH 3.0, B: 100% acetonitrile) to 32% B in 45 min was applied, followed by a 15-min gradient from 32% B to 75% B, at a flow rate of 6 μL/min. Eluted peptides were analysed online on a maxis 4G ETD Q-TOF mass spectrometer (Bruker) equipped with an electrospray ionization source and operated in the positive ion mode (m/z range: 150-2200).

7. Purification of Recombinant Subtilisin-Like Serine Proteases

Leaves of *Nicotiana benthamiana* C105 μlants (Strasser R et al. Plant Biotechnol J 6 (2008):392-402) expressing a subtilisin-like serine protease construct were submerged in extraction buffer (50 mM sodium phosphate/200 mM KCl, pH 7.0) prior to vacuum exposure in a desiccator. Exogenous buffer was removed prior to centrifugation of the leaves for 15 min at 2000 g and 4° C. The recovered solution was then supplemented with 20 mM imidazole and loaded on a 1 mL column of Chelating Sepharose (GE HEALTHCARE) charged with $Ni^{2+}$ ions. After washing with the same buffer, the recombinant subtilisin-like serine protease was eluted with 250 mM imidazole in extraction buffer. Protein-containing eluate fractions were pooled, dialysed twice against 2 liters of extraction buffer and then concentrated by ultrafiltration using Microsep Advance centrifugal devices (10K MWCO; PALL CORPORATION).

8. In Vitro Degradation Assays

Monoclonal antibodies (200 μg/mL) produced in *Nicotiana benthamiana* C105 μlants or CHO cells (2F5: POLYMUN SCIENTIFIC, AB001; 2G12: POLYMUN SCIENTIFIC, AB002; PG9, POLYMUN SCIENTIFIC, AB015) were treated with concentrated apoplastic fluid of *Nicotiana benthamiana* C105 μlants (100 μg/mL) or purified proteases (10-100 μg/mL) in 100 mM sodium acetate (pH 5.5). After incubation for up to 16 h, reactions were stopped by addition of SDS-PAGE sample buffer.

For isolation of mAb degradation products, antibodies (250 g) were digested with apoplastic fluid or purified subtilisin-like serine proteases in 500 μL 100 mM sodium acetate (pH 5.5) to completion. After addition of 10 μL settled rProtein A Sepharose 4 Fast Flow beads, the samples were incubated for 2 h at 4° C. under constant agitation. The beads were then collected by centrifugation, washed four times with 500 μL PBS prior to elution of the bound antibody fragments with 100 μL 100 mM glycine (pH 3.0). The eluate was immediately neutralized with 10 μL 1 M Tris/HCl (pH 8.0). This elution/neutralization cycle was repeated four times. All eluate fractions were combined and concentrated by ultrafiltration after buffer exchange into PBS containing 0.02% (v/v) $NaN_3$.

9. Western Blotting

Samples were fractionated by 12.5% SDS-PAGE under reducing conditions and then blotted on nitrocellulose membranes (GE HEALTHCARE). After blocking for 1 h in PBS containing 3% BSA, the membranes were incubated with a γ-chain-specific goat anti-human IgG peroxidase conjugate (SIGMA-ALDRICH, A8775) at a concentration of 0.03 μg/mL PBS containing 0.05% Tween 20 (PBST) and 0.5% BSA for 90 min prior to development using chemiluminescence reagents (BIO-RAD).

10. Cleavage Site Analysis

N-terminal sequence analysis of bands blotted on polyvinylidene difluoride membranes (BIO-RAD) was performed by Edman degradation (Niemer M et al. Biotechnol J 9 (2014):493-500). Alternatively, antibodies or their degradation products were digested with PNGase F (ROCHE) to release their N-glycans, reduced with 10 mM DTE (1 h, 56° C.) and then fractionated on a THERMO PROSWIFT RP-4H column (250×0.20 mm) using a Dionex UltiMate 3000 HPLC system (THERMO SCIENTIFIC). After application of the sample (5 μl), elution was performed at 65° C. and a flow rate of 8 μl/min with a gradient of 20-95% solvent B (80% acetonitrile in 0.01% trifluoroacetic acid) in solvent A (0.05% trifluoroacetic acid) over 40 min as follows: 20-65% B (15 min), 65-95% B (5 min). Eluted polypeptides were analysed online on a maxis 4G ETD Q-TOF mass spectrometer (BRUKER, Billerica, USA) equipped with an electrospray ionization source and operated in the positive ion mode (m/z range: 400-3800). The analysis files were deconvoluted (Maximum Entropy Method) using DataAnalysis 4.0 (BRUKER) and manually annotated.

11. ELISA Assays 96-well enzyme-linked immunosorbent assay (ELISA) plates were coated with 100 ng per well of the respective antigen (2F5: gp41 peptide GGGLELDKWASL (SEQ ID NO: 36) (POLYMUN SCIENTIFIC); wild-type 2G12: HIV-1 UG37 gp140 (POLYMUN SCIENTIFIC); PG9: HIV-1 ZM109 gp120, Loos A et al. Proc Natl Acad Sci USA 112 (2015):12675-12680) or Fc-specific goat anti-human IgG $F(ab')_2$ fragments (SIGMA-ALDRICH, I3391) in 50 mM sodium carbonate/bicarbonate (pH 9.6) for 16 h at 4° C. The wells were then washed with PBST and subsequently incubated with mAb samples (starting concentration: 1-8 μg/mL) serially diluted (1:2) in PBST containing 1% BSA (dilution buffer) for 1 h at 22-24° C. After washing, bound antibodies were detected with 0.03 μg/mL γ-chain-specific goat anti-human IgG peroxidase conjugate (SIGMA-ALDRICH, A8775) in dilution buffer. After 1 h at 22-24° C., plates were washed and then developed with 0.1 mg/ml 3,3',5,5'-tetramethylbenzidine (SIGMA-ALDRICH, T0440) and 0.006% $H_2O_2$ in 35 mM citric acid/65 mM sodium phosphate (pH 5.0) for 15 min at 22-24° C. Reactions were quenched by addition of 90 mM $H_2SO_4$ prior to analysis by spectrophotometry at 450 nm.

A slightly modified ELISA procedure was used for the analysis of 2G12 containing an I19R mutation in the heavy chain (I19R 2G12). Wells were coated with 500 ng HIV-1 UG37 gp140 in PBS. Antibodies (20 μg/mL) were precomplexed with Fc-specific goat anti-human IgG F (ab') 2 fragments (10 μg/mL) for 15 min at 4° C. (Doores K J et al. J Virol 84 (2010):10690-10699) prior to appropriate dilution and addition to the wells. Detection of antigen-bound mAb molecules was performed with 0.1 μg/mL goat anti-human kappa chain peroxidase conjugate (SIGMA-ALDRICH, A7164).

12. Surface Plasmon Resonance Spectroscopy

The antigen binding kinetics of mAb 2F5 and its degradation products were determined by surface plasmon resonance spectroscopy using a Biacore T200 instrument (GE Healthcare) operated at 25° C. The running buffer was PBST containing 0.01% BSA. For multiple-cycle kinetics, purified antibody samples were diluted with running buffer to 37.5 μg/mL and then applied to a Protein A series S sensor chip (GE Healthcare) at a flow rate of 10 μL $min^{-1}$. After mAb capture (20 sec), the chip was exposed to increasing concentrations of gp41 peptide GGGLELDKWASL (SEQ ID NO:36) (for intact 2F5 mAb: 3, 9, 27, 81, 243 nM; for 2F5 degradation product: 50, 100, 200, 400, 800 nM) in running buffer (contact time: 30 sec; dissociation phase: 60 sec). Regeneration was performed with 10 mM glycine/HCl (pH 1.5) for 30 sec at a flow rate of 30 μL $min^{-1}$. A reference cell was operated in parallel (running buffer instead of mAb) to correct for unspecific binding of the analyte to the sensor chip surface. The sensorgrams thus obtained were analyzed with Biacore T200 Evaluation software by global fitting of the data to a 1:1 binding model.

13. Kinetic Analysis of Protease-Inhibitor Interactions

These assays were performed as described (Hohl M et al., 2017, J. Biol. Chem. 292, 6389-6401). A fluorogenic peptide substrate, Abz-VILDAVRA-Y($NO_2$) (SEQ ID NO: 37), was used for measuring the enzymatic activity of the subtilisin-like serine proteases tested. Recombinant inhibitors (prepared as described in Hohl M et al., 2017, J. Biol. Chem. 292, 6389-6401) were added in serial dilutions. Substrate cleavage was monitored in an Infinite M200 Pro microplate reader as increase in relative fluorescence ($\lambda_{ex}$=320 nm; $\lambda_{em}$=420 nm). Inhibition constants ($K_i$) were calculated using the Morrison equation.

Example 1: Apoplastic Fluid Proteases Generate Characteristic Fragments of the Monoclonal Antibodies 2F5, 2G12 and PG9

It was previously shown that the monoclonal anti-HIV antibody 2F5 can be cleaved within its CDR H3 loop when incubated with apoplastic proteases in vitro (Niemer M et al. Biotechnol J 9 (2014):493-500). This has now been also observed for PG9 and a 2G12 variant (I19R 2G12) with a canonical domain architecture (FIG. 1). To identify the cleavage sites, the degradation products were affinity-purified and then subjected to N-terminal sequencing analysis. In each case, the main cleavage site was located in the CDR H3 loop. For 2G12, additional cleavage sites were identified in the segment adjacent to the C-terminus of the CDR H3 loop (Table 1).

Example 2: Proteolytic Cleavage Impairs Antigen Binding by 2F5, 2G12 and PG9

Figure 2A:
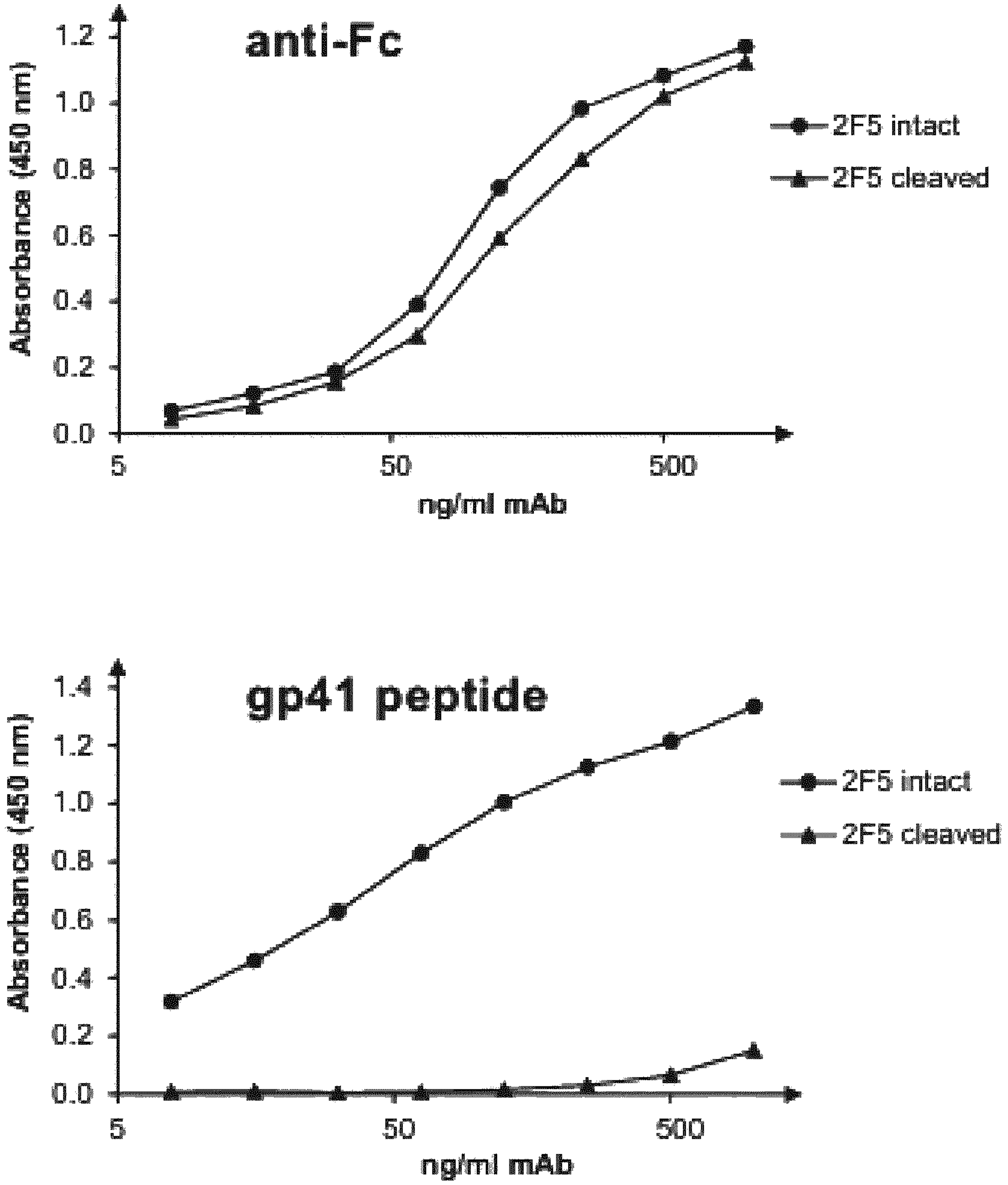
FIG. 2*a-c* shows that cleaved 2F5, 2G12 and PG9 have a much lower antigen-binding activity than the intact antibodies as determined by ELISA with the respective cognate antigens as ligands. The constant domains of the antibodies are proteolysis-resistant under the conditions used, as demonstrated by equal binding of anti-Fc antibodies.
Figure 2B:
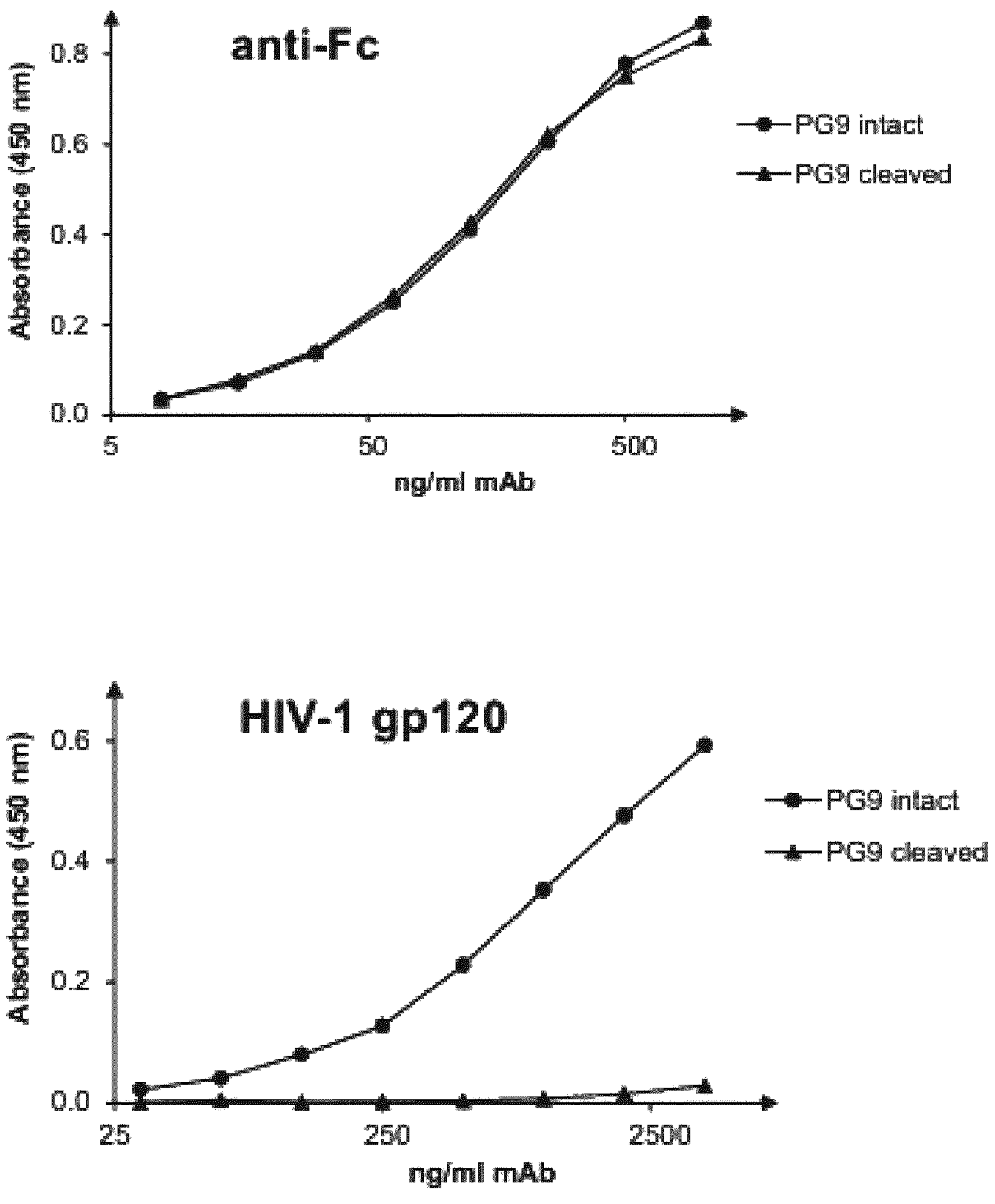
Figure 2C:
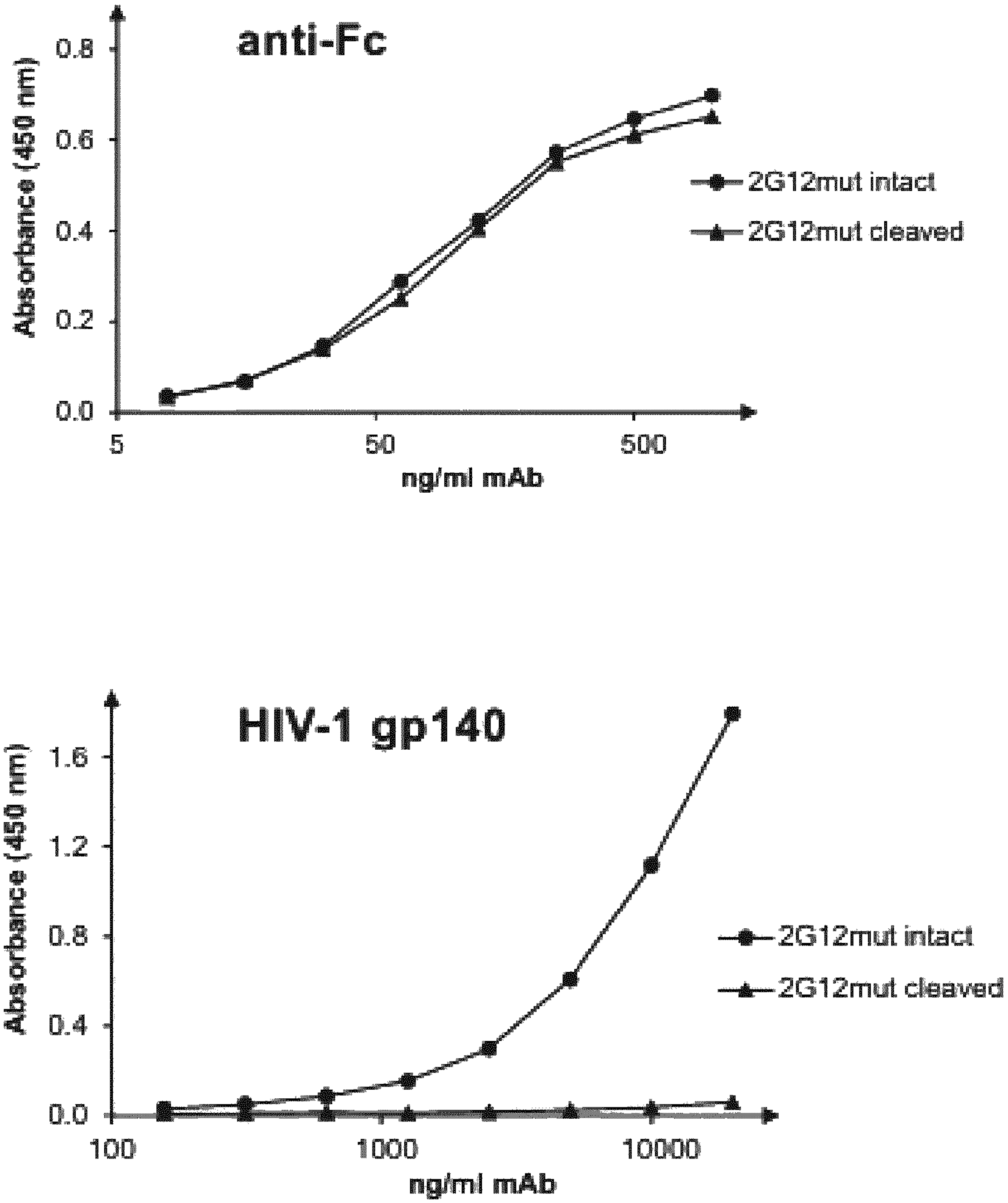
Figure 3:
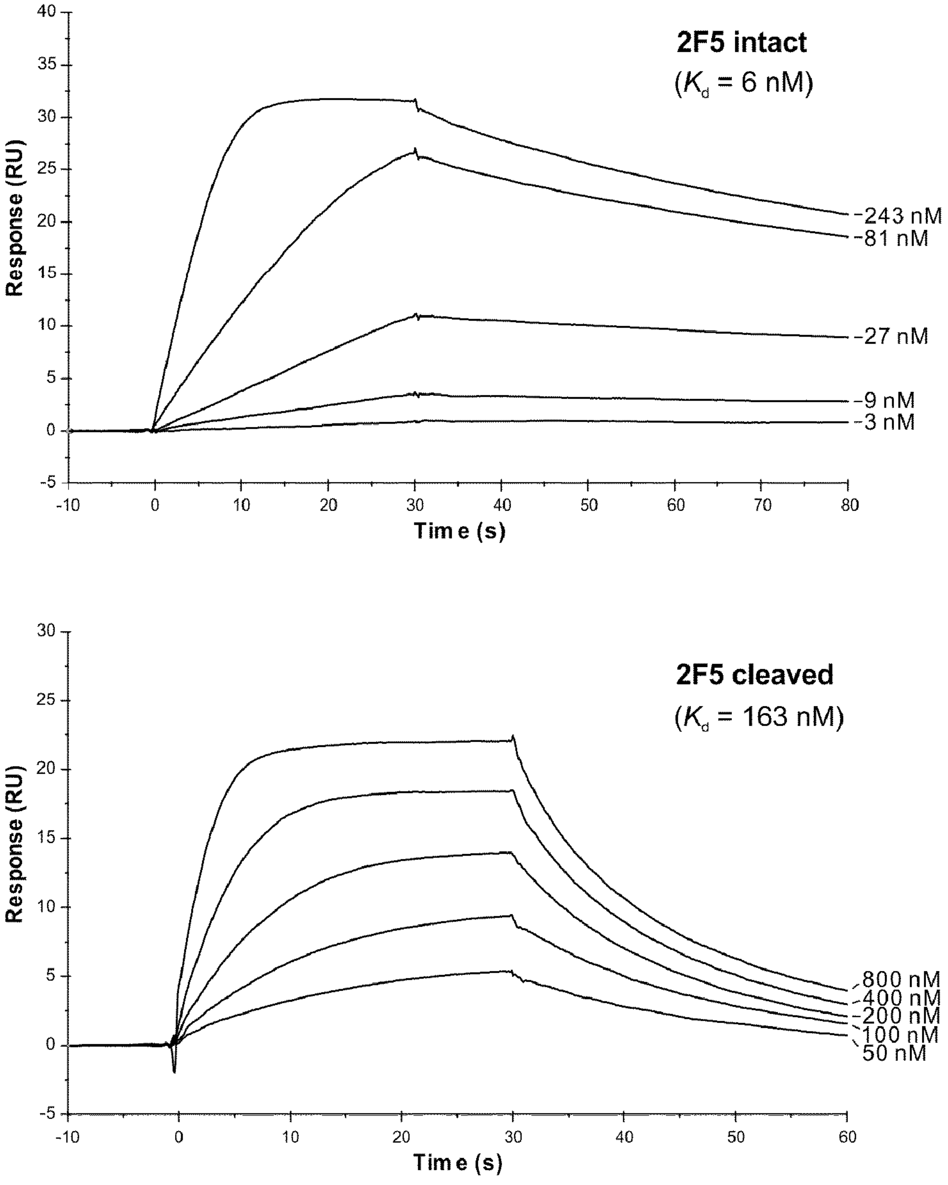
FIG. 3 shows that the dissociation constant of cleaved 2F5 for its antigen gp41 peptide is far higher than for the intact antibody as determined by surface plasmon resonance (SPR) spectroscopy.

Previous studies have indicated that the CDR H3 loops are important for the interactions of 2F5, 2G12 and PG9 with their cognate antigens (Zwick M B et al. J Virol 78 (2004):3155-3161; Doores K J et al. J Virol 84 (2010): 10690-10699; McLellan J S et al. Nature 480 (2011):336-343). To investigate the antigen-binding properties of cleaved 2F5, 2G12 and PG9, suitable ligands and assay conditions had to be chosen. The antigen-binding activity of 2F5 can be tested with gp41-based peptides (Zwick M B et al. J Virol 78 (2004):3155-3161). The nondomain-swapped variant of 2G12 (I19R 2G12) requires precomplexing with anti-Fc antibodies for detectable binding to HIV-1 envelope glycoproteins (Doores K J et al. J Virol 84 (2010):10690-10699). PG9 has been described to bind to gp120 monomers of selected HIV strains including ZM109. Therefore HIV-1 ZM109 gp120 containing a C-terminal hexahistidine tag was expressed in mammalian cells and purified by metal-chelate affinity chromatography (Loos A et al. Proc Natl Acad Sci USA 112 (2015):12675-12680). For all three antibodies, limited proteolysis within the CDR H3 loop by apoplastic proteases severely reduced binding to the respective antigen (FIG. 2*a-c*). For intact and cleaved 2F5, the avidity of the antigen-antibody interaction was also determined by surface plasmon resonance spectroscopy. These experiments demonstrated that cleavage of 2F5 by apoplastic proteases leads to a more than 20-fold reduction of its affinity to gp41 (FIG. 3).

Example 3: SBT1 and SBT2 Cleave 2F5, 2G12 and PG9 at the Same Sites as Apoplastic Fluid Previous studies have indicated that serine proteases participate in the proteolysis of 2F5 in *N. benthamiana*

TABLE 1

Sequences of 2F5, 2G12 and PG9 heavy chains. CDR H3 loops (underlined) and their tips (italic) are highlighted. Cleavage sites by apoplastic fluid proteases are indicated by arrows.

Figure 4A:
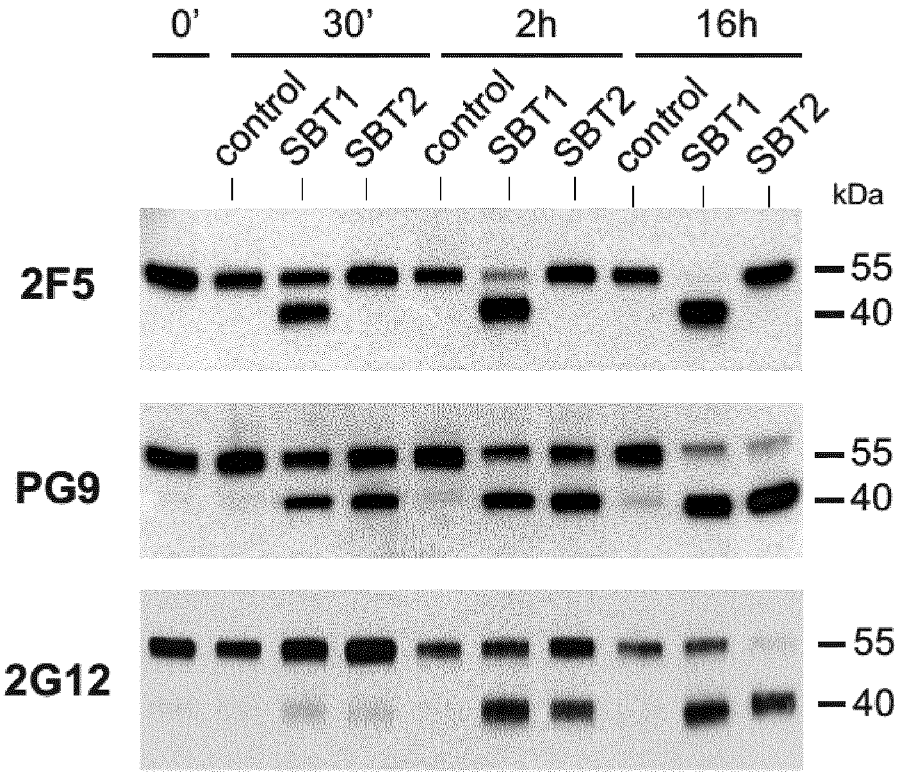
FIG. 4*a-b* show that purified SBT1 and SBT2 can cleave the heavy chains of 2F5, 2G12 and PG9 at the same positions as apoplastic fluid. The observed cleavage sites (listed in Tables 2 and 3) are identical to those observed for apoplastic fluid. Other serine proteases (trypsin, SBT3) cannot cleave the monoclonal antibody 2F5 at these positions.
Figure 4B:
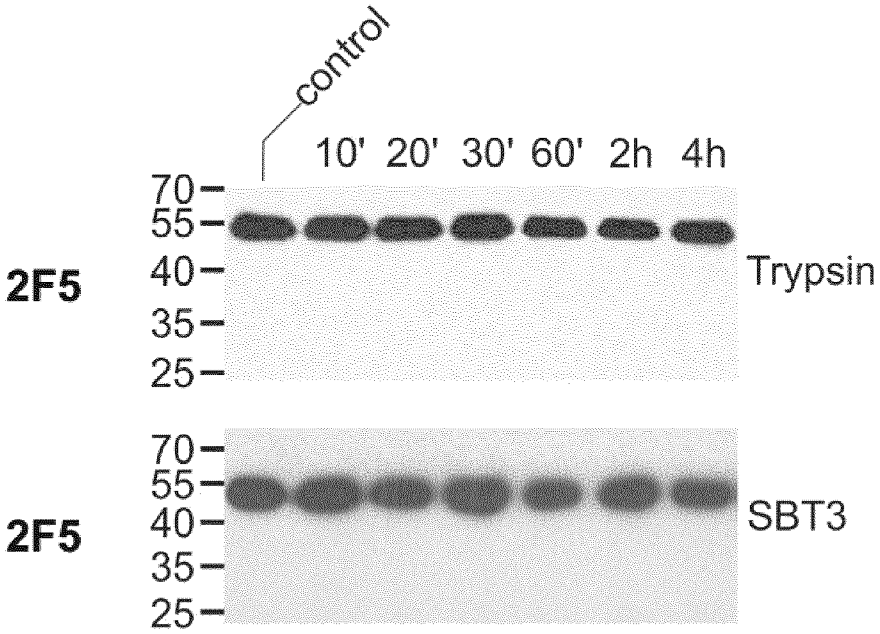
Figure 5A:
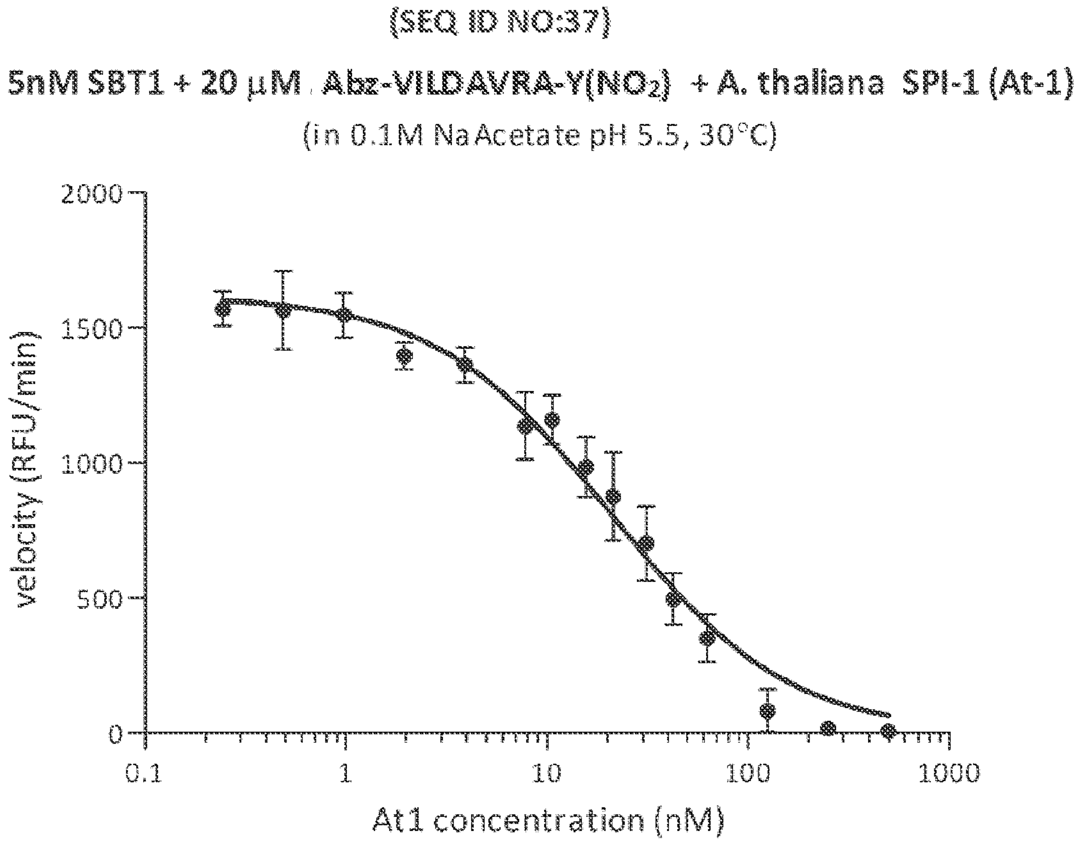
FIG. 5*a-h* shows that SBT1 and SBT2 are effectively inhibited by subtilisin propeptide-like inhibitors.
Figure 5B:
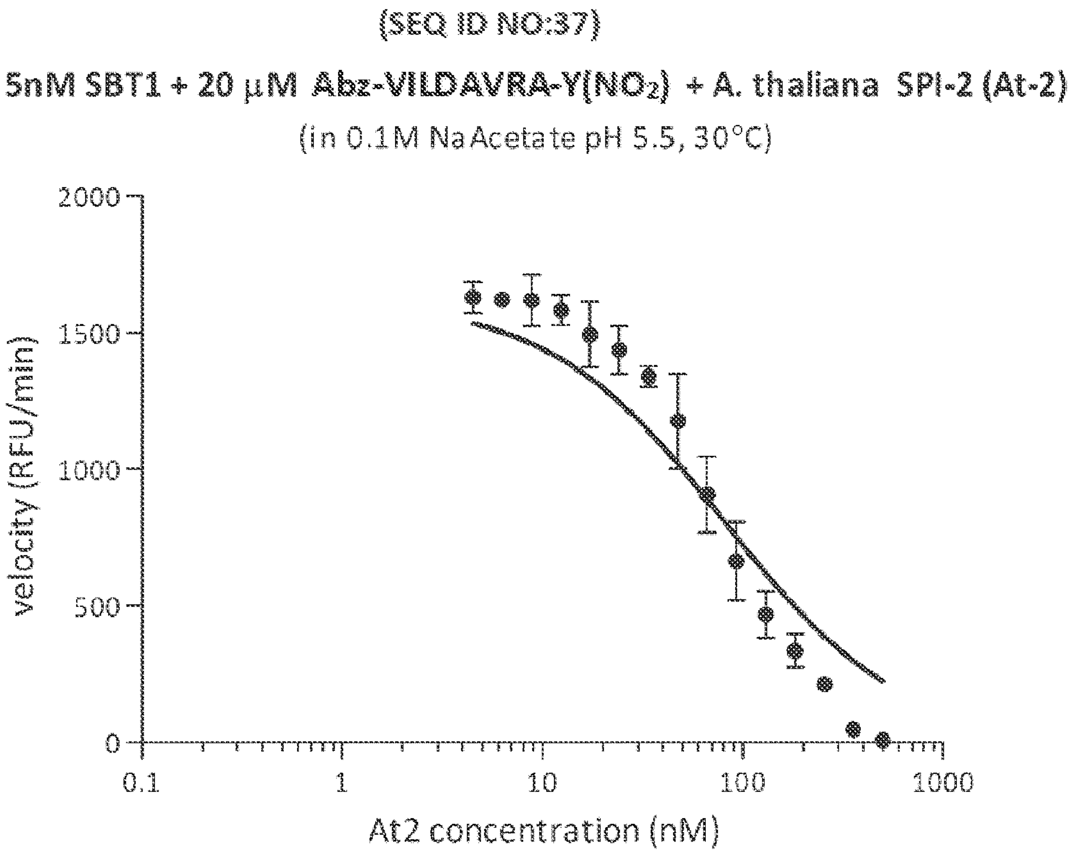
Figure 5C:
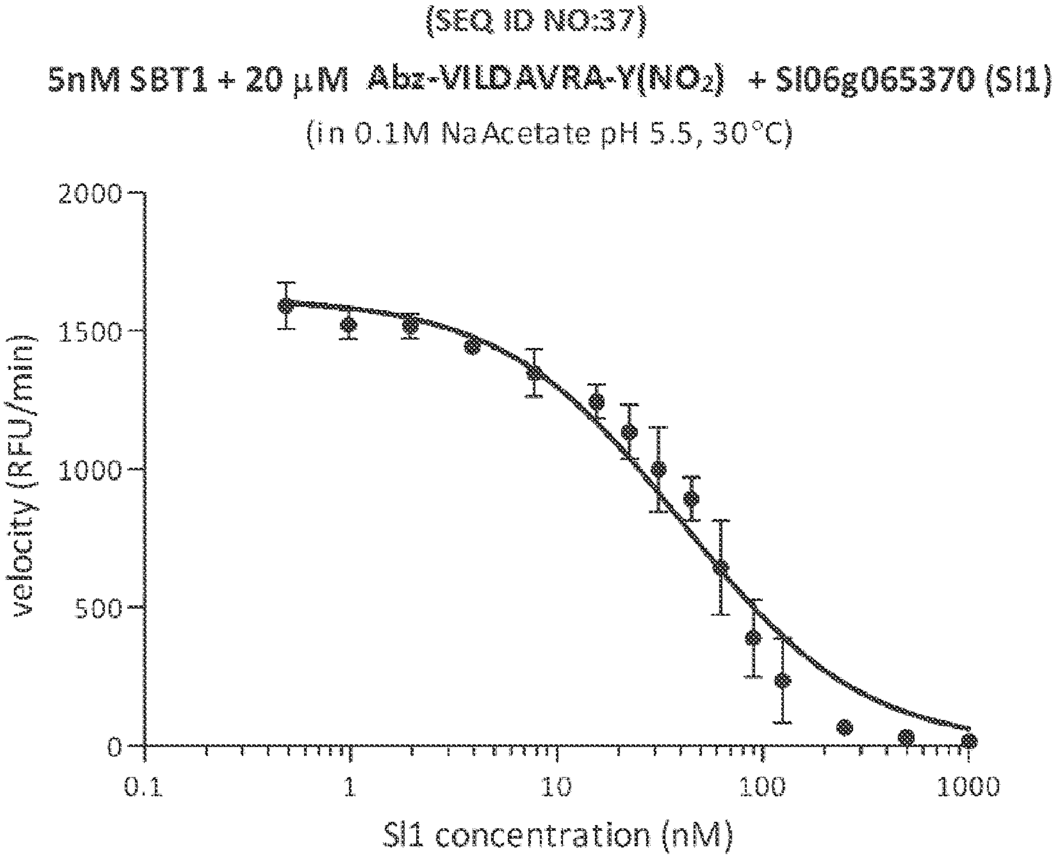
Figure 5D:
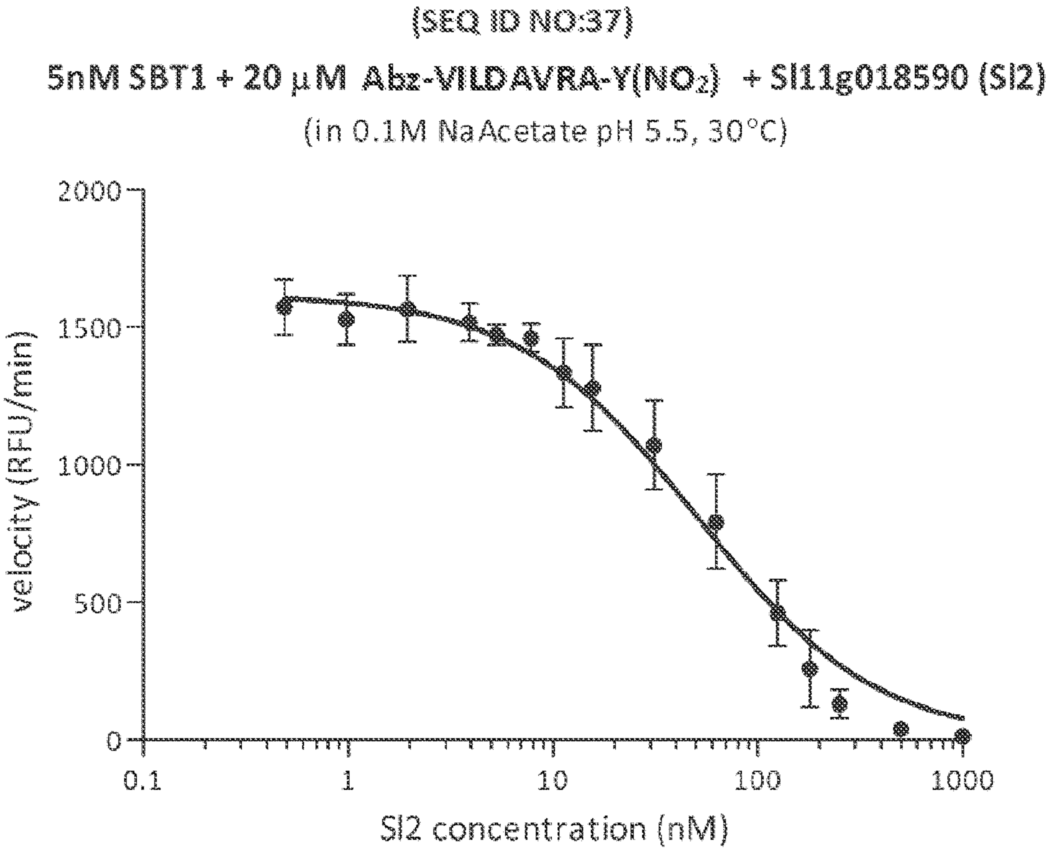
Figure 5E:
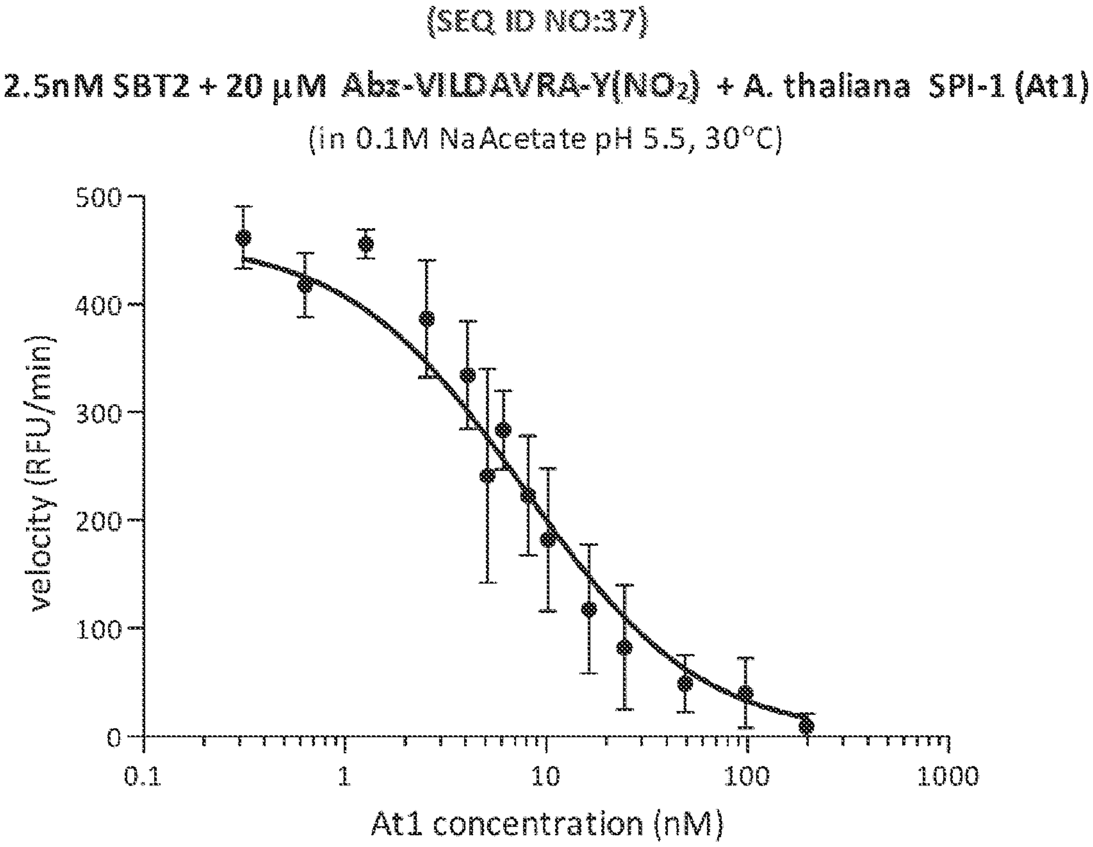
Figure 5F:
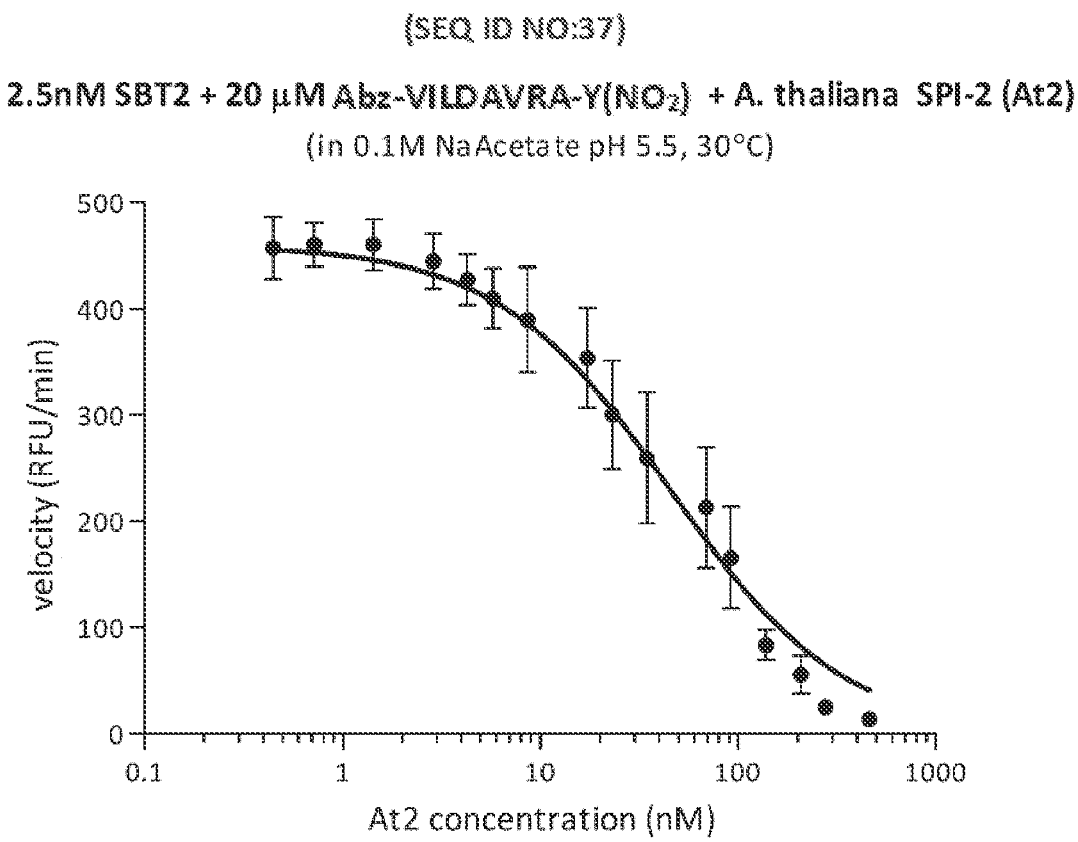
Figure 5G:
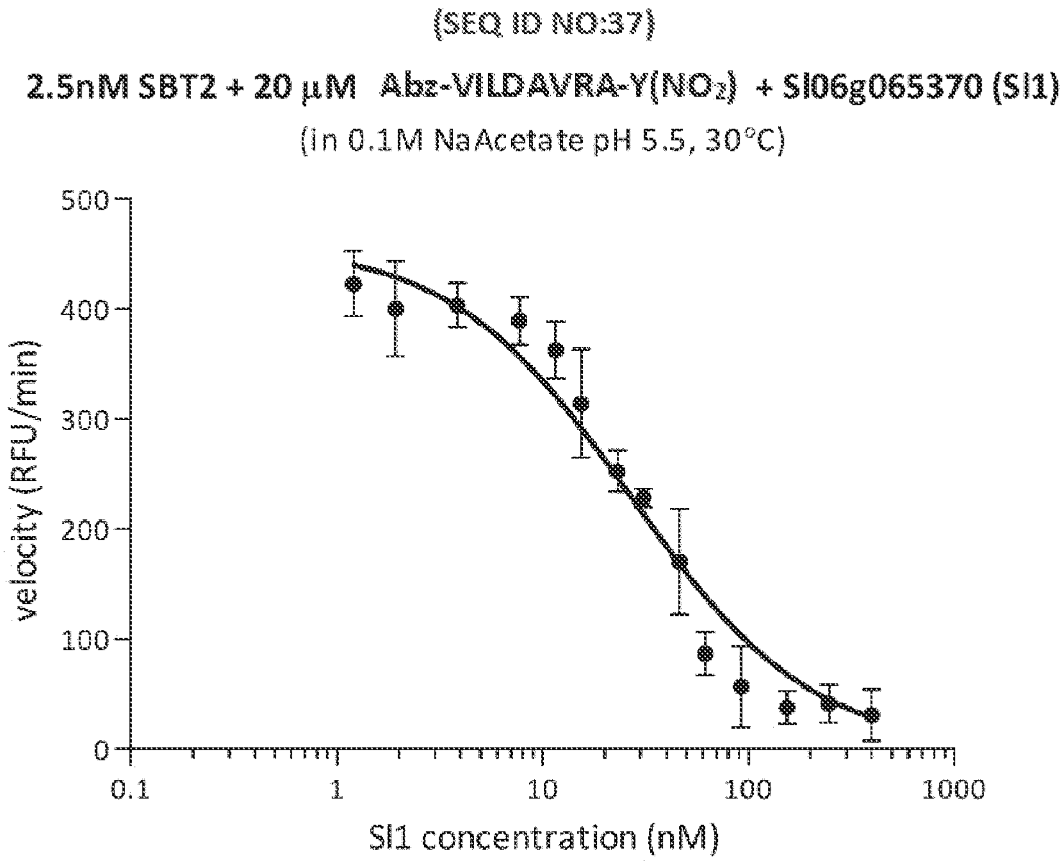
Figure 5H:
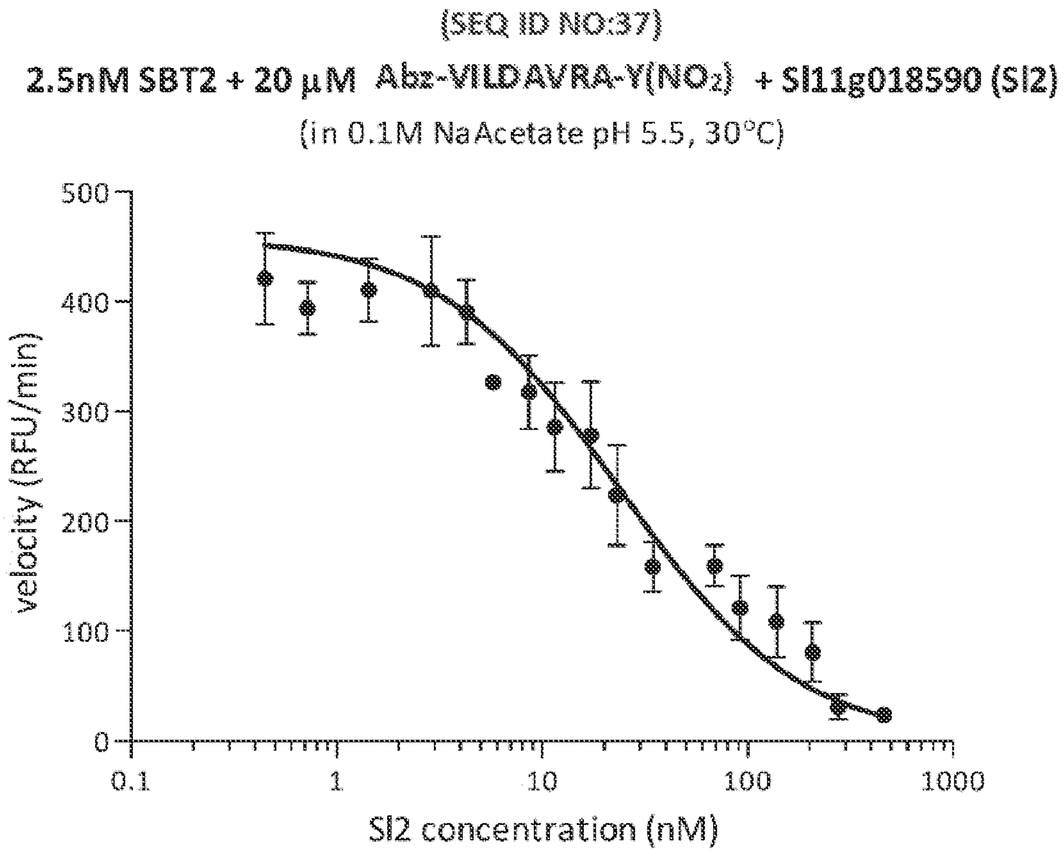

2F5 (heavy chain) (SEQ ID No. 30):
RITLKESGPPLVKPTQTLTLTCSFSGFSLSDFGVGVGWIRQPPGKALEWLAIIYSDDD
KRYSPSLNTRLTITKDTSKNQVVLVMTRVSPVDTATYFCAHRRGPTT*LF*↓*GV*PIARG
PVNAMDVWGQGITVTISSTSTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDPEV
KFNWYVDGVEVHNAKIKPREEQYNSTYRVVSVLIVLHQDWLNGKEYKCKVSNKAFPAP
IEKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPGK I19R 2G12 (heavy chain) (SEQ ID No. 31):
EVQLVESGGGLVKAGGSLRLSCGVSNFRISAHTMNWVRRVPGGGLEWVASISTSSTYR
DYADAVKGRFTVSRDDLEDFVYLQMHKMRVEDTAIYYCARKGSD↓*RLSD*NDPFDAWG
PG↓TV↓VTVSPASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKKVEPKSCD
KTHTCPPCPAPELLGGPSVFLFPPKPKDTLMISRTPEVTCVVVDVSHEDPEVKFNWYV
DGVEVHNAKIKPREEQYNSTYRVVSVLTVLHQDWLNGKEYKCKVSNKAFPAPIEKTIS
KAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK PG9 (heavy chain) (SEQ ID No. 32):
QRLVESGGGVVQPGSSLRLSCAASGFDFSRQGMHWVRQAPGQGLEWVAFIKYDGSEKY
HADSVWGRLSISRDNSKDTLYLQMNSLRVEDTATYFCVREAGGPDYR*NGYNYY*↓*D*↓*F*
YDGYYNYHYM↓DVWGKGTTVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNT
KVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLIVLHQDWLNGKEYKCKVSN
KALPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSL
SLSPGK (Niemer M et al. Biotechnol J 9 (2014):493-500). We have therefore utilized a biotin-tagged version of an activity-based probe for serine hydrolases for the selective labelling of serine proteases present in apoplastic fluid extracted from *N. benthamiana* leaves. After isolation with immobilized avidin, the captured proteins were identified by mass spectrometry. Exploiting the availability of a draft genome sequence for *N. benthamiana* (Bombarely A et al. Mol Plant Microbe Interact 25 (2012):1523-1530), the respective CDNAs could be cloned by RT-PCR using primers based on the peptide sequences obtained by mass spectrometry and then ectopically expressed in *N. benthamiana* by means of agroinfiltration. Two recombinant serine proteases, SBT1 and SBT2, were purified by nickel-chelate affinity chromatography exploiting hexahistidine tags exogenously added to their C-termini and then analysed for their capacity to degrade 2F5, PG9 and the non-domain exchanged variant of 2G12 (I19R 2G12). SBT1 was found to degrade all three antibodies. SBT2 was capable of acting on PG9 and I19R 2G12 (FIG. 4*a*). Two other serine proteases, trypsin and SBT3 (Cedzich A et al. J. Biol. Chem. 284 (2009):14068-14078), did not display cleavage activity (FIG. 4*b*) when tested on the monoclonal antibody 2F5. The cleavage products obtained upon digestion of 2F5, I19R 2G12 and PG9 with SBT1 and SBT2 were then characterized by N-terminal sequencing and mass spectrometry. These studies revealed that the combined action of SBT1 and SBT2 can account for all cleavage sites generated by incubation of the antibodies with unfractionated apoplastic fluid (Tables 2 and 3).

TABLE 2

Sequences of 2F5, 2G12 and PG9 heavy chains. CDR H3 loops (underlined) and their tips (italic) are highlighted. Cleavage sites by SBT1 are indicated by arrows.

2F5 (heavy chain) (SEQ ID No. 30):
RITLKESGPPLVKPTQTLTLTCSFSGFSLSDFGVGVGWIRQPPGKALEWLAIIYSDDD
KRYSPSLNTRLTITKDTSKNQVVLVMTRVSPVDTATYFCAHRRGPTT*LF*↓*GV*PIARG
PVNAMDVWGQGITVTISSTSTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKAFPAP
IEKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPGK I19R 2G12 (heavy chain) (SEQ ID No. 31):
EVQLVESGGGLVKAGGSLRLSCGVSNFRISAHTMNWVRRVPGGGLEWVASISTSSTYR
DYADAVKGRFTVSRDDLEDFVYLQMHKMRVEDTAIYYCARKGSD*RLSD*NDPFDAWGPG
↓TV↓VTVSPASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKAFPAPIEKTISKA
KGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK PG9 (heavy chain) (SEQ ID No. 32):
QRLVESGGGVVQPGSSLRLSCAASGFDFSRQGMHWVRQAPGQGLEWVAFIKYDGSEKY
HADSVWGRLSISRDNSKDTLYLQMNSLRVEDTATYFCVREAGGPDYR*NGYNYY*↓*DFY*
DGYYNYHYM↓DVWGKGTTVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTK
VDKKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLIVLHQDWLNGKEYKCKVSNK
ALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLS
LSPGK

TABLE 3

Sequences of 2F5, 2G12 and PG9 heavy chains. CDR H3 loops (underlined) and their tips (italic) are highlighted. Cleavage sites by SBT2 are indicated by arrows.

2F5 (heavy chain) (SEQ ID No. 30):
RITLKESGPPLVKPTQTLTLTCSFSGFSLSDFGVGVGWIRQPPGKALEWLAIIYSDDD
KRYSPSLNTRLTITKDTSKNQVVLVMTRVSPVDTATYFCAHRRGPTT*LFGV*PIARGPV
NAMDVWGQGITVTISSTSTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKAFPAPIE
KTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK I19R 2G12 (heavy chain) (SEQ ID No. 31):
EVQLVESGGGLVKAGGSLRLSCGVSNFRISAHTMNWVRRVPGGGLEWVASISTSSTYR
DYADAVKGRFTVSRDDLEDFVYLQMHKMRVEDTAIYYCARKGSD↓*RLSD*NDPFDAWG
PGTVVTVSPASTKGPSVFPLAPSSKSTSGGTAALGCLVKDYFPEPVTVSWNSGALTSG TABLE 3-continued Sequences of 2F5, 2G12 and PG9 heavy chains. CDR H3 loops (underlined) and their tips (italic) are highlighted. Cleavage sites by SBT2 are indicated by arrows.

VHTFPAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKAFPAPIEKTISKAK
GQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

PG9 (heavy chain) (SEQ ID No. 32):
QRLVESGGGVVQPGSSLRLSCAASGFDFSRQGMHWVRQAPGQGLEWVAFIKYDGSEKY
HADSVWGRLSISRDNSKDTLYLQMNSLRVEDTATYFCVREAGGPDYR*NGYNYYD*↓*FY*
DGYYNYHYMDVWGKGTTVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKV
DKKVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSL
SPGK

Example 4: SBT1 and SBT2 can be Effectively Inhibited by Plant Inhibitors of Subtilisin-Like Serine Proteases In a recent study (Hohl M et al., 2017, J. Biol. Chem. 292, 6389-6401), *A. thaliana* subtilisin propeptide-like inhibitor 1 (SPI-1) and three close relatives from *A. thaliana* (SPI-2) and *S. lycopersicum* (S106g065370, S111g018590) were described. Recombinant versions of these four inhibitors were now produced in *E. coli* following published procedures (Hohl M et al., 2017, J. Biol. Chem. 292, 6389-6401) and then tested for their potential to inhibit SBT1 (SEQ ID No. 2) and SBT2 (SEQ ID No. 14). All four inhibitors (At1, *A. thaliana* SPI-1; At2, *A. thaliana* SPI-2; S11, S106g065370; S12, S111g018590) were found to bind to SBT1 and SBT2 with high affinities, resulting in effective inhibition of the proteases (FIG. 5*a-h*).

CONCLUSION

The examples provided herein aimed at the identification of the proteases affecting the integrity and antigen-binding capacity of the three HIV-specific mAbs 2F5, 2G12 and PG9. Utilizing the activity-based probe FP-biotin, two subtilisin-like serine proteases could be isolated from apoplastic fluid of *Nicotiana benthamiana* C105 µlants and identified by mass spectrometric analysis of their tryptic peptides. The coding sequences of these two proteases were cloned and then used for the expression of recombinant versions of the enzymes, which could be purified by affinity chromatography exploiting their C-terminal tags. Incubation of the mAbs 2F5, 2G12 and PG9 with the purified proteases led to cleavage of the antibodies at exactly the same positions as observed when treated with apoplastic fluid. These results indicate that the identified two subtilisin-like serine proteases are responsible for the fragmentation and inactivation of the mAbs 2F5, 2G12 and PG9 when expressed in plants. The two identified proteases are effectively inhibited by subtilisin propeptide-like inhibitors, which can be exploited for their targeted inactivation in plants.

The invention claimed is:

1. A genetically modified plant or plant cell derived from a wild-type plant or plant cell, wherein the wild-type plant or plant cell is *Nicotiana benthamiana*, said wild-type plant or plant cell producing at least one serine protease consisting of an amino acid sequence of SEQ ID No. 2, wherein the proteolytic activity of the at least one serine protease in the genetically modified plant or plant cell is reduced compared to its activity in the wild-type plant or plant cell, wherein the genetically modified plant or plant cell comprises at least one exogenous nucleic acid molecule encoding at least one antibody.

2. The genetically modified plant or plant cell according to claim 1, wherein the serine protease activity is reduced by at least one amino acid substitution in the catalytic triad of a serine protease motif.

3. The genetically modified plant or plant cell according to claim 1, wherein a promoter of a gene encoding said at least one serine protease of the wild-type plant or plant cell is mutated in the genetically modified plant or plant cell at at least one position of its nucleic acid sequence to reduce its expression rate.

4. The genetically modified plant or plant cell according to claim 1, wherein an inhibitor of said at least one serine protease is overexpressed in the genetically modified plant or plant cell to reduce the expression rate of the at least one serine protease or to inhibit the proteolytic activity of the at least one serine protease.

5. The genetically modified plant or plant cell according to claim 1, wherein the at least one antibody is an antibody binding to an HIV surface protein.

6. The genetically modified plant or plant cell according to claim 5, wherein the antibody is an antibody selected from the group consisting of 2F5, 2G12, PG9, and PG16.

7. A method for producing at least one antibody by cultivating the genetically modified plant or plant cell according to claim 1.

* * * * *